(12) United States Patent
Fuentes et al.

(10) Patent No.: US 10,982,055 B2
(45) Date of Patent: Apr. 20, 2021

(54) THERMOREVERSIBLE POLYMERS AND METHODS OF USE THEREOF

(71) Applicant: The Regents of the University of California, Oakland, CA (US)

(72) Inventors: Christina Marie Fuentes, Berkeley, CA (US); Barbara L. Ekerdt, Berkeley, CA (US); David V. Schaffer, Danville, CA (US); Rachel Segalman, Santa Barbara, CA (US); Yuguo Lei, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 18 days.

(21) Appl. No.: 15/758,233

(22) PCT Filed: Oct. 4, 2016

(86) PCT No.: PCT/US2016/055362
§ 371 (c)(1),
(2) Date: Mar. 7, 2018

(87) PCT Pub. No.: WO2017/062375
PCT Pub. Date: Apr. 13, 2017

(65) Prior Publication Data
US 2018/0244859 A1    Aug. 30, 2018

Related U.S. Application Data

(60) Provisional application No. 62/237,446, filed on Oct. 5, 2015.

(51) Int. Cl.
| | |
|---|---|
| *C08J 3/075* | (2006.01) |
| *C08F 220/54* | (2006.01) |
| *C08F 220/14* | (2006.01) |
| *C08F 8/32* | (2006.01) |
| *C08F 20/54* | (2006.01) |
| *C08F 220/18* | (2006.01) |
| *C08L 33/24* | (2006.01) |
| *C08L 33/12* | (2006.01) |
| *C08F 20/56* | (2006.01) |
| *C08F 220/56* | (2006.01) |
| *C08L 33/26* | (2006.01) |
| *C08L 5/08* | (2006.01) |
| *C12N 5/0735* | (2010.01) |
| *C12N 5/074* | (2010.01) |

(52) U.S. Cl.
CPC .............. *C08J 3/075* (2013.01); *C08F 8/32* (2013.01); *C08F 20/54* (2013.01); *C08F 20/56* (2013.01); *C08F 220/14* (2013.01); *C08F 220/18* (2013.01); *C08F 220/54* (2013.01); *C08F 220/56* (2013.01); *C08L 5/08* (2013.01); *C08L 33/12* (2013.01); *C08L 33/24* (2013.01); *C08L 33/26* (2013.01); *C12N 5/0606* (2013.01); *C12N 5/0607* (2013.01); *C08L 2201/54* (2013.01); *C12N 2500/50* (2013.01)

(58) Field of Classification Search
CPC ........... C08J 3/075; C08L 33/26; C08L 33/12; C08L 33/24; C08L 5/08; C08L 2201/54; C08F 220/56; C08F 20/56; C08F 220/18; C08F 20/54; C08F 8/32; C08F 220/14; C08F 220/54; C12N 5/0607; C12N 5/0606; C12N 2500/50
See application file for complete search history.

(56) References Cited

U.S. PATENT DOCUMENTS

2007/0249044 A1 * 10/2007 Desai .................... C12M 25/14
435/325
2014/0213517 A1    7/2014 Fujimoto et al.

FOREIGN PATENT DOCUMENTS

WO    WO 2007/146261    12/2007

OTHER PUBLICATIONS

Zhang, J et al. Folate-conjugated thermo-responsive micelles for tumor targeting. Journal of Biomedical Materials Research A. 2012. 100A(11): 3134-3142. (Year: 2012).*
Yoshioka, H et al. A synthetic hydrogel with thermoreversible gelation, III: an NMR study of the sol-gel transition. Polymers for Advanced Technologies. 1994. A31(1): 113-125. (Year: 1994).*
Garbern, JC et al. Injectable pH- and temperature-responsive poly(N-isopropylacrylamide-co-propylacrylic acid) copolymers for delivery of angiogenic growth factors. Biomacromolecules. 2010. 11: 1833-1839. (Year: 2010).*
Li, et al.; "Synthesis of Amphiphilic and Thermoresponsive ABC Miktoarm Star Terpolymer via a Combination of Consecutive Click Reactions and Atom Transfer Radical Polymerization"; Journal of Polymer Science: Part A: Polymer Chemistry; vol. 47, No. 16, pp. 4001-4013 (2009).

* cited by examiner

*Primary Examiner* — Renee Claytor
*Assistant Examiner* — Susan E. Fernandez
(74) *Attorney, Agent, or Firm* — Bozicevic Field & Francis, LLP; Paula A. Borden

(57) ABSTRACT

The present disclosure provides thermoreversible polymers, hydrogel compositions comprising the thermoreversible polymers, as well as methods of making and using the thermoreversible polymers.

22 Claims, 30 Drawing Sheets

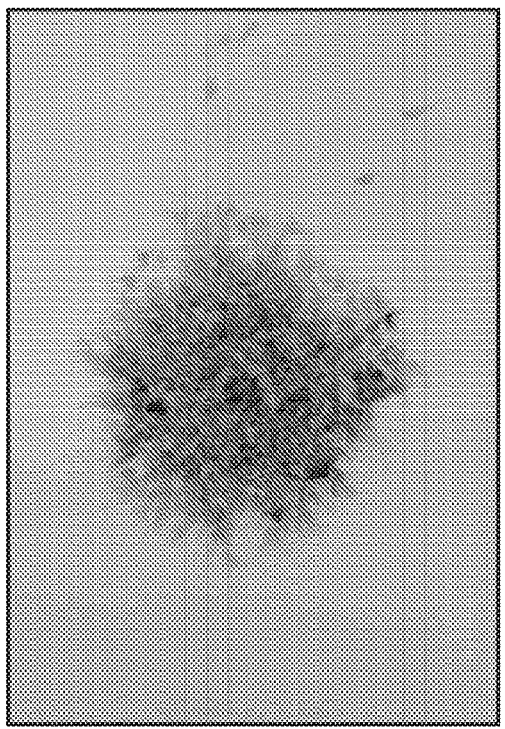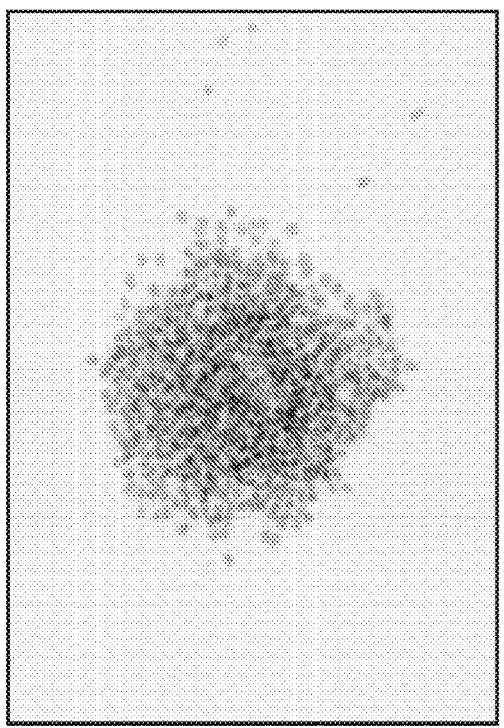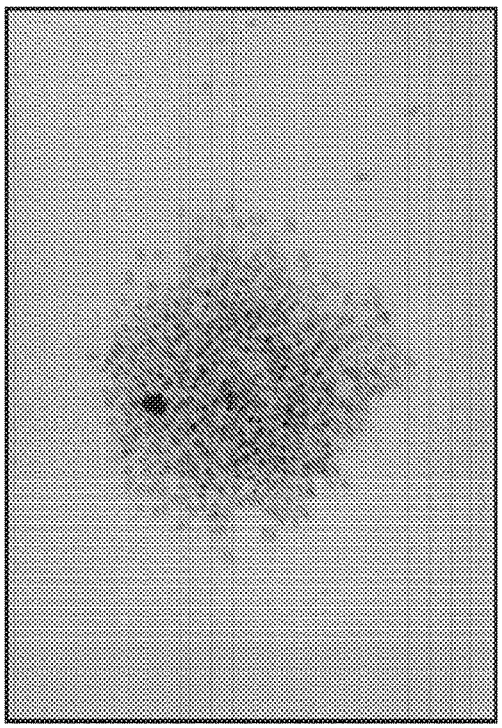

FIG. 10 (Cont.)
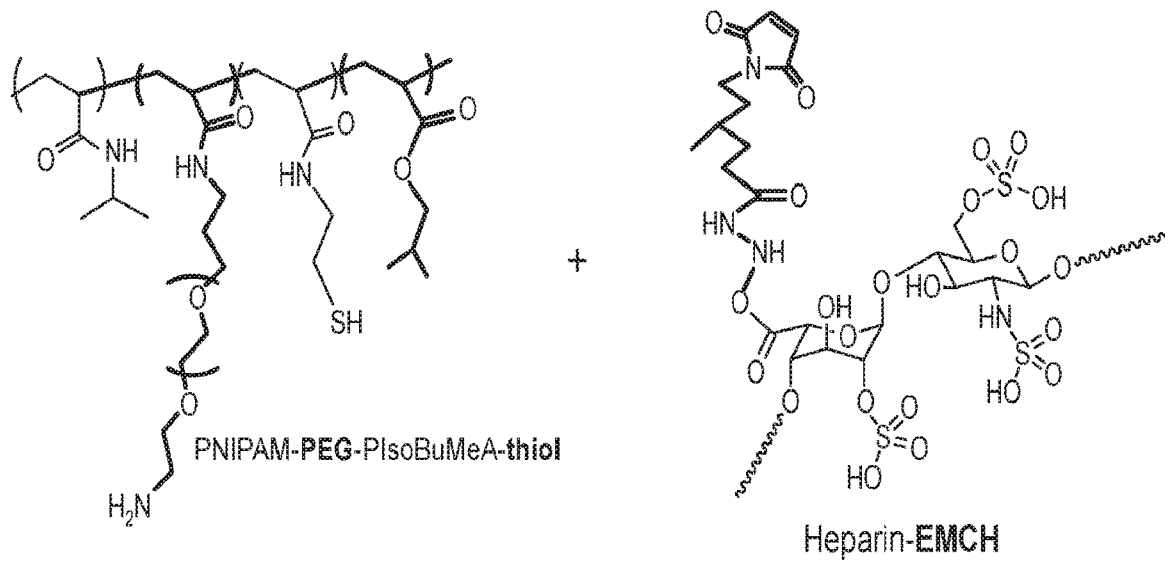
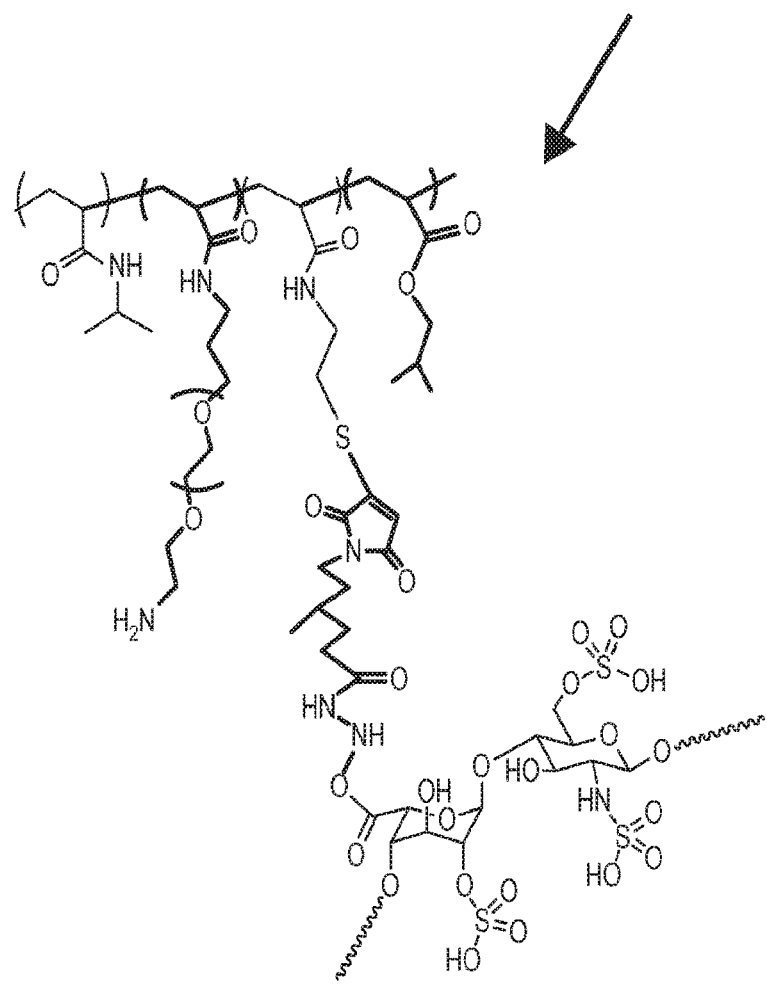

PEG length affects storage modulus

Polymer size affects storage modulus

PNIPAAm-SH

Hyaluronic acid-vinyl sulfone

Hyaluronic acid-PNIPAAm

Day 1 single cells
200 μm

Day 4, round 4 TCTF
200 μm

Day 4, round 1 H9
200 μm

Day 4, round 1 H1
200 μm

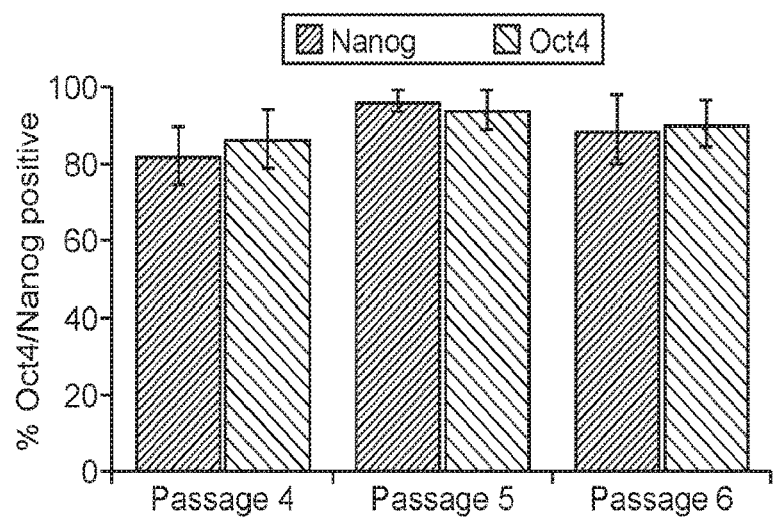
FIG. 29C
FIG. 30A
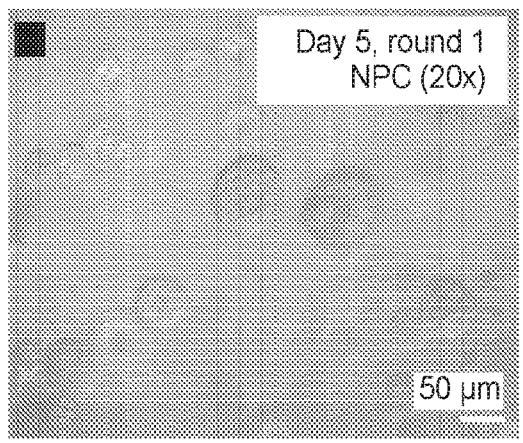
FIG. 30B
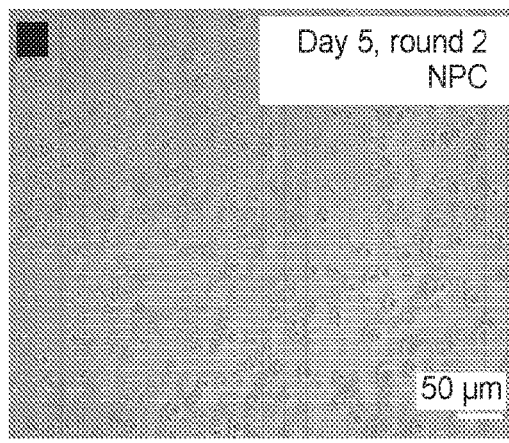
FIG. 30C
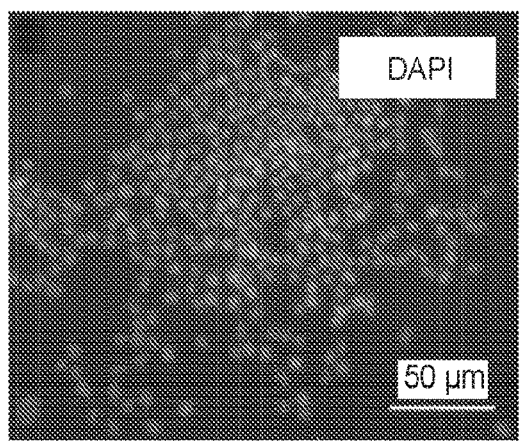
FIG. 30D
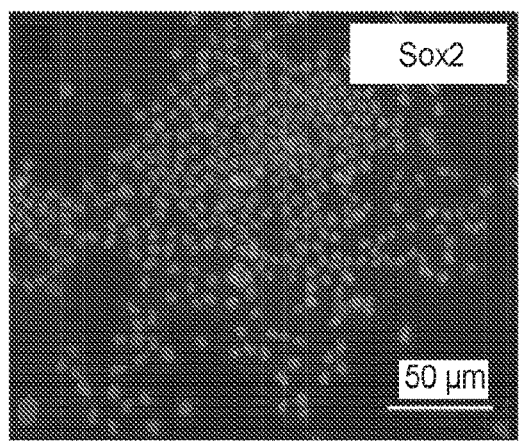

THERMOREVERSIBLE POLYMERS AND METHODS OF USE THEREOF

CROSS-REFERENCE

This application claims the benefit of U.S. Provisional Patent Application No. 62/237,446, filed Oct. 5, 2015, which application is incorporated herein by reference in its entirety.

INTRODUCTION

Patients who suffer from a broad range of disorders involving tissue degeneration—such as Parkinson's disease, a myocardial infarction (heart attack), or liver failure—could potentially benefit from implantation of new healthy cells or engineered tissues to replace damaged or diseased ones, a process known as cell replacement therapy. Stem cells have the unique abilities to replicate indefinitely in an immature state and to differentiate into various types of cells found in the body. Therefore, stem cells can be harnessed as the cell source for such cell replacement and tissue engineering therapies. As such, systems and methods for scalable stem cell expansion and differentiation are of interest.

SUMMARY

The present disclosure provides thermoreversible polymers, hydrogel compositions comprising the thermoreversible polymers, as well as methods of making and using the thermoreversible polymers.

In a first aspect, the present disclosure provides a thermoreversible polymer comprising: a N-isopropylacrylamide co-monomer; an alkyl [meth]acryl[ate/amide] co-monomer; and a PEG acrylamide co-monomer. In some cases, the alkyl [meth]acryl[ate/amide] co-monomer is an isobutyl methacrylate co-monomer. In some cases, the thermoreversible polymer further comprises a modifying acryl[ate/amide] co-monomer comprising a linked functional group or a linked modifying agent. In some cases, the thermoreversible polymer comprises a segment described by formula (I):

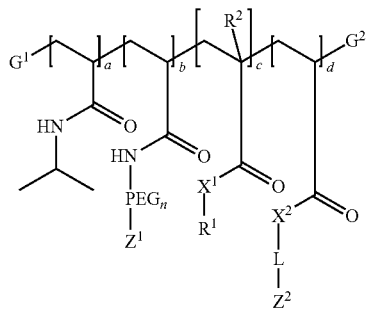

(I)

wherein:
a, b, c and d are molar fractions of the co-monomers, wherein a and c are each greater than 0;
$PEG_n$ is a polyethylglycol polymer;
$Z^1$ is an optional terminal functional group or a linked modifying agent;
$Z^2$ is a functional group or a linked modifying agent;
L is a linker;
$X^1$ and $X^2$ are each independently O or NH;
$R^1$ is a lower alkyl;
$R^2$ is H or methyl; and
$G^1$ and $G^2$ are each independently selected from a polymer segment, a terminal group, a linker and a linked modifying agent.

In some embodiments of the first aspect, the thermoreversible polymer is described by formula (II):

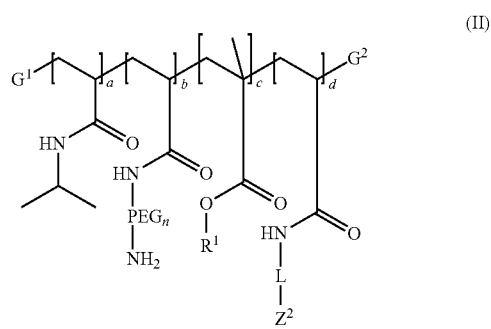

(II)

wherein $G^1$, $G^2$, $PEG_n$, $R^1$, L, $Z^2$ and a-d are as described above. In some cases, d is 0. In some cases, b>0. In some cases, a>0.8; 0.1>b>0; and 0.2>c>0. In some cases, $R^1$ is selected from the group consisting of methyl, ethyl, propyl, butyl, pentyl, isopropyl, isobutyl, isopentyl, tert-butyl, cyclopropyl, and cyclobutyl. In some cases, $Z^2$ is a chemoselective functional group. In some cases, $Z^2$ is a linked modifying agent, wherein the modifying agent is selected from a heparin, a hyaluronic acid, a specific binding member, a peptide, a nucleic acid, gelatin, fibronectin, collagen, laminin, bFGF, EGF, insulin, progesterone, glucose, SDF thymosin beta-4, SHH, Noggin, Activin, TGFb3, FGF8, BDNF, GDNF, NT3, PDGF-AA and IGF-1.

In some embodiments of the first aspect, a thermoreversible polymer is described by formula (III):

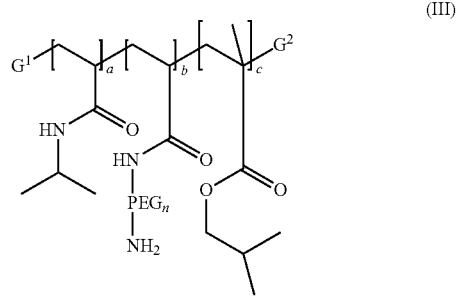

(III)

wherein $G^1$, $G^2$, $PEG_n$ and a-c are as described above. In some cases, a>0.8; 0.1>b>0; and 0.2>c>0.

In some embodiments of the first aspect, the thermoreversible polymer is described by the formula (IV):

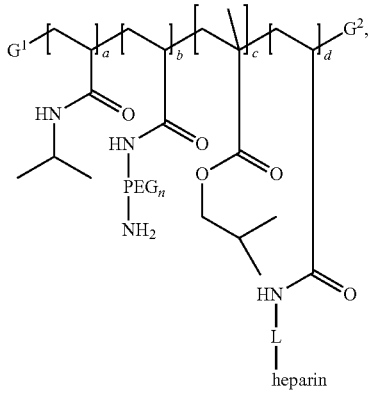

(IV)

wherein $G^1$, $G^2$, $PEG_n$, L and a-d are as described above. In some cases, $G^1$ and $G^2$ are each independently selected from a terminal group, a linker and a linked modifying agent. In some cases, $G^1$, $G^2$ or $Z^2$ comprise a linked hyaluronic acid that is linked via conjugation to the carboxylic acid group of a hyaluronic acid monomer. In some cases, $G^1$, $G^2$ or $Z^2$ comprise the following structure:

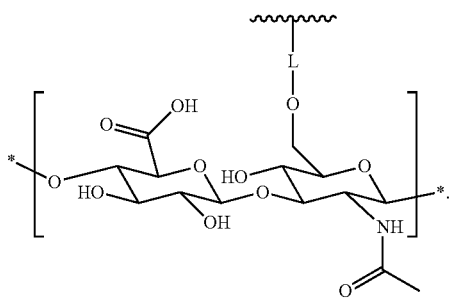

In some cases, $Z^2$ comprises the following structure:

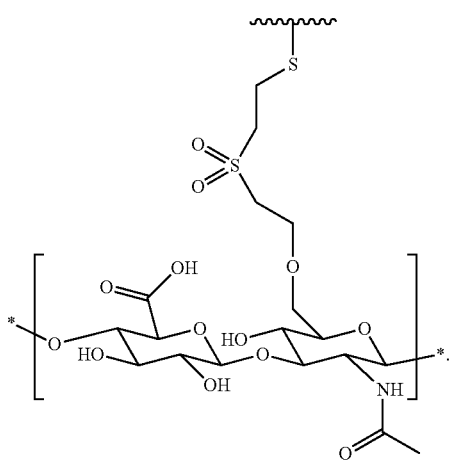

In some cases, $G^1$ and/or $G^2$ comprises the following structure:

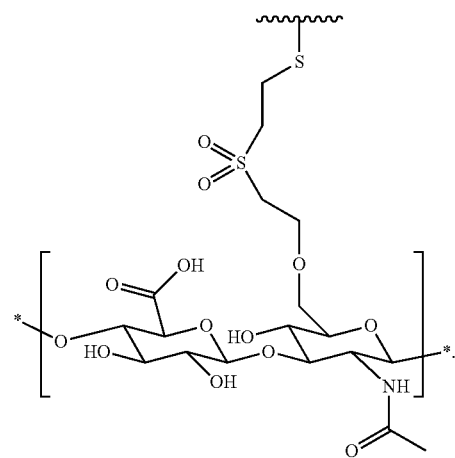

In some instances of the first aspect, e.g., of any of Formula I-IV, the polymer has a MW of 5 to 500 kDa. In some cases, the PEG or $PEG_n$ has a MW of 2 to 100 kDa.

In a second aspect, the present disclosure provides a hydrogel composition, comprising: a thermoreversible polymer as described above or elsewhere herein; and a buffered aqueous solution. In some cases, the hydrogel composition comprises cells. In some cases, the cells are stem cells selected from the group consisting of (a) adult stem cell derived from bone marrow, umbilical tissues, or placenta; (b) neural stem cell; (c) a progenitor cell derived from an embryonic stem cell; and (d) embryonic stem cell. In some cases, the thermoreversible polymer is a solid at 20° C. or more. In some cases, the thermoreversible polymer is a solid at 37° C. In some cases, the thermoreversible polymer is a liquid at 30° C. or less. In some cases, the thermoreversible polymer is a liquid at 4° C.

In a third aspect, the present disclosure provides a method of growing cells, the method comprising: introducing cells into a hydrogel composition of the second aspect as described above, or a hydrogel composition as described elsewhere herein, to produce a culturing mixture comprising a cell construct; and incubating the culturing mixture under conditions suitable for growth of the cells.

In a fourth aspect, the present disclosure provides a method of differentiating stem cells, the method comprising: introducing stem cells into a hydrogel composition of the second aspect as described above, or a hydrogel composition as described elsewhere herein, to produce a culturing mixture comprising a cell construct; and incubating the culturing mixture under conditions suitable for differentiation of the stem cells.

In a fourth aspect, the present disclosure provides a method of preparing a thermoreversible copolymer as described in the first aspect, above, or elsewhere herein, the method comprising: a) co-polymerizing: i) an alkyl methacrylate in which the alkyl is one of methyl, ethyl, propyl, butyl, pentyl, isopropyl, isobutyl, isopentyl, tert-butyl, cyclopropyl, and cyclobutyl; and ii) acrylic acid N-hydroxysuccinimide ester to make a copolymer comprising an acrylic backbone; b) contacting the copolymer with isopropylamine to convert a first portion of the N-hydroxysuccinimide ester groups to N-isopropylamine groups; and c) contacting the copolymer with a diamino-PEG to convert a second portion of the N-hydroxysuccinimide ester groups to N-PEG-$NH_2$ groups. In some cases, the method further comprises contacting the copolymer with an amino linker to convert a third portion of the N-hydroxysuccinimide ester groups to N-linker-$Z^2$ groups, where $Z^2$ is a chemoselective functional group.

BRIEF DESCRIPTION OF THE DRAWINGS

(FIG. 7A) at day 1; (FIG. 7B) at day 2; (FIG. 7C) at day 3; and (FIG. 7D) at day 4.

FIG. 8A-8C provides images of antibody stained cells for: (FIG. 8A) DAPI; (FIG. 8B) Nanog; and (FIG. 8C) Oct4; demonstrating the pluripotency of cells after growing in an exemplary hydrogels.

FIG. 24A: Example images of TCTF iPSCs and H1 hESCs staining positive for pluripotency markers Oct4 and Nanog, scale bars are 100 µm. FIG. 24B: Statistics on cells grown for 1-3 passages within the gels are >95% Oct4 and Nanog positive.

FIG. 26A-26C: Storage modulus at 37° C. (black squares) and LCST (grey triangles) as a function of HA molecular weight (FIG. 26A), PNIPAAm:HA ratio (FIG. 26B), Polymer concentration in solution (FIG. 26C). All error bars represent average storage modulus between 35-39° C. and concentrations are 10 w/v % unless otherwise noted. Panel A gels all were ~30% functionalized. FIG. 26C shows the same 1 MDa 40% HA-PNIPAAm gel at different concentrations.

FIG. 27A: Day 1 TCTF single cells FIG. 27B: Day 4 in $4^{th}$ round TCTF plated as single cells FIG. 27C. Day 4 H9 cells plated as single cells for 1 round FIG. 27D. Day 4 H1 cells plated as single cells for 1 round. Scale bars are all 200 µm.

FIG. 29A-29C depicts pluripotency markers Oct4 and Nanog for multiple cell lines (FIG. 29A) as well as expression of all three germ layers (FIG. 29B) by embryoid body differentiation analysis (FIG. 29C) after cells were grown for multiple passages within HA-PNIPAM hydrogels.

FIG. 30A-30D shows the growth of neural stem cells within HA-PNIPAM gels and stains for multipotency marker Sox2.

DEFINITIONS

Figure 1:
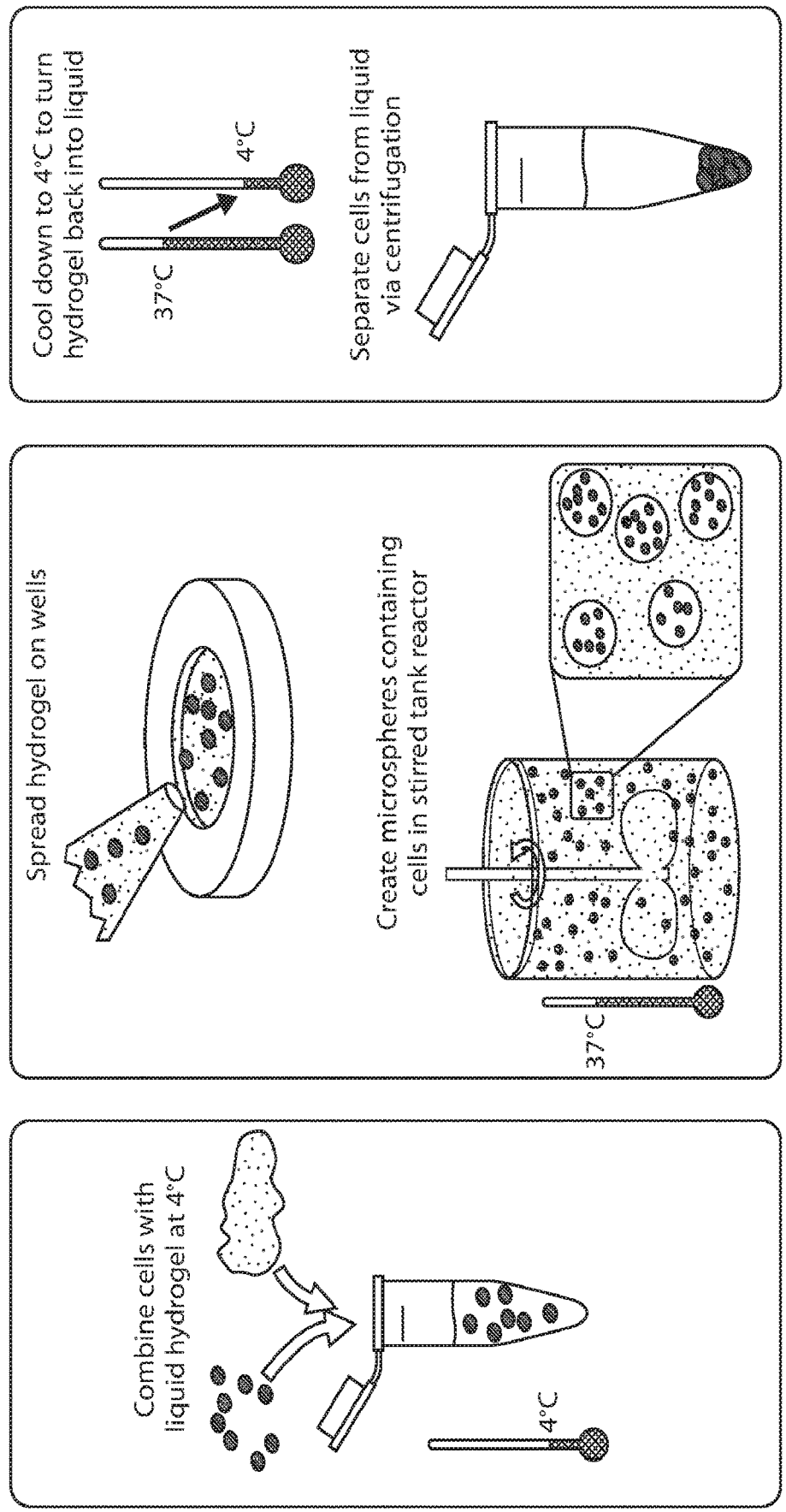
FIG. 1 depicts the steps of cell incorporation and removal from a thermoreversible polymer hydrogel.

The following terms have the following meanings unless otherwise indicated. Any undefined terms have their art recognized meanings.

The term "cell culture" or "culturing of cells" refers to maintaining, transporting, isolating, culturing, propagating, passaging or differentiating of cells or tissues. Cells can be in any arrangement such as individual cells, monolayers, cell clusters or spheroids or as tissue.

As used herein, the term "linker" or "linkage" refers to a linking moiety that connects two groups and has a backbone of 100 atoms or less in length. A linker or linkage may be a covalent bond that connects two groups or a chain of between 1 and 100 atoms in length, for example of 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, poly(ethylene glycol); ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. In some cases, a "lower alkyl" is an alkyl group having 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R and R may be the same or different and are chosen from hydrogen, optionally substituted alkyl, cycloalkyl, alkenyl, cycloalkenyl, alkynyl, aryl, heteroaryl and heterocyclic.

As used herein, the terms "chemoselective functional group" and "chemoselective tag" are used interchangeably and refer to chemoselective reactive groups that selectively react with one another to form a covalent bond. Chemoselective functional groups of interest include, but are not limited to, two thiol groups, thiols and maleimide or iodoacetamide, as well as groups that can react with one another via Click chemistry, e.g., azide and alkyne groups (e.g., cyclooctyne groups). Chemoselective functional groups of interest, include, but are not limited to, thiols, alkyne, a cyclooctyne, an azide, a phosphine, a maleimide, an alkoxyamine, an aldehyde and protected versions thereof, and percursors thereof. In certain embodiments, the chemoselective functional group is a thiol.

As used, herein the lower critical solution temperature (LCST) or lower consolute temperature refers to the critical temperature below which the components of a mixture are miscible for all compositions. The word lower in the term indicates that the LCST is a lower bound to a temperature interval of partial miscibility, or miscibility for certain compositions only.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a thermoreversible polymer" includes a plurality of such polymers and reference to "the hydrogel composition" includes reference to one or more hydrogel compositions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides thermoreversible polymers, hydrogel compositions comprising the thermoreversible polymers, as well as methods of making and using the thermoreversible polymers.

Thermoreversible Polymers

Aspects of the present disclosure include thermoreversible polymers (also referred to as "thermosensitive polymers" or "thermoresponsive polymers"). As used herein, the term "thermoreversible" is used to refer to a polymeric material that exhibits a drastic change in its physical property with a change in temperature. Thermoreversible polymers belong to the class of stimuli-responsive materials. In some cases, a thermoreversible polymer is distinguished from a temperature-sensitive (e.g., thermosensitive) material, which can change physical properties continuously with environmental conditions. A thermoresponsive polymer can display a miscibility gap in its temperature-composition diagram. Depending on whether the miscibility gap is found at high or low temperatures, an upper or lower critical solution temperature exists, respectively (abbreviated UCST or LCST, respectively). For example, at a temperature below the LCST, a thermoresponsive polymer can be miscible with an aqueous solution in which it dissolves. At a temperature above the LCST, the thermoresponsive polymer forms a solid, semi-solid, or gel having a three dimensional structure.

The subject thermoreversible polymers can include a polymer including N-isopropylacrylamide co-monomer, an alkyl [meth]acryl[ate/amide] co-monomer; and a PEG acrylamide co-monomer. As used herein, the term "an alkyl [meth]acryl[ate/amide] co-monomer" refers to a co-monomer that is an alkyl acrylate, an alkyl methacrylate, an alkyl acrylamide or an alkyl methacrylamide. In some instances, the alkyl [meth]acryl[ate/amide] co-monomer is an isobutyl methacrylate co-monomer.

As used herein, the term PEG acrylamide co-monomer refers to a N-alkyl acrylamide further substituted on the alkyl sidechain with a polyethylene glycol (PEG) or modified polyethylene glycol. In some cases, a PEG polymeric group includes water-soluble repeat units comprising an ethylene oxide of the formula —($CH_2$—$CH_2$—O)— or —(O—$CH_2$—$CH_2$)—. The number of such water-soluble repeat units can vary significantly, with the number of such units being from 2 to 500, 2 to 400, 2 to 300, 2 to 200, 2 to 100, for example from 2 to 50. A modified PEG can include any convenient terminal modifications, such as substitution or modification with a linked functional group such as an amine, a thiol or a carboxylic acid, e.g., capable of conjugation with a modifying agent of interest.

In some embodiments, the thermoreversible polymer further comprises a modifying acryl[ate/amide] co-monomer comprising a linked functional group or a linked modifying agent. As used herein, by modifying acryl[ate/amide] co-monomer is meant a substituted alkyl acrylate or a substituted N-alkyl acrylamide co-monomer, which can be substituted with an optional linker terminated with a functional group and/or a linked modifying agent. In certain embodiments, the thermoreversible polymer lacks a PEG acrylamide co-monomer.

In some embodiments, the thermoreversible polymer comprises a polymeric segment described by formula (I):

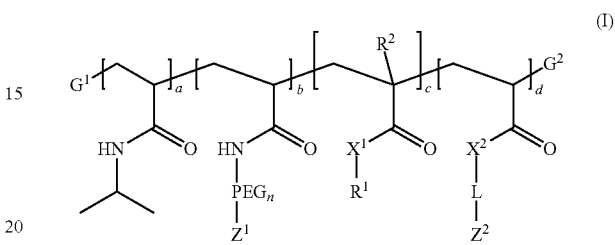

wherein:
a, b, c and d are molar fractions of the co-monomers (e.g., in some cases, a and c are each greater than 0);
$PEG_n$ is a polyethylglycol polymer;
$Z^1$ is an optional terminal functional group or a linked modifying agent;
$Z^2$ is a functional group or a linked modifying agent;
L is a linker;
$X^1$ and $X^2$ are each independently O or NH;
$R^1$ is an alkyl or a substituted alkyl (e.g., a lower alkyl or a substituted lower alkyl);
$R^2$ is H or methyl; and
$G^1$ and $G^2$ are each independently selected from a polymer segment, a terminal group, a linker and a linked modifying agent (e.g., a hyaluronic acid).

As used here, the term "modifying agent" refers to any convenient agent that provides for a desirable property of interest (e.g., a desirable physical and/or biological property) and which is capable of conjugation to the thermoreversible polymer, e.g., via a chemoselective functional group on a sidechain linker or terminal of the polymer. Such an agent may belong to the class of small molecule, protein, peptide, sugar, polynucleotide, etc. Modifying agents of interest include, but are not limited to, a ligand, a substrate, an enzyme, a pharmaceutical agent (e.g., a chemotherapeutic agent), a plasmid, a polynucleotide, a bioactive peptide, an antibody, a biomarker, a bio-sensor, a catalyst, an element, a cell targeting agent, small drug molecules, fluorescent/radioactive/optical imaging agents, peptides/proteins/enzymes, nucleic acids (siRNA/RNA/DNA/etc.), metal based compounds/catalysts, site-specific cellular targeting agents (compounds/ligands/antibodies/etc.) and smart adjuvants, gene therapy vectors. In certain embodiments, the modifying agent is selected from a heparin, a hyaluronic acid, a specific binding member, a peptide, a nucleic acid, gelatin, fibronectin, collagen, laminin, bFGF, EGF, insulin, progesterone, glucose, thymosin beta-4, SHH, Noggin, Activin, TGFb3, FGF8, BDNF, GDNF, NT3, PDGF-AA and IGF-1. In certain instances, the modifying agent is a cytokine, a BMP family member (e.g., TGFbeta or activin), a neutrophin (e.g., NT3 or BDNF) or a hedgehog protein (e.g., SHH).

Figure 19:
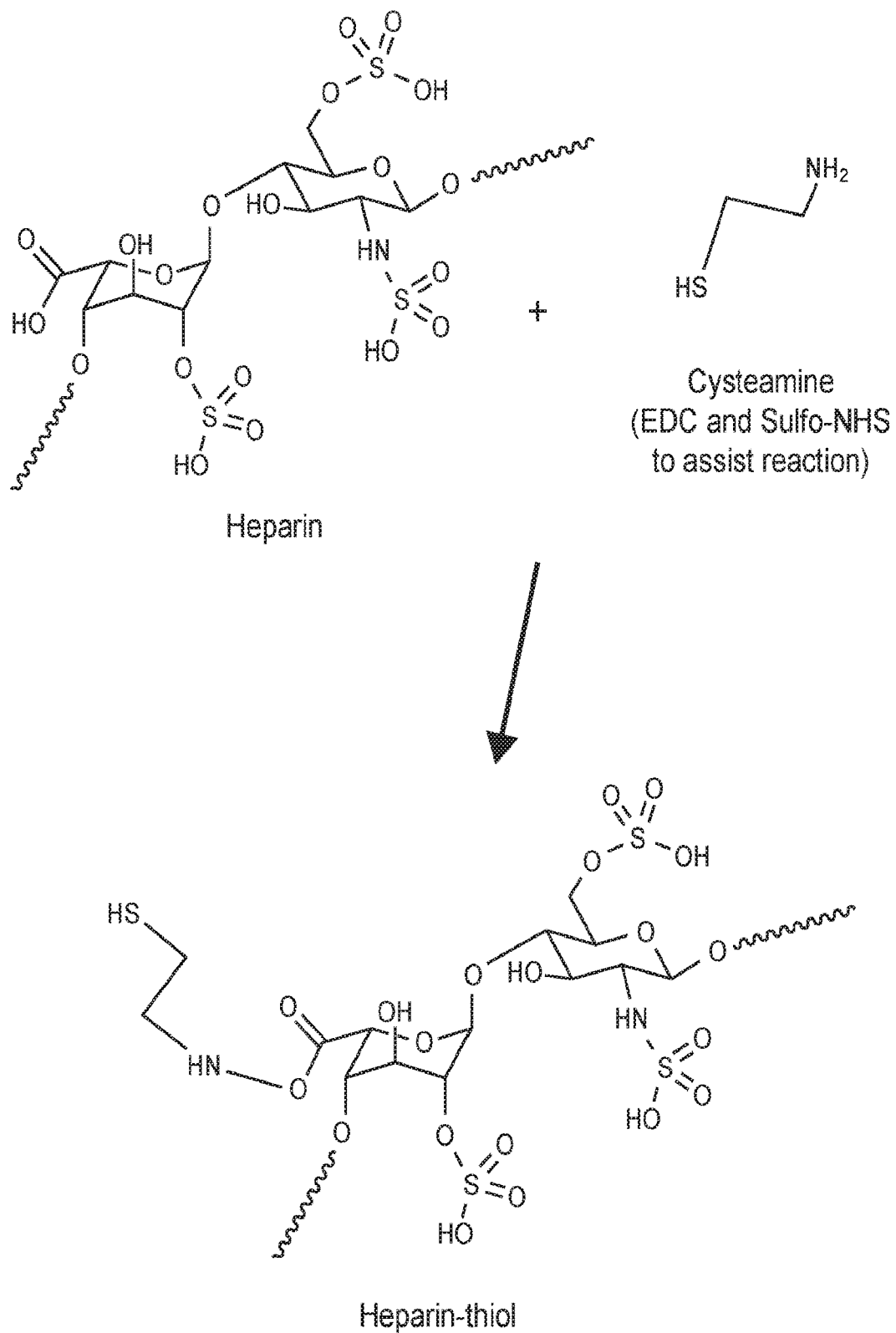
FIG. 19 depicts an exemplary scheme for heparin addition to hyaluronic acid.
Figure 19:
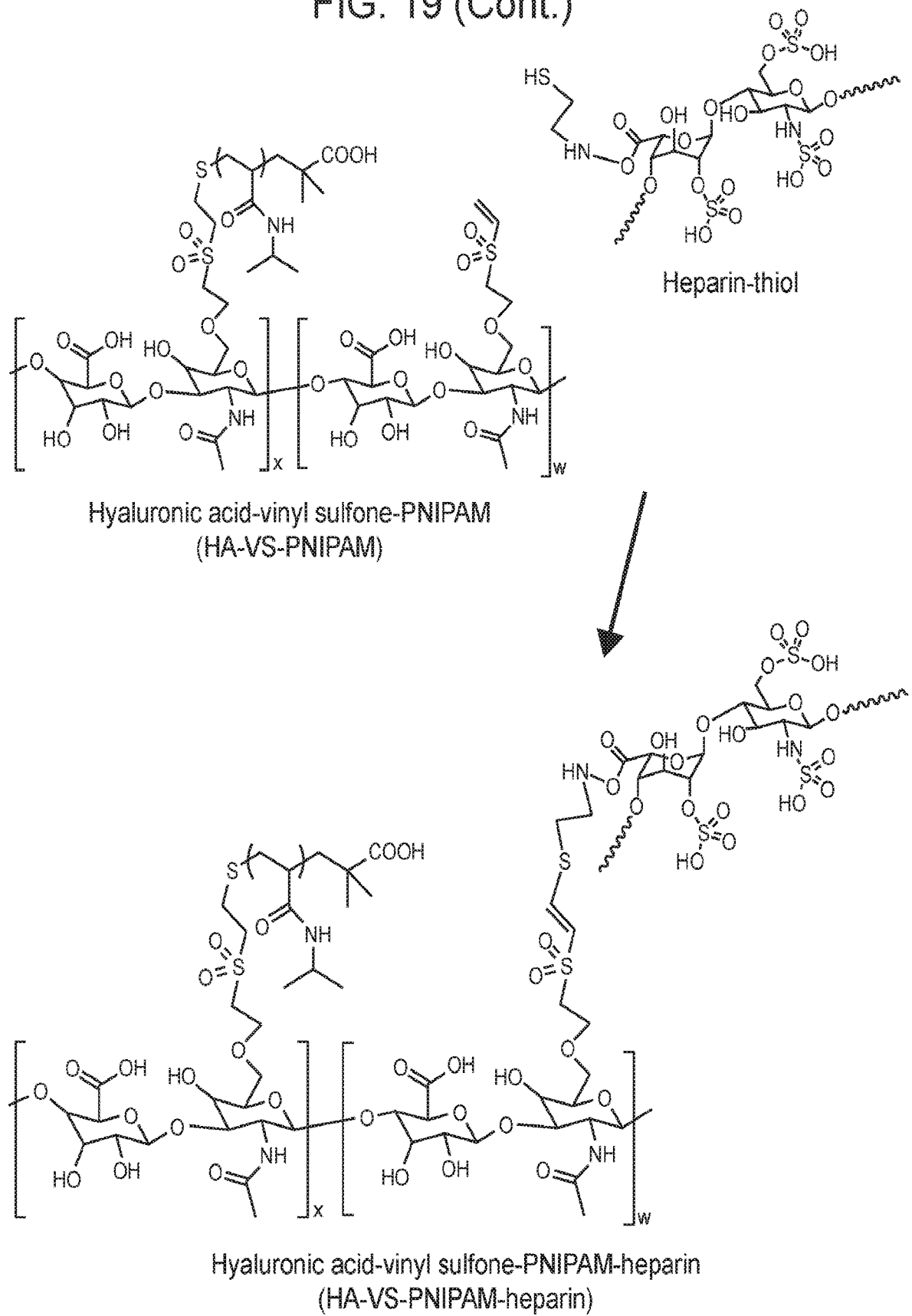

Any convenient methods may be utilized in conjugating a modifying agent to a thermoreversible polymer. Conjugation methods and chemistries of interest include, but are not limited to, those described by Greg Hermanson in Bioconjugate Techniques (Third edition) 2013, Academic Press. In certain embodiments, the modifying agent is a protein. In certain embodiments, the modifying agent is a peptide. In certain embodiments, the modifying agent is peptidic and can be conjugated to the thermoreversible polymer (e.g., via a terminal and/or a sidechain functional group) by covalent attachment to the N-terminal or C-terminal or the peptidic agent, or covalent attachment to an amino acid sidechain (e.g., an amino, thiol, hydroxyl, carboxylic acid or phenol-containing amino acid sidechain group, or a derivative thereof). In certain embodiments, the modifying agent is a heparin. In certain embodiments, the heparin modifying agent is linked via a vinvylsulfone/thiol linkage. In certain instances, the heparin can be linked to the subject polymers via conjugation to a carboxylic acid group of the heparin. For example, FIG. 19 depicts exemplary methods of preparing a heparin-thiol derivative and a hyaluronic acid-vinyl sulfone derivative that finds use in conjugation to the subject thermoreversible polymer. In certain embodiments, heparin can be attached via an amine group of the thermoreversible polymer. In certain embodiments, two or more modifying agents (e.g., a heparin and a hyaluronic acid) may be linked to each other in addition to a thermoreversible polymer.

In some embodiments of formula (I), b is 0. In some embodiments of formula (I), b>0. In some embodiments of formula (I), b<0.5. In some embodiments of formula (I), b<0.4. In some embodiments of formula (I), b<0.3. In some embodiments of formula (I), b<0.2. In some embodiments of formula (I), b<0.1. In some embodiments of formula (I), 0<b<0.1. In some embodiments of formula (I), 0<b<0.05. In some embodiments of formula (I), 0<b<0.02.

In some embodiments of formula (I), d is 0. In some embodiments of formula (I), d>0. In some embodiments of formula (I), d<0.5. In some embodiments of formula (I), d<0.4. In some embodiments of formula (I), d<0.3. In some embodiments of formula (I), d<0.2. In some embodiments of formula (I), d<0.1. In some embodiments of formula (I), 0<d<0.1. In some embodiments of formula (I), 0<d<0.05.

In some embodiments of formula (I), a>0.3. In some embodiments of formula (I), a>0.4. In some embodiments of formula (I), a>0.5. In some embodiments of formula (I), a>0.6. In some embodiments of formula (I), a>0.7. In some embodiments of formula (I), a>0.8. In some embodiments of formula (I), a>0.9.

In some embodiments of formula (I), c>0.1. In some embodiments of formula (I), c>0.2. In some embodiments of formula (I), c>0.3. In some embodiments of formula (I), c<0.3. In some embodiments of formula (I), c<0.2. In some embodiments of formula (I), 0<c<0.2. In some embodiments of formula (I), 0<c<0.15. In some embodiments of formula (I), c=0.

In some embodiments of formula (I), a>0.9, 0<b<0.02, 0<c<0.2 and 0<d<0.05.

In some embodiments of formula (I), a>0.95. In some embodiments of formula (I), 0<b<0.01. In some embodiments of formula (I), 0<c<0.1. In some embodiments of formula (I), 0<d<0.03. In some embodiments of formula (I), a>0.95, 0<b<0.01, 0<c<0.1 and 0<d<0.03.

In some embodiments of formula (I), a>0.95, 0<b<0.01, 0<c<0.07 and 0<d<0.02. In some embodiments of formula (I), a>0.95. In some embodiments of formula (I), 0<b<0.01. In some embodiments of formula (I), 0<c<0.07. In some embodiments of formula (I), 0<d<0.02.

Any convenient poly(ethylglycol) (PEG) polymeric groups may be utilized as a sidechain in the thermoreversible polymers of Formula (I). In some embodiments of formula (I), $PEG_n$ is a polyethylglycol polymer having a MW of 2 kDa or greater, such as 2 kDa to 100 kDa, or 2 kD to 10 kDa, or 3 kDa to 10 kDa, such as 3400 Da. The $PEG_n$ group can be modified with any convenient groups, including terminal modifications. In some instances, the $PEG_n$ group is modified with a terminal group $Z^1$. In some embodiments, $PEG_n$ includes a terminal carboxylic acid. In some embodiments, $PEG_n$ includes a terminal amine group. In some embodiments, $Z^1$ is a linked modifying agent (e.g., as described herein).

Any convenient chemoselective functional groups capable of conjugation with a compatible functional group on another moiety of interest may find use as terminal group $Z^2$ in the subject a modifying acryl[ate/amide] co-monomer. In some embodiments, $Z^2$ is a functional group selected from an amino, a thiol, a carboxylic acid, a maleimide, a vinyl sulfone, a haloacetyl, an azide, an alkyne (e.g., a cyclooctyne), and protected versions thereof. In some embodiments of formula (I), $Z^2$ is a thiol. In some embodiments of formula (I), $Z^2$ is an azide. In some embodiments of formula (I), $Z^2$ is a maleimide. A variety of methods and reagents may find use in conjugating a modifying agent of interest to the terminal of a $PEG_n$ sidechain group. In some embodiments, $Z^2$ is a linked modifying agent (e.g., as described herein). In some embodiments, heparin can be conjugated to an amine group of the PEG side chain in the thermoreversible polymer.

Any convenient linkers may be utilized in the subject thermoreversible polymers. In certain embodiments, the linker (L) includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol. Linkers of interest include, but are not limited to, units of polymers such as polyethylene glycols, polyethylenes and polyacrylates, amino acid residue(s), carbohydrate-based polymers or carbohydrate residues and derivatives thereof, polynucleotides, alkyl groups, aryl groups, heterocycle groups, cleavable linker groups, combinations thereof, and substituted versions thereof.

In some embodiments, the linker includes a cleavable moiety (e.g., a chemically cleavable moiety, an enzymatically cleavable moiety (such as, but not limited to, a protease cleavable moiety, a glucuronidase cleavable moiety, a beta-lactamase cleavable moiety, etc.), a photocleavable moiety, and the like. In certain embodiments, the cleavable moiety is a para-amino-benzyloxycarbonyl group, a meta-amino-benzyloxycarbonyl group, a para-amino-benzyloxy group, a meta-amino-benzyloxy group, para-aminobenzyl, an acetal group, a disulfide, a hydrazine, a protease-cleavable moiety, a glucuronidase cleavable moiety, a beta-lactamase cleavable moiety, or an ester.

In some embodiments of formula (I), $R^1$ is a lower alkyl or a substituted lower alkyl. In some embodiments of formula (I), $R^1$ is a lower alkyl selected from the group consisting of methyl, ethyl, propyl, butyl, pentyl, isopropyl, isobutyl, isopentyl, tert-butyl, cyclopropyl, and cyclobutyl. In certain embodiments, $R^1$ is methyl. In certain embodiments, $R^1$ is ethyl. In certain embodiments, $R^1$ is propyl. In certain embodiments, $R^1$ is butyl. In certain embodiments, $R^1$ is pentyl. In certain embodiments, $R^1$ is isopropyl. In certain embodiments, $R^1$ is isobutyl. In certain embodiments, $R^1$ is isopentyl. In certain embodiments, $R^1$ is tert-butyl. In certain embodiments, $R^1$ is cyclopropyl. In certain embodiments, $R^1$ is cyclobutyl.

In some embodiments of formula (I), $R^2$ is H. In some embodiments of formula (I), $R^2$ is methyl.

In some embodiments of formula (I), $G^1$ and/or $G^2$ are each independently a further polymer segment, such as a polyacrylic acid or polyacrylamide polymer. In certain cases of formula (I), $G^1$ and/or $G^2$ are each independently a terminal group, e.g., H, an alkyl or a substituted alkyl. In certain cases, the terminal groups are groups which are produced as a result of any convenient method of polymerization of the subject co-monomers described herein. In some embodiments of formula (I), $G^1$ and/or $G^2$ comprise a linker that may include a chemoselective functional group. In some embodiments of formula (I), $G^1$ and/or $G^2$ comprise a linked modifying agent (e.g., as described herein). Any convenient methods of derivatizing or modifying polymers may be utilized to provide for installation of a $G^1$ and/or $G^2$ group of interest at the terminals of the subject polymers. In certain cases, $G^1$ and/or $G^2$ group comprises a linked modifying agent (e.g., a hyaluronic acid).

In some embodiments, the thermoreversible polymer comprises a polymeric segment described by formula (II):

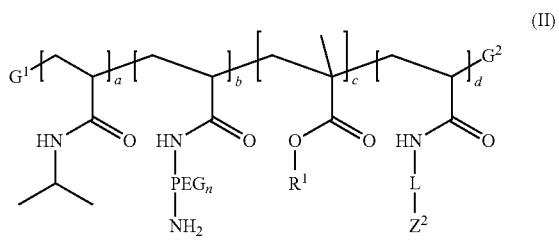

(II)

wherein $G^1$, $G^2$, $PEG_n$, $R^1$, L, $Z^2$ and a-d are as described for formula (I).

In some embodiments, the thermoreversible polymer is described by formula (I) or (II).

In some embodiments of formula (II), d is 0. In some embodiments of formula (II), a>0.8. In some embodiments of formula (II), 0.1>b>0. In some embodiments of formula (II), c<0.2. In some embodiments of formula (II), a>0.8; 0.1>b>0 and c<0.2.

In some embodiments of formula (II), b>0. In some embodiments of formula (II), b<0.5. In some embodiments of formula (II), b<0.4. In some embodiments of formula (II), b<0.3. In some embodiments of formula (II), b<0.2. In some embodiments of formula (II), b<0.1. In some embodiments of formula (II), 0<b<0.1. In some embodiments of formula (II), 0<b<0.05. In some embodiments of formula (II), 0<b<0.02.

In some embodiments of formula (II), d is 0. In some embodiments of formula (II), d>0. In some embodiments of formula (II), d<0.5. In some embodiments of formula (II), d<0.4. In some embodiments of formula (II), d<0.3. In some embodiments of formula (I), d<0.2. In some embodiments of formula (II), d<0.1. In some embodiments of formula (II), 0<d<0.1. In some embodiments of formula (II), 0<d<0.05.

In some embodiments of formula (II), a>0.3. In some embodiments of formula (II), a>0.4. In some embodiments of formula (II), a>0.5. In some embodiments of formula (II), a>0.6. In some embodiments of formula (II), a>0.7. In some embodiments of formula (II), a>0.8. In some embodiments of formula (II), a>0.9.

In some embodiments of formula (II), c>0.1. In some embodiments of formula (II), c>0.2. In some embodiments of formula (II), c>0.3. In some embodiments of formula (I), c<0.3. In some embodiments of formula (II), c<0.2. In some embodiments of formula (I), 0<c<0.2. In some embodiments of formula (II), 0<c<0.15.

In some embodiments of formula (II), a>0.9, 0<b<0.02, 0<c<0.2 and 0<d<0.05.

In some embodiments of formula (II), $R^1$ is a lower alkyl or a substituted lower alkyl. In some embodiments of formula (II), $R^1$ is a lower alkyl selected from the group consisting of methyl, ethyl, propyl, butyl, pentyl, isopropyl, isobutyl, isopentyl, tert-butyl, cyclopropyl, and cyclobutyl. In certain embodiments, $R^1$ is methyl. In certain embodiments, $R^1$ is ethyl. In certain embodiments, $R^1$ is propyl. In certain embodiments, $R^1$ is butyl. In certain embodiments, $R^1$ is pentyl. In certain embodiments, $R^1$ is isopropyl. In certain embodiments, $R^1$ is isobutyl. In certain embodiments, $R^1$ is isopentyl. In certain embodiments, $R^1$ is tert-butyl. In certain embodiments, $R^1$ is cyclopropyl. In certain embodiments, $R^1$ is cyclobutyl.

In some embodiments of formula (II), $Z^2$ is a functional group selected from an amino, a thiol, a carboxylic acid, a maleimide, a vinyl sulfone, a haloacetyl, an azide, an alkyne (e.g., a cyclooctyne), and protected versions thereof. In some embodiments of formula (II), $Z^2$ is a thiol. In some embodiments of formula (II), $Z^2$ is an azide. In some embodiments of formula (II), $Z^2$ is a maleimide. In some embodiments of formula (II), $Z^2$ is a linked modifying agent (e.g., as described herein). In certain instances of formula (I) or (II), $Z^2$ is a linked modifying agent selected from a heparin, a hyaluronic acid, a specific binding member, a peptide, a nucleic acid, gelatin, fibronectin, collagen, laminin, basic fibroblast growth factor (bFGF), epidermal growth factor (EGF), insulin, progesterone, glucose, a stromal cell-derived factor (SDF) (e.g., SDF-1), thymosin beta-4, a sonic hedgehog (SHH) polypeptide, Noggin, Activin, a transforming growth factor (TGF) (e.g., TGFb3), a fibroblast growth factor (FGF) (e.g., FGF8), brain-derived neurotrophic factor (BDNF), glial cell-derived neurotrophic factor (GDNF), a neutrophin (NT) (e.g., NT3), a platelet-derived growth factor (PDGF) (e.g., PDGF-AA), and insulin-like growth factor (IGF) (e.g., IGF-1). In certain instances of formula (I) or (II), $Z^2$ is a linked modifying agent that is a cytokine, a bone morphogenetic protein (BMP) family member (e.g., TGF-beta or activin), a neutrophin (e.g., NT3 or BDNF) or a hedgehog protein (e.g., SHH).

In some embodiments, the thermoreversible polymer comprises a polymeric segment described by formula (III):

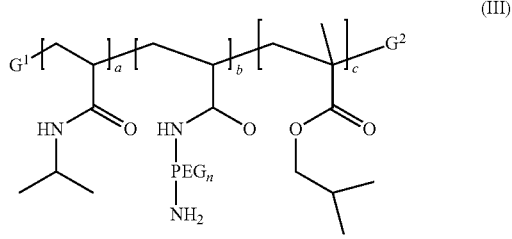

(III)

wherein $G^1$, $G^2$, $PEG_n$ and a-c are as described in formulae (I) and (II).

In some embodiments of formula (III), a>0.8. In some embodiments of formula (III), a>0.9. In some embodiments of formula (III), 0.1>b>0. In some embodiments of formula (III), 0.02>b>0. In some embodiments of formula (III), 0.2>c>0. In some embodiments of formula (III), 0.15>c>0. In some embodiments of formula (III), a>0.9; 0.02>b>0 and 0.15>c>0. In some embodiments of formula (III), a>0.8; 0.1>b>0 and 0.2>c>0.

In some embodiments of formula (III), b>0. In some embodiments of formula (III), b<0.5. In some embodiments of formula (III), b<0.4. In some embodiments of formula (III), b<0.3. In some embodiments of formula (III), b<0.2. In some embodiments of formula (III), b<0.1.

In some embodiments of formula (III), a>0.3. In some embodiments of formula (III), a>0.4. In some embodiments of formula (III), a>0.5. In some embodiments of formula (III), a>0.6. In some embodiments of formula (III), a>0.7.

In some embodiments of formula (III), c<0.1. In some embodiments of formula (III), c<0.2. In some embodiments of formula (III), c<0.3. In some embodiments of formula (III), c<0.4. In some embodiments of formula (III), c<0.5.

In some embodiments of formula (III), $PEG_n$ is a polyethylglycol polymer having a MW of 3 kDa or greater, such as 3 kDa to 100 kDa or 3 kD to 10 kDa, such as 3400 Da.

In some embodiments, the thermoreversible polymer comprises a polymeric segment described by formula (IV):

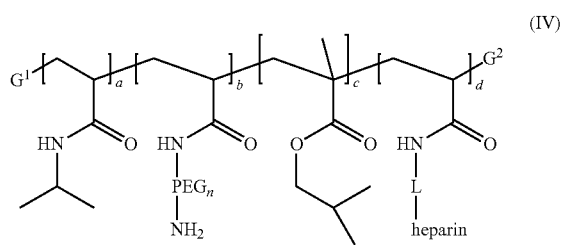

(IV)

wherein $G^1$, $G^2$, $PEG_n$, L and a-d are as described in formula (I)-(III). In some embodiments, the thermoreversible polymer is described by formula (IV).

In certain embodiments of any one of formulae (I)-(IV), $G^1$ and $G^2$ are each independently selected from a terminal group, a linker and a linked modifying agent.

In certain embodiments of any one of formulae (I)-(IV), $G^1$, $G^2$ and/or $Z^2$ comprise the following structure:

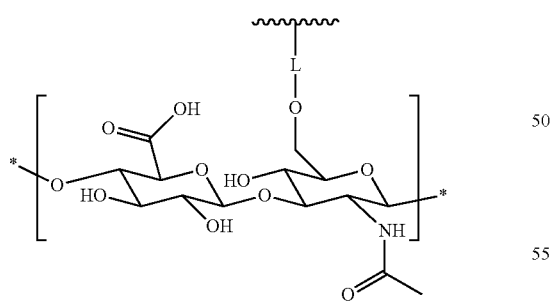

where the brackets and "*" represent that the monomer structure depicted can be a polymeric hyaluronic acid of any convenient number of monomeric units; and L is a linker. In certain instances, the subject thermoreversible polymers include a linked hyaluronic acid (e.g., linked via a terminal or a sidechain linker). In certain instances, conjugation to a linked hyaluronic acid is achieved using thiol/vinyl sulfone, thiol/maleimide, thiol/iodacetamide, thiol/haloacetyl or azide/alkyne conjugation chemistry. In certain instances, conjugation to a linked hyaluronic acid is achieved using α-halocarbonyls, Michael acceptors, β-haloethylamines, or any α,β-unsaturated systems. The hyaluronic acid itself may include a variety of conjugation sites to a variety of polymers of interest. In certain cases, the hyaluronic acid itself includes a plurality of linkages to one or more moieties of interest, including one or more of the subject thermoreversible polymers. In certain instances, the thermoreversible polymer includes multiple linkages to a hyaluronic acid of interest.

The linked hyaluronic acid can be of any convenient molecular weight. In some embodiments, the linked hyaluronic acid itself has a MW of 100 kDa or more, such as 200 kDa or more, 300 kDa or more, 400 kDa or more, 500 kDa or more, 600 kDa or more, 700 kDa or more, 800 kDa or more, 900 kDa or more, 1 MDa or more, or even more. In some embodiments, the linked hyaluronic acid itself has a MW of 100 kDa to 1 MDa, such as 200 kDa to 1 MDa, 300 kDa to 1 MDa, 400 kDa to 1 MDa, or 500 kDa to 1 MDa.

In certain instances, the ratio of hyaluronic acid to thermoreversible polymer in the resulting conjugate structure may be in the range of 1:10 to 1:1.25 by weight, such as about 1:10, about 1:5, about 1:2.5 or about 1:1.25.

In certain embodiments of formulae (I)-(II), $Z^2$ comprises the following structure:

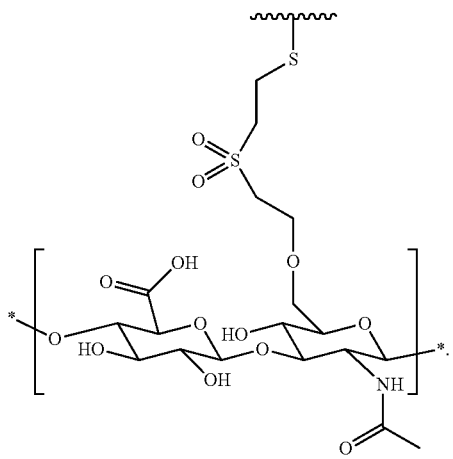

In certain embodiments of formulae (I)-(IV), $G^1$ and/or $G^2$ comprise the following structure:

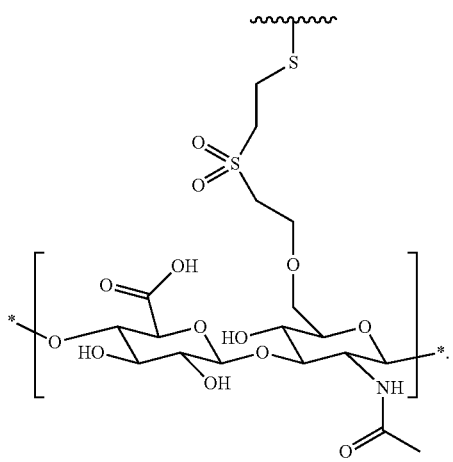

The subject thermoreversible polymers may have any convenient MW. In certain embodiments, the thermoreversible polymer has a MW of 500 kDa or less, such as 400 kDa or less, 300 kDa or less, 250 kDa or less, 200 kDa or less, 150 kDa or less, 100 kDa or less, 90 kDa or less, 80 kDa or less, 70 kDa or less, 60 kDa or less, or even 50 kDa or less. In certain embodiments, the thermoreversible polymer has a MW in the range or 50 kDa to 300 kDa, such as 50 kDa to 250 kDa, 50 kDa to 200 kDa, 50 kDa to 150 kDa, or 50 kDa to 100 kDa. In certain embodiments, the thermoreversible polymer has a MW of 5 kDa or more. In certain embodiments, the thermoreversible polymer has a MW of 5 kDa to 500 kDa.

In some embodiments, the thermoreversible polymer has a loss modulus when in solid or gel form of 100 Pa or more, such as 200 Pa or more, 300 Pa or more, 400 Pa or more, 500 Pa or more, 600 Pa or more, 700 Pa or more, 800 Pa or more, 900 Pa or more, 1000 Pa or more, 2000 Pa or more, 3000 Pa or more, 4000 Pa or more, 5000 Pa or more, or even more. In certain instances, the loss modulus is measured at 37° C.

In some embodiments, the thermoreversible polymer has a storage modulus when in solid or gel form of 50 Pa or more, 100 Pa or more, such as 200 Pa or more, 300 Pa or more, 400 Pa or more, 500 Pa or more, 600 Pa or more, 700 Pa or more, 800 Pa or more, 900 Pa or more, 1000 Pa or more, 2000 Pa or more, 3000 Pa or more, 4000 Pa or more, 5000 Pa or more, or even more. In certain instances, the storage modulus is measured at 37° C. In certain instances, increasing the molecular weight of hyaluronic acid increases the storage modulus of the thermoreversible polymer. In certain instances, increasing the molecular weight of PEG for copolymers containing isobutyl methacrylate and butyl methacrylate increases the storage modulus of the thermoreversible polymer. In certain instances, increasing the polymer concentration increases the storage modulus of the thermoreversible polymer. In certain instances, increasing the alkyl chain of between methyl, ethyl, and isobutyl methacrylate increases the storage modulus of the thermoreversible polymer.

Compositions

The present disclosure provides a composition including two or more thermoreversible polymers of the present disclosure. In some embodiments, the composition includes a mixture of a low MW thermoreversible polymer (e.g., having a MW of 100 kDa or less, such as 75 kDa or less, or 50 kDa or less) and a high MW thermoreversible polymer (e.g., having a MW of 100 kDa or more, such as 200 kDa or more, 300 kDa or more, 500 kDa or more, or even more).

Aspects of the present disclosure include a hydrogel composition including a thermoreversible polymer and an aqueous solution. When the hydrogel composition is below its sol-gel transition temperature, the composition can be a homogeneous solution, such that any cells that are present in the solution may be easily removed (e.g., by centrifugation). When the hydrogel composition is above its sol-gel transition temperature, the thermoreversible polymer provides a three-dimensional matrix that finds use in the incubation, growth and/or differentiation of cells of interest.

Any convenient buffered aqueous solutions that find use in the incubation and/or differentiation of cells of interest may be utilized in the subject hydrogel compositions. The buffered aqueous solution may include any convenient components of interest.

In some instances, the hydrogel composition further includes cells of interest (e.g., as described herein). In certain embodiments, the hydrogel composition includes stem cells selected from the group consisting of (a) adult stem cell derived from bone marrow, umbilical tissues, or placenta; (b) neural stem cell; and (c) embryonic stem cell.

In certain instances, the thermoreversible polymer is a solid, semi-solid, or gel at 20° C. or more, such as 21° C. or more, 22° C. or more, 23° C. or more, 24° C. or more, 25° C. or more, 26° C. or more, 27° C. or more, 28° C. or more, 29° C. or more, 30° C. or more, 31° C. or more, 32° C. or more, 33° C. or more, 34° C. or more, 35° C. or more, 36° C. or more, or even more. In certain embodiments, the thermoreversible polymer is a solid at 37° C.

In certain instances, the thermoreversible polymer (e.g., a thermoreversible polymer of Formula I, Formula II, Formula III, or Formula IV) is a solid, semi-solid, or gel at 10° C. or more, or 15° or more. In certain instances, the thermoreversible polymer (e.g., a thermoreversible polymer of Formula I, Formula II, Formula III, or Formula IV) is a solid, semi-solid, or gel at a temperature of from 10° C. to 15° C., from 15° C. to 20° C., or 20° C. to 25° C. In some cases, the thermoreversible polymer (e.g., a thermoreversible polymer of Formula I, Formula II, Formula III, or Formula IV) is a solid, semi-solid, or gel at a temperature of from 10° C. to 15° C.

In some embodiments, the thermoreversible polymer is a liquid at 30° C. or less, such as 25° C. or less, 20° C. or less, 18° C. or less, 16° C. or less, 14° C. or less, 12° C. or less, 10° C. or less, 8° C. or less, 6° C. or less, or 4° C. or less. In certain embodiments, the thermoreversible polymer is a liquid at less than 20° C. In certain embodiments, the thermoreversible polymer is a liquid at 4° C.

In some cases, a thermoreversible polymer (e.g., a thermoreversible polymer of Formula I, Formula II, Formula III, or Formula IV) has a sol-gel transition temperature or LCST in the range of 5-35° C., such as 10-35° C., 10-30° C., 10-25° C. or 10-20° C. In some cases, a thermoreversible polymer (e.g., a thermoreversible polymer of Formula I, Formula II, Formula III, or Formula IV) has an LCST in the range of 10° C. to about 15° C.

The subject thermoreversible polymers can be prepared using any convenient methods. A variety of polymerization methods may be utilized in preparing a base polymeric material, e.g., including polyacrylate, polyacrylamide and mixtures thereof. A variety of derivatization methods may be utilized to introduce any convenient functionality into the subject base polymeric materials. A variety of chemoselective conjugation chemistries, linkers, functional groups and modifying agents may be utilized in the preparation of further derivatives and conjugates of the subject base polymeric materials and derivatives thereof. For example, any of the methods depicted in FIG. 3, FIG. 9, FIG. 10, FIG. 12, FIG. 13, FIG. 14, FIG. 16 and FIG. 19 may be adapted for use in preparing the subject thermoreversible polymers.

Thermoreversible Polymer-Cell Compositions

The present disclosure provides a composition comprising: a) a thermoreversible polymer of the present disclosure; and b) cells embedded or suspended within the polymer. A thermoreversible polymer-cell composition of the present disclosure is useful for generating a desired number of cells, by culturing the thermoreversible polymer-cell composition under conditions and for a period of time sufficient to generate the desired number of cells. Such cells can include stem cells, differentiated cells, and the like. A thermoreversible polymer-cell composition of the present disclosure is useful for differentiating cells, e.g., to generate a desired number of differentiated cells. A thermoreversible polymer-cell composition of the present disclosure can be implanted into an individual in need thereof, where cells proliferate and/or differentiated within the implanted thermoreversible polymer-cell composition, and migrate out of the implanted thermoreversible polymer-cell composition.

Methods for Culturing Cells

A thermoreversible polymer of the present disclosure can be used to culture cells in vitro or in vivo. Thus, the present disclosure provides methods of culturing cells, the methods involving contacting the cells with the thermoreversible polymer; and culturing the cell-containing thermoreversible polymer under conditions suitable for growth and/or differentiation of the cells. In some cases, a method of the present disclosure comprises culturing cells contained within (e.g., embedded in; suspended in; etc.) a hydrogel composition of the present disclosure.

In some cases, a method of the present disclosure for culturing cells comprises culturing the cells in a hydrogel composition of the present disclosure at a temperature (e.g., from about 30° C. to about 37° C.; e.g., at 37° C.) at which the hydrogel composition is a semi-solid (e.g., a gel). In some cases, a method of the present disclosure for culturing cells comprises culturing the cells in a hydrogel composition of the present disclosure at a temperature (e.g., from about 4° C. to about 10° C.; e.g., at 4° C.) at which the hydrogel composition is a liquid.

A method of the present disclosure for culturing cells can be used to generate a desired number of cells, including differentiated cells and stem cells. For example, a method of the present disclosure can be used to generate from $10^2$ cells to about $10^9$ cells, e.g., from about $10^2$ cells to about $5 \times 10^2$ cells, from about $5 \times 10^2$ cells to about $10^3$ cells, from about $10^3$ cells to about $5 \times 10^3$ cells, from about $5 \times 10^3$ cells to about $10^4$ cells, from about $10^4$ cells to about $5 \times 10^4$ cells, from about $5 \times 10^4$ cells to about $10^5$ cells, from about $10^5$ cells to about $5 \times 10^5$ cells, from about $5 \times 10^5$ cells to about $10^6$ cells, from about $10^6$ cells to about $5 \times 10^6$ cells, from about $5 \times 10^6$ cells to about $10^7$ cells, from about $10^7$ cells to about $5 \times 10^7$ cells, from about $5 \times 10^7$ cells to about $10^8$ cells, from about $10^8$ cells to about $5 \times 10^8$ cells, or from about $5 \times 10^8$ cells to about $10^9$ cells. In some cases, a method of the present disclosure can be used to generate more than $10^9$ cells, e.g., from $10^9$ cells to $5 \times 10^9$ cells, from $5 \times 10^9$ cells to $10^{10}$ cells, from $10^{10}$ cells to $5 \times 10^{10}$ cells, from $5 \times 10^{10}$ cells to $10^{11}$ cells, from $10^{11}$ cells to $5 \times 10^{11}$ cells, from $5 \times 10^{11}$ cells to $10^{12}$ cells, from $10^{12}$ cells to $5 \times 10^{12}$ cells, from $5 \times 10^{12}$ cells to $10^{13}$ cells, from $10^{13}$ cells to $5 \times 10^{13}$ cells, from $5 \times 10^{13}$ cells to $10^{14}$ cells, from $10^{14}$ cells to $5 \times 10^{14}$ cells, or from $5 \times 10^{14}$ cells to $10^{15}$ cells.

Cells can be cultured in a hydrogel composition of the present disclosure can be present in the hydrogel composition (e.g., embedded within the hydrogel composition; suspended in the hydrogel composition; etc.) at a density of from 10 cells per mL (or cubic centimeters) hydrogel to about $10^8$ cells per mL, e.g., from about 10 cells per mL to about $10^2$ cells per mL, from about $10^2$ cells per mL to about $10^4$ cells per mL, from about $10^4$ cells per mL to about $10^6$ cells per mL, or from about $10^6$ cells per mL to about $10^8$ cells per mL.

In some cases, the hydrogel composition maintains pluripotency of pluripotent stem cells contained within the hydrogel composition. For example, in some cases, the hydrogel composition maintains pluripotency of pluripotent stem cells contained within the hydrogel composition when cultured in the hydrogel composition for a period of time of 1 day to 6 months or more. For example, in some cases, the hydrogel composition maintains pluripotency of pluripotent stem cells contained within the hydrogel composition when cultured in the hydrogel composition for a period of time of 1 day to 7 days, from 1 week to 2 weeks, from 2 weeks to one month, from one month to 2 months, from 2 months to 4 months, or from 4 months to 6 months. For example, in some cases, the hydrogel composition maintains pluripotency of at least 10%, at least 20%, at least 30%, at least 40%, at least 50%, at least 60%, at least 70%, at least 80%, at least 90%, or more than 90%, of the pluripotent stem cells contained within the hydrogel composition when cultured in the hydrogel composition for a period of time of 1 day to 7 days, from 1 week to 2 weeks, from 2 weeks to one month, from one month to 2 months, from 2 months to 4 months, or from 4 months to 6 months. In some cases, the hydrogel composition provides sufficient time for cell propagation. In some cases, the cells cultured in the hydrogel composition maintain pluripotency after 1 passage, after 2 passages, after 3 passages or after more than 3 passages. In some cases, the hydrogel composition maintains pluripotency of human pluripotent stem cells (hPSCs). In some cases, the hPSCs are H1 embryonic stem cells (H1ESCs). In some cases, the hPSCs are H9 embryonic stem cells (H9ESCs). In some cases, the hydrogel composition maintains pluripotency of induced pluripotent stem cells (iPSCs). In some cases, the iPSCs cultured in the hydrogel maintain pluripotency after 1 passage, after 2 passages, after 3 passages, or after more than 3 passages (e.g., after 4 passages, after 5 passages, after from 5 to 10 passages, after from 10 to 15 passages, after from 15 to 20 passages, etc.).

In some cases, cells cultured in the hydrogel composition aggregate. For example, in some cases, the cells cultured in the hydrogel composition grow as small aggregates after 1 day in culture. In some cases, cells cultured in the hydrogel composition grow as single cells at 1 day in culture. In some cases, the cells cultured in the hydrogel composition aggregate after 2 days in culture. In some cases, cells cultured in the hydrogel composition aggregate after 3 days in culture. In some cases, cells cultured in the hydrogel composition aggregate after 4 days in culture. In some instances, the cells are H9ESCs. In some cases, H9ESCs grow as small aggregates at 1 day in culture. In some instances, H9ESCs grow as large aggregates at 4 days in culture.

The hydrogel composition can include one or more factors (e.g., polypeptides; small molecules; etc.) that promote proliferation or differentiation of cells cultured in the hydrogel composition. Suitable factors include, e.g., retinoic acid, a Wnt agonist, an Shh signaling pathway agonist, a bone morphogenic protein (BMP) inhibitor (e.g., Noggin), a receptor tyrosine kinase ligand (e.g., epidermal growth factor), nicotinamide, a p38 inhibitor, a dual-Smad inhibitor, a Rock inhibitor, gastrin, an activator of the prostaglanding signalling pathway, fibroblast growth factor (FGF) (e.g., FGF10), a TGF-β inhibitor, Rspondin, an Rspondin mimic, and combinations of two or more of the aforementioned factors. Such factors can be present in the hydrogel composition at concentrations ranging from 1 nM to 100 mM, e.g., from 1 nM to 50 nM, from 50 nM to 100 nM, from 100 nM to 0.5 μM, from 0.5 μM to 1 μM, from 1 μM to 50 μM, from 50 μM to 100 μM, from 100 μM to 0.5 mM, from 0.5 μM to 1 mM, from 1 mM to 50 mM, or from 50 mM to 100 mM. Such factors can be present in the hydrogel composition at concentrations ranging from 1 ng/ml to 1 mg/ml, e.g., from 1 ng/ml to 50 ng/ml, from 50 ng/ml to 100 ng/ml, from 100 ng/ml to 0.5 μg/ml, from 0.5 μg/ml to 1 μg/ml, from 1 μg/ml to 50 μg/ml, from 50 μg/ml to 100 μg/ml, from 100 μg/ml to 500 μg/ml, from 500 μg/ml to 0.1 mg/ml, from 0.1 mg/ml to 0.5 mg/ml, or from 0.5 mg/ml to 1 mg/ml, or more than 1 mg/ml.

In some cases, a hydrogel composition of the present disclosure includes one or more of: Rspondin 1-4 and/or an Rspondin mimic, a BMP inhibitor (for example, Noggin), a TGF-beta inhibitor, a receptor tyrosine kinase ligand (for example, EGF), Nicotinamide, a Wnt agonist (for example, Wnt(3a)), a Wnt antagonist (e.g., IWP-2, IWP-3, IWP-4, Dkk1, and the like), a p38 inhibitor, gastrin, FGF10, HGF and a ROCK inhibitor.

Several classes of natural BMP-binding proteins are known, including Noggin, Chordin and chordin-like proteins comprising chordin domains, Follistatin and follistatin-related proteins comprising a follistatin domain, DAN and DAN-like proteins comprising a DAN cysteine-knot domain, sclerostin/SOST (R&D systems) and apha-2 macroglobulin. A BMP inhibitor is an agent that binds to a BMP molecule to form a complex wherein the BMP activity is reduced, for example by preventing or inhibiting the binding of the BMP molecule to a BMP receptor. Alternatively, the inhibitor may be an agent that binds to a BMP receptor and prevents binding of a BMP ligand to the receptor, for example, an antibody that binds the receptor. A BMP inhibitor may be a protein or small molecule and may be naturally occurring, modified, and/or partially or entirely synthetic. A BMP inhibitor can be Noggin, DAN, or DAN-like proteins including Cerberus and Gremlin. In some cases, the BMP inhibitor is Noggin. The BMP inhibitor (e.g., Noggin) may be used at any suitable concentration. A hydrogel composition of the present disclosure can include Noggin in a concentration of between about 10 ng/ml and about 100 ng/ml of Noggin.

A hydrogel composition of the present disclosure can include one or more Wnt agonists. The Wnt signalling pathway is defined by a series of events that occur when a Wnt protein binds to a cell-surface receptor of a Frizzled receptor family member. This results in the activation of Dishevelled family proteins which inhibit a complex of proteins that includes axin, GSK-3, and the protein APC to degrade intracellular beta-catenin. The resulting enriched nuclear beta-catenin enhances transcription by TCF/LEF family transcription factors. A Wnt agonist is defined as an agent that activates TCF/LEF-mediated transcription in a cell. Wnt agonists can be Wnt agonists that bind and activate a Frizzled receptor family member including any and all of the Wnt family proteins, an inhibitor of intracellular beta-catenin degradation, and activators of TCF/LEF.

Suitable Wnt agonists include a secreted glycoprotein including Wnt-1/Int-1, Wnt-2/Irp (InM-related Protein), Wnt-2b/13, Wnt-3/Int-4, Wnt-3a, Wnt-4, Wnt-5a, Wnt-5b, Wnt-6, Writ-7a, Wnt-7b, Wnt-8a/8d, Wnt-8b, Wnt-9a/14, Wnt-9b/14b/15, Wnt-10a, Wnt-10b/12, WnM 1, and Wnt-16. Other suitable Wnt agonists include the R-spondin family of secreted proteins, which is implicated in the activation and regulation of Wnt signaling pathway and which is comprised of 4 members (R-spondin 1, R-spondin 2, R-spondin 3, and R-spondin-4), and Norrin (also called Nome Disease Protein or NDP), which is a secreted regulatory protein that functions like a Wnt protein in that it binds with high affinity to the Frizzled-4 receptor and induces activation of the Wnt signaling pathway. Also suitable is an R-spondin mimic, for example an agonist of Lgr5 such as an anti-Lgr5 antibody.

Suitable Wnt agonists include a GSK-inhibitor. Known GSK-inhibitors comprise small-interfering RNAs (siRNA), lithium, kenpaullone, 6-Bromoindirubin-30-acetoxime, SB 216763 and SB 415286, and FRAT-family members and FRAT-derived peptides that prevent interaction of GSK-3 with axin.

Suitable Wnt agonists include Wnt-3a, a GSK-inhibitor (such as CHIR99021), Wnt 5, Wnt-6a, Norrin, and any other Wnt family protein.

A Wnt agonist can be included in the hydrogel composition in a suitable concentration. For example, CHIR99021 (6-[[2-[[4-(2,4-Dichlorophenyl)-5-(5-methyl-1H-imidazol-2-yl)-2-pyrimidinyl]amino]ethyl]amino]-3-pyridinecarbonitrile) can be included in a final concentration of between 50 nM and 100 µM, for example between 100 nM and 50 µM, between 1 µM and 10 µM, between 1 µM and 5 µM, or 3 µM.

A hydrogel composition of the present disclosure can comprise one or more receptor tyrosine kinase ligands. An example of a suitable receptor tyrosine kinase ligand is EGF, which is the ligand for the receptor tyrosine kinase EGFR. Many receptor tyrosine kinase ligands are also mitogenic growth factors.

A hydrogel composition of the present disclosure can include a TGF-1 inhibitor. Examples of suitable TGF-1 inhibitors include, e.g., 3-(6-methyl-2-pyridinyl)-N-phenyl-4-(4-quinolinyl)-1H-pyrazole-1-carbothioamide (A83-01); 4-[4-(1,3-benzodioxol-5-yl)-5-(2-pyridinyl)-1H-imidazol-2-yl]benzamide (SB-431542); and the like. Suitable TGF-1 inhibitors include those listed in Table 1 of U.S. Patent Publication No. 2014/0243227; for example, A83-01, SB-431542, SB-505124, SB-525334, SD-208, LY-36494 and SJN-2511.

A hydrogel composition of the present disclosure can comprise one or more mitogenic growth factor. The one or more mitogenic growth factor may be selected from a family of growth factors comprising epidermal growth factor (EGF), Transforming Growth Factor-alpha (TGF-alpha), basic Fibroblast Growth Factor (bFGF), brain-derived neurotrophic factor (BDNF), and Keratinocyte Growth Factor (KGF).

A hydrogel composition of the present disclosure can include a Rock (Rho-kinase) inhibitor. Suitable Rock inhibitors include, e.g., R-(+)-trans-4-(1-aminoethyl)-N-(4-Pyridyl)cyclohexanecarboxamide dihydrochloride monohydrate (Y-27632, Sigma-Aldrich), 5-(1,4-diazepan-1-ylsulfonyl)isoquinoline (fasudil or HA1077, Cayman Chemical), and (S)-(+)-2-methyl-1-[(4-methyl-5-isoquinolinyl)sulfonyl]-hexahydro-1H-1,4-diazepine dihydrochloride (H-1 152, Tocris Bioschience).

A hydrogel composition of the present disclosure can include a Notch agonist. Examples of suitable Notch agonists include Jagged 1 and Delta 1, or an active fragment or derivative thereof. A suitable Notch agonist is a DSL peptide (Dontu et al., 2004. Breast Cancer Res 6. R605-R615) with the sequence CDDYYYGFGCNKFCRPR (SEQ ID NO:1).

A hydrogel composition of the present disclosure can include an activator of the prostaglandin signalling pathway Such activators include, e.g., Phospholipids, Arachidonic acid (AA), prostaglandin E2 (PGE2), prostaglandin G2 (PGG2), prostaglandin F2 (PGF2), prostaglandin H2 (PGH2), and prostaglandin D2 (PGD2).

A hydrogel composition of the present disclosure can include a RANK ligand.

The pH of a hydrogel composition of the present disclosure can be in the range from about 7.0 to 7.8, in the range from about 7.2 to 7.6, or about 7.4. The pH may be maintained using a buffer. A suitable buffer can readily be selected by the skilled person. Buffers that may be used include carbonate buffers (e.g. $NaHCO_3$), and phosphates (e.g. $NaH_2PO_4$). Other buffers such as N-[2-hydroxyethyl]-piperazine-N-[2-ethanesul-phonic acid] (HEPES) and 3-[N-morpholino]-propanesulfonic acid (MOPS) may also be used.

A hydrogel composition of the present disclosure one or more amino acids. Amino acids which may be present include L-alanine, L-arginine, L-asparagine, L-aspartic acid, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, L-valine and combinations thereof.

A hydrogel composition of the present disclosure can include one or more vitamins. Vitamins which may be present include thiamine (vitamin B1), riboflavin (vitamin B2), niacin (vitamin B3), D-calcium pantothenate (vitamin B5), pyridoxal/pyridoxamine/pyridoxine (vitamin B6), folic acid (vitamin B9), cyanocobalamin (vitamin B12), ascorbic acid (vitamin C), calciferol (vitamin D2), DL-alpha tocopherol (vitamin E), biotin (vitamin H) and menadione (vitamin K).

A hydrogel composition of the present disclosure can include one or more inorganic salts. Inorganic salts that may be present include salts of calcium, copper, iron, magnesium, potassium, sodium, zinc. The salts are normally used in the form of chlorides, phosphates, sulfates, nitrates and bicarbonates.

In some cases, a hydrogel composition of the present disclosure does not include serum, e.g., the hydrogel composition is serum free. In some cases, a hydrogel composition of the present disclosure includes a serum replacement.

A hydrogel composition of the present disclosure can include other components. A hydrogel composition of the present disclosure can include standard culture medium components, such as amino acids, vitamins, inorganic salts, a carbon energy source, and a buffer. Other standard cell culture components that may be included in the culture include hormones, such as progesterone, proteins, such as albumin, catalase, insulin, and transferrin.

A hydrogel composition of the present disclosure can include known cell culture media. The skilled person will understand from common general knowledge the types of culture media that might be used for cell culture, including stem cell culture. Suitable cell culture media are available commercially, and include, but are not limited to, Dulbecco's Modified Eagle Media (DMEM), Minimal Essential Medium (MEM), Knockout-DMEM (KO-DMEM), Glasgow Minimal Essential Medium (G-MEM), Basal Medium Eagle (BME), DMEM/Ham's F12, Advanced DMEM/Ham's F12, Iscove's Modified Dulbecco's Media and Minimal Essential Media (MEM), Ham's F-10, Ham's F-12, Medium 199, and RPMI 1640 Media.

Cells that can be cultured using a method of the present disclosure include mammalian cells. The cells can be undifferentiated cells, such as pluripotent, multipotent, oligopotent or unipotent cells. The cells can be differentiated cells. The cells can be a mix of differentiated and undifferentiated cells. The cells being cultured in a hydrogel composition of the present disclosure can be a single type of cell; or can be a mixture of two or more types of cells.

The cells can be primary cells, genetically modified cells (e.g., genetically modified primary cells), and the like. The cells can be human cells, non-human primate cells, rodent (e.g., mouse; rat) cells, lagomorph (e.g., rabbit) cells, ungulate cells, etc. Cells of any of a variety of cell types can be cultured using a method of the present disclosure. Such cells can include cells from tissue samples, including but not limited to, blood, bone, brain, kidney, muscle, spinal cord, nerve, endocrine system, uterine, ear, foreskin, liver, intestine, bladder or skin. The cells can be obtained from an individual having a particular disease or an individual in need of pluripotent stem cells. The cells can include neural cells, lymphocytes, epidermal cells, intestinal cells, fibroblasts, keratinocytes, adipocytes, cardiomyocytes, pancreatic islet cells, hepatocytes, astrocytes, oligodendrocytes, retinal cells, and the like. The cells can be autologous cells; for example, the cells can be obtained from an individual, and cultured using a method of the present disclosure, whereupon, after culturing (and possible modification, differentiation, etc.), returned to the individual from which the cells were obtained. In some cases, the cells are human cells. In some cases, the cells are rodent (e.g., mouse; rat) cells. In some cases, the cells are non-human primate cells.

Cells that can be cultured using a method of the present disclosure include hematopoietic stem cells, embryonic stem cells, mesenchymal stem cells, neural stem cells, epidermal stem cells, endothelial stem cells, gastrointestinal stem cells, liver stem cells, cord blood stem cells, amniotic fluid stem cells, skeletal muscle stem cells, smooth muscle stem cells (e.g., cardiac smooth muscle stem cells), pancreatic stem cells, olfactory stem cells, hematopoietic stem cells, induced pluripotent stem cells; and the like In some cases, cells cultured using a method of the present disclosure are stem cells. In some cases, cells cultured using a method of the present disclosure are pluripotent stem cells.

Suitable human embryonic stem (ES) cells include, but are not limited to, any of a variety of available human ES lines, e.g., BG01 (hESBGN-01), BG02 (hESBGN-02), BG03 (hESBGN-03) (BresaGen, Inc.; Athens, Ga.); SA01 (Sahlgrenska 1), SA02 (Sahlgrenska 2) (Cellartis AB; Goeteborg, Sweden); ES01 (HES-1), ES01 (HES-2), ES03 (HES-3), ES04 (HES-4), ES05 (HES-5), ES06 (HES-6) (ES Cell International; Singapore); UC01 (HSF-1), UC06 (HSF-6) (University of California, San Francisco; San Francisco, Calif.); WA01 (H1), WA07 (H7), WA09 (H9), WA13 (H13), WA14 (H14) (Wisconsin Alumni Research Foundation; WARF; Madison, Wis.). Cell line designations are given as the National Institutes of Health (NIH) code, followed in parentheses by the provider code. See, e.g., U.S. Pat. No. 6,875,607. Suitable human ES cell lines can be positive for one, two, three, four, five, six, or all seven of the following markers: stage-specific embryonic antigen-3 (SSEA-3); SSEA-4; TRA 1-60; TRA 1-81; Oct-4; GCTM-2; and alkaline phosphatase.

Hematopoietic stem cells (HSCs) are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art. In some cases, NSCs cultured in the hydrogel composition remain multipotent after multiple passages.

Mesenchymal stem cells (MSC), originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

An induced pluripotent stem (iPS) cell is a pluripotent stem cell induced from a somatic cell, e.g., a differentiated somatic cell. iPS cells are capable of self-renewal and differentiation into cell fate-committed stem cells, including neural stem cells, as well as various types of mature cells.

iPS cells can be generated from somatic cells, including skin fibroblasts, using, e.g., known methods. iPS cells produce and express on their cell surface one or more of the following cell surface antigens: SSEA-3, SSEA-4, TRA-1-60, TRA-1-81, TRA-2-49/6E, and Nanog. In some embodiments, iPS cells produce and express on their cell surface SSEA-3, SSEA-4, TRA-1-60, TRA-1-81, TRA-2-49/6E, and Nanog. iPS cells express one or more of the following genes: Oct-3/4, Sox2, Nanog, GDF3, REX1, FGF4, ESG1, DPPA2, DPPA4, and hTERT. In some embodiments, an iPS cell expresses Oct-3/4, Sox2, Nanog, GDF3, REX1, FGF4, ESG1, DPPA2, DPPA4, and hTERT. Methods of generating iPS are known in the art, and any such method can be used to generate iPS. See, e.g., Takahashi and Yamanaka (2006) Cell 126:663-676; Yamanaka et. al. (2007) Nature 448:313-7; Wernig et al. (2007) Nature 448:318-24; Maherali (2007) Cell Stem Cell 1:55-70; Nakagawa et al. (2008) Nat. Biotechnol. 26:101; Takahashi et al. (2007) Cell 131:861; Takahashi et al. (2007) Nat. Protoc. 2:3081; and Okita et al. (2007 Nature 448:313.

iPS cells can be generated from somatic cells (e.g., skin fibroblasts) by genetically modifying the somatic cells with one or more expression constructs encoding Oct-3/4 and Sox2. In some embodiments, somatic cells are genetically modified with one or more expression constructs comprising nucleotide sequences encoding Oct-3/4, Sox2, c-myc, and Klf4. In some embodiments, somatic cells are genetically modified with one or more expression constructs comprising nucleotide sequences encoding Oct-4, Sox2, Nanog, and LIN28.

In some cases, cells cultured using a method of the present disclosure are somatic stem cells (also known as "adult stem cells"). Suitable somatic stem cells include, e.g., tissue stem cells; and tissue precursor cells. Stem cells that can be cultured in a hydrogel composition of the present disclosure include, e.g., neural stem cells, hematopoietic stem cells, mammary stem cells, epidermal stem cells, intestinal stem cells, mesenchymal stem cells, endothelial stem cells, pancreatic stem cells, dermal stem cells, myocardial stem cells, oligodendrocyte precursor cells, neural stem cells, olfactory adult stem cells, neural crest stem cells, hepatic stem cells, and the like.

Methods of Differentiating Cells

The present disclosure provides methods of producing differentiated cells from a stem cell or a precursor cell, the methods comprising culturing a stem cell or precursor cell in a hydrogel composition of the present disclosure, for a period of time and under conditions suitable for inducing differentiation of the stem cell or precursor cell. Conditions for inducing differentiation of a stem cell or precursor cell depend in part on the desired differentiated cell. Conditions can include inclusion in the hydrogel of one or more factors that induce differentiation.

Methods of Isolating Cells

The present disclosure provides methods of producing a stem cell, a precursor cell, or a differentiated cell, the methods comprising: a) culturing a cell in a hydrogel composition of the present disclosure; and b) isolating the cell from the hydrogel composition. For example, in some cases, a cell is cultured in a hydrogel composition of the present disclosure at a temperature at which the hydrogel is a semi-solid (e.g., a gel) (e.g., 37° C.); and the cell, or progeny of the cell, is isolated from the hydrogel composition by reducing the temperature (e.g., to about 4° C.) of the hydrogel composition such that the hydrogel composition becomes a liquid. A cell can be isolated from a liquid form of the hydrogel composition using centrifugation or any other means.

In some cases, a method of the present disclosure comprises: a) culturing a stem cell in a hydrogel composition of the present disclosure at a temperature at which the hydrogel is a semi-solid (e.g., a gel), where the hydrogel composition comprises one or more factors that induce differentiation of the stem cell; b) reducing the temperature of the hydrogel composition such that the hydrogel composition becomes a liquid; and c) isolating the differentiated cell(s) from the liquid.

In some cases, a method of the present disclosure comprises: a) culturing a stem cell in a hydrogel composition of the present disclosure at a temperature at which the hydrogel is a semi-solid (e.g., a gel), where the hydrogel composition comprises one or more factors that promote growth and proliferation of the stem cell; b) reducing the temperature of the hydrogel composition such that the hydrogel composition becomes a liquid; and c) isolating the proliferated stem cells from the liquid.

Treatment Methods

The present disclosure provides methods of treating a disease or disorder in an individual in need thereof. In some cases, the methods involve culturing cells using a method of the present disclosure, as described above; isolating the cells; and administering to the individual the isolated cells. In some cases, the methods involve implanting into the individual a thermoreversible polymer-cell composition of the present disclosure.

Diseases that can be treated using cells cultured in a thermoreversible polymer of the present disclosure, or using a thermoreversible polymer-cell composition of the present disclosure, include, but are not limited to, autoimmune disease; diseases for which treatment involves regeneration of neural cells/tissue; diseases for which treatment involves regeneration of cardiac cells/tissues; Parkinson's Disease; and Alzheimer's Disease. Cells differentiated from the stem cells using a method of the present disclosure include myocardial cells, insulin-producing cells, neuronal cells, oligodendrocytes, and the like; such cells can be safely utilized in stem cell transplantation therapies for treatment of various diseases such as heart failure, insulin dependent diabetes mellitus, Parkinson's disease and spinal cord injury. Stem cells, or differentiated cells derived therefrom, can be used for autologous cells therapy, wherein the therapy is specific (e.g., personalized) for a particular subject. Stem cells, or differentiated cells derived therefrom, can be used for or non-autologous therapy.

Subjects suitable for treatment with a subject method include individuals who have been diagnosed as having a blood cell cancer (e.g., a leukemia); individuals who have been diagnosed with AIDS; individuals with sickle cell anemia; individuals with an immune disorder, e.g., an acquired immunodeficiency, a genetic immunodeficiency; individuals with Type 1 diabetes; individuals with a nervous system disorder such as Alzheimer's disease, Parkinson's disease, Huntington's disease, Lou Gehrig's disease, spinal cord injury, stroke, etc.; individuals with a liver disorder such as hepatitis, cirrhosis, a metabolic disorder affecting the liver or central nervous system (e.g., lysosomal storage disease); individuals with a disorder of the cartilage or bone, e.g., individuals requiring joint replacement, individuals with osteoarthritis, individuals with osteoporosis, etc.; individuals with a cardiac disorder, e.g., myocardial infarction, coronary artery disease, or other disorder resulting in ischemic cardiac tissue; individuals with renal disorders, e.g., kidney failure (e.g., individuals on kidney dialysis); individuals with skeletal muscle disorders, such as muscular dystrophy; and individuals with a lung disorder such as emphysema, pulmonary fibrosis, idiopathic pulmonary fibrosis, etc.

Utility

The subject thermoreversible polymers, hydrogels and methods find use in a variety of applications. Applications of interest include, but are not limited to, applications where the culturing and/or differentiation of cells are of interest. Protocols of interest can use single cells or small aggregates of stem cells and evenly disperse them throughout the hydrogel material at cold temperatures. The material can then either be spread out onto a two-dimensional surface or dropped into warm media in a stirred tank reactor. Upon warming to 37° C., the material can gel and encapsulate the cells. After changing media every day or every other day and checking progress of cell growth, the materials can be cooled and centrifuged to isolate the cells.

One application of the present disclosure involves the proliferation of stem cells. The subject materials find use in culturing stem cells for multiple days at high proliferation rates. The cells remain pluripotent after growing in the subject hydrogels (see e.g., Oct4/Nanog antibody staining in FIG. 10).

Another application involves differentiation of cells into specific cell types. The subject materials can be modified to select a particular hydrogel stiffness that reflects a specific tissue environment. In addition, the subject materials can also incorporate growth factors or other biochemical cues to guide the differentiation of stem cells down specific lineages. Incorporation of these growth factors within the material can significantly decrease the amount of overall proteins added, thus reducing costs and time during media changes as well as increasing the potency and efficiency of the added growth factors. These materials can be used for differentiation of stem cells. Growth factors can be added to the surrounding media or attached via heparin before cells are incorporated into the hydrogel. After sufficient time for differentiating to the correct (desired) cell type, the cells can be isolated by cooling and centrifugation.

In some applications, the subject materials can be modified to be very soft and have a gel transition temperature very close to body temperature for use in injections. For instance, soft gels with differentiated neurons could be injected into the brain for cell replacement therapy. The subject materials can also be modified for biodegradability, so that cells could be grown, differentiated, and injected all in one material. The biodegradable links a subject to clear out the material after the cells have been administered.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Design of Thermoreversible Polymers

Materials were developed that make cell (e.g., stem cell) propagation simple, are fully defined, and biochemically tunable, e.g., through the facile incorporation of proteins to guide cell behavior. Systems were designed for ease of cell passaging (i.e. cell recovery) from one culture to the next with minimal steps and avoiding any harsh processes that could damage these delicate cells. Fully defined materials engineered to be thermoreversible provide for cells to be incorporated at cold temperatures into a liquid and then encapsulated at warm temperatures when the material gels. Simple cooling and centrifugation are required to recover cells from the material, thus avoiding harmful shear stress and pressure changes associated with many other three-dimensional systems (FIG. 1).

The materials used are fully synthetic or semi-synthetic making them fully defined. In order to obtain hydrogels with desirable properties including stiffness, gelation temperature, and viscosity, the ratio of hydrophobic and hydrophilic components as well as the size of the polymers is varied. Chemical functional groups are incorporated within these systems to conjugate heparin which can ultimately attach additional proteins, or to conjugate specific biochemical molecules such as peptides or proteins. The resulting defined, highly tunable, 3D system provides strong utility and versatility for desirable 3D stem cell growth and differentiation.

Figure 2:
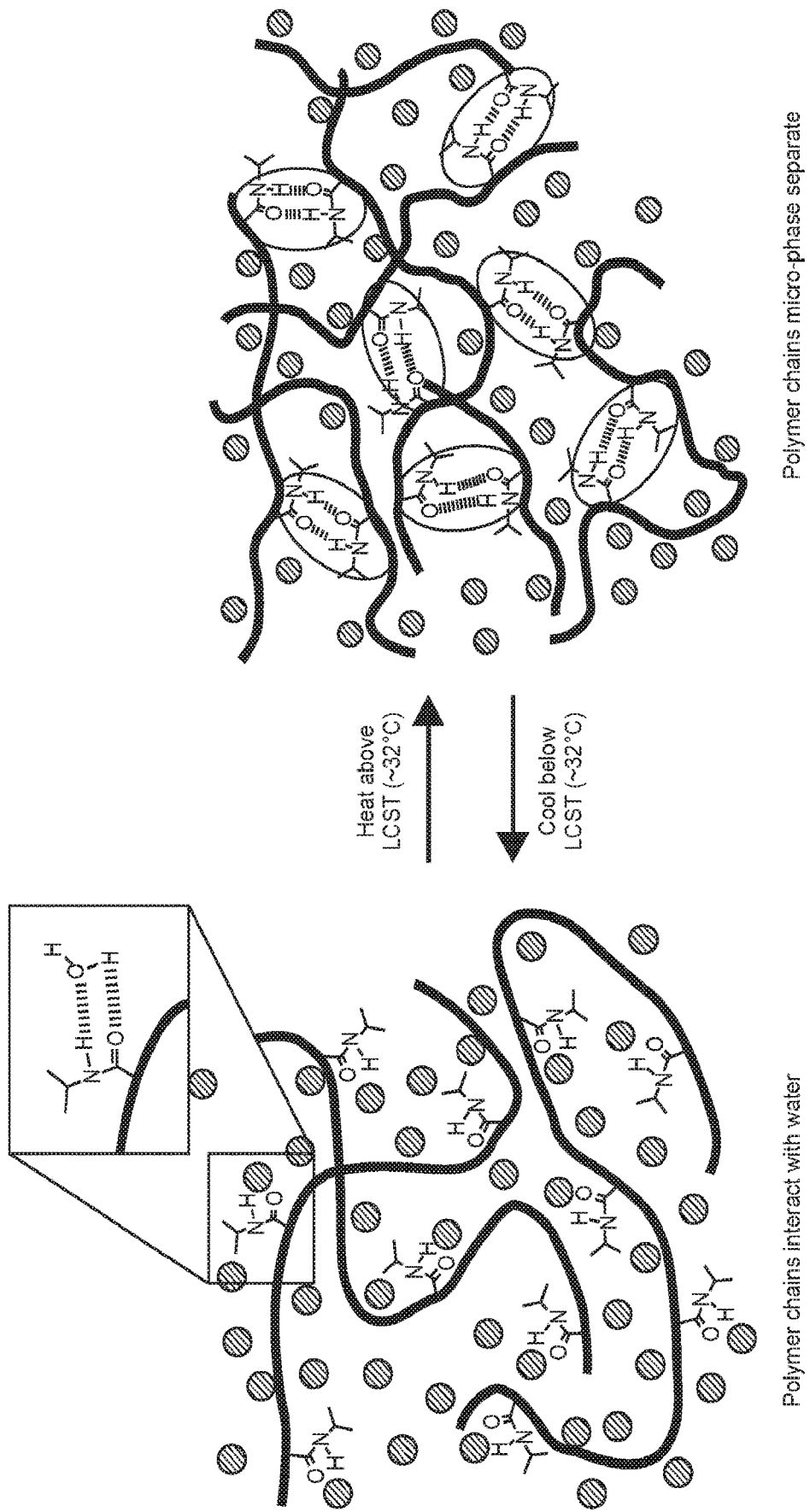
FIG. 2 depicts PNIPAM amide groups hydrogen bonding with water below the lower critical solution temperature (LCST) and hydrogen bonding with each other above the LCST, creating hydrophobic microdomains.
Figure 3:
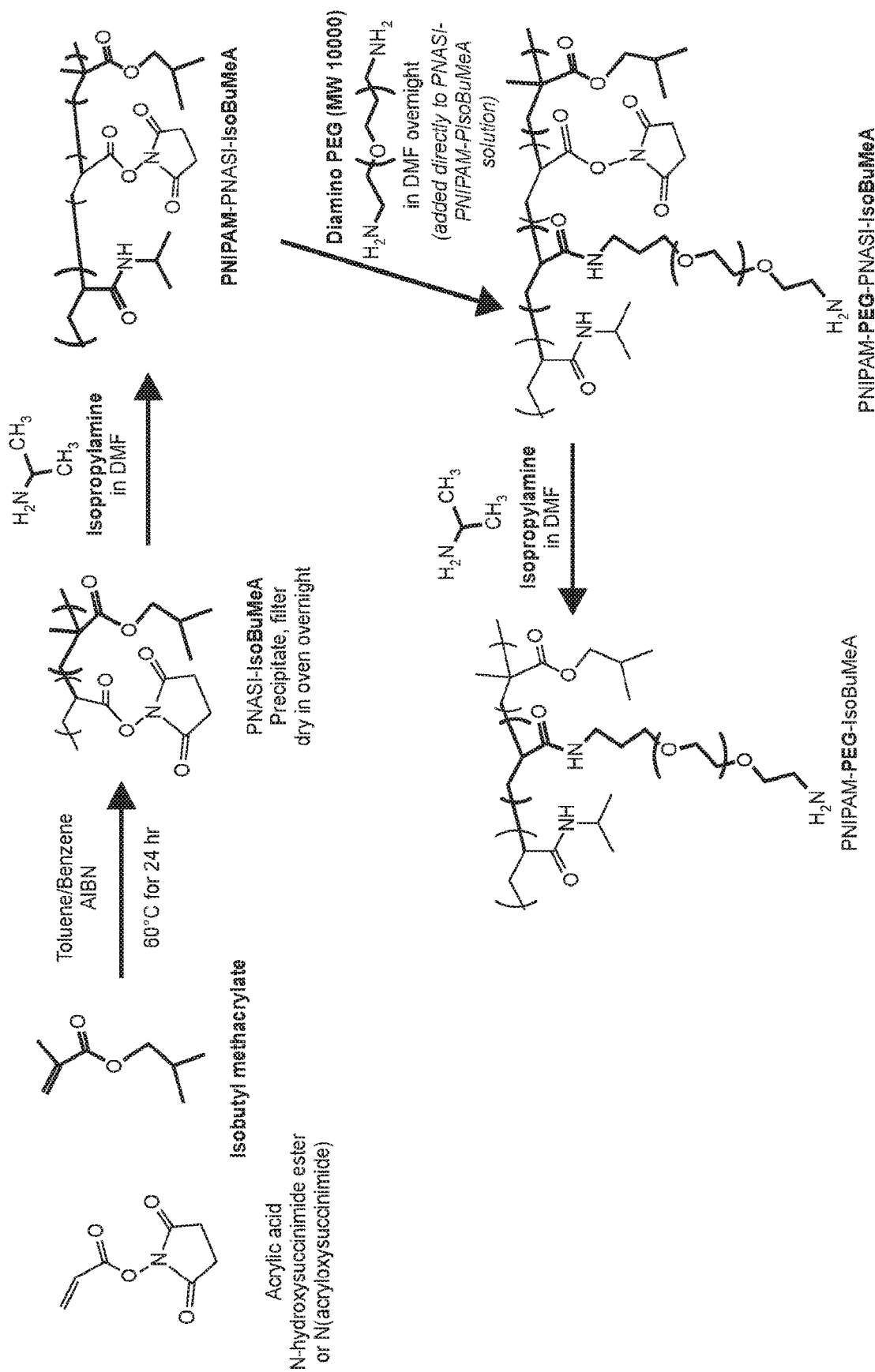
FIG. 3 shows a scheme for the synthesis of an exemplary polymer, PNIPAM-PEG-Isobutyl methacrylate. The same synthesis strategy can be performed to incorporate different methacrylate groups. A moiety of interest, such as heparin can be attached via the free amine groups of the PEG.

Two different systems were developed which have similar uses but which include of two different polymer families. Synthetic and semi-synthetic materials were used as the base of our hydrogel systems to obtain more reproducible physical and chemical properties and to be able to molecularly tailor the materials for ultimate needs. Both systems utilize Poly(N-isopropylacrylamide) (PNIPAM) as a thermoreversible polymeric segment/component. PNIPAM by itself has a lower critical solution temperature (LCST) in water or aqueous buffers around 32° C., meaning that it transitions from a soluble state to an insoluble state when it is heated above its LCST (see e.g., Chiantore et al., Solution Properties of Poly(N-Isopropylacrylamide), Makromol Chem 1979, 180, 969-973). When the PNIPAM-based thermoreversible polymer is attached to other polymers that can interact with water, the entire polymer can become thermoreversible, i.e. transition from a liquid state to a solid/gel state when heated above the LCST. The acrylamide groups hydrogen bond with water below the LCST, and above the LCST it becomes more favorable for the acrylamide groups to hydrogen bond with each other than with water, creating hydrophobic domains that can physically entangle/ "crosslink" the entire gel (see FIG. 2).

One polymer system was developed that includes a functionalized hyaluronic acid with a PNIPAM-based thermoreversible polymer attached. Hyaluronic acid is a natural polysaccharide that is found in the extracellular matrix of connective tissues. Some of its roles include cell differentiation, tissue hydration, nutrient diffusion, and proteoglycan organization.

Another other polymer system that was developed is a PNIPAM-based thermoreversible polymer that incorporates a poly(ethylene glycol) (PEG) co-monomer and a methacrylate group. PEG is also nontoxic and non-immunogenic, does not allow proteins to adhere, and is biocompatible.

These polymer systems find use in hydrogels for encapsulating and suspending cells in three-dimensional bioreactors for scale-up production in tanks. The present systems are also well defined, and use biocompatible components. This provides for the use of the stem cells cultured or differentiated in the subject hydrogels for therapeutic purposes in humans. The present systems maintain the viability of cells (e.g., stem cells) and avoid harsh methods of recovery of the cells from the system.

Three-dimensional systems designed for cell culture can produce more cells than two-dimensional systems. The mechanical and biochemical characteristics of the subject hydrogel systems (e.g., stiffness and viscosity) were investigated for supporting cell growth in three dimensional bioreactors.

The LCST and mechanical properties of the subject three-dimensional systems can be tuned based on the size or chemical nature of the main polymer and attached modifying agent as well as by varying the ratio of hydrophilic and hydrophobic components. The materials can reflect the stiffness of different tissue environments to better support cell growth or differentiation. The present materials also provide for visualization of cells cultured within the optically clear materials; cell progress and aggregate size can be closely monitored when materials are pipetted into a cell culture well.

Biochemical cues that find use in the growth and differentiation of cells can be incorporated using chemical functionalities for simple attachment of either heparin for subsequent protein attachment or other biochemical cues like peptides or proteins. These biochemical additions aid cell culture by increasing the local concentration and potency of proteins of interest as well as limiting the occurrence of protein degradation via endocytosis or other mechanisms. The overall cost of the system and media can thereby be significantly lowered by reducing the amount of proteins required in the media. This property can also alleviate some of the transport limitations associated with three-dimensional systems. Furthermore, the system can be further tuned by incorporating biochemical cues that guide differentiation into therapeutically relevant cell types.

The thermoreversible PNIPAM-based polymers provide for easy cell recovery utilizing gentle processing steps of cooling and centrifugation after the cells have been encapsulated at warm temperatures. The subject polymers provide hydrogels that are easy to handle between 0° C. and 37° C. At cold temperatures the subject hydrogels are fluid enough to be pipettable but viscous enough so that cells do not settle before warming step. The transition temperature from liquid to gel has also been selected so that the gels do not re-liquefy if the temperature drops to room temperature but also do not gel immediately above freezing temperatures. The transition from liquid to gel is very quick, encapsulating cells in a suspended state, and providing for systems with cells to be immediately solidified upon addition to warm media.

Example 2: PNIPAM-PEG Polymers

In the PNIPAM-PEG system, the hydrophilic PEG included in the system increases the LCST and depending on PEG length can make the hydrogels softer. Alternatively, incorporation of more hydrophobic groups such as methacrylates (e.g., butyl/isobutyl/ethyl/methyl methacrylates) can lower the LCST and make the resulting materials stiffer. A homobifunctional diamino-PEG was utilized to attach PEG groups to the polymer (via the NHS ester groups of the N-acryloxysuccinimide polymer) (see FIG. 3). The reactions are performed dilute enough so that there is minimal opportunity for the amine groups to crosslink across different polymer chains. The free amines at the terminal of these PEG chains can also be used for introducing additional chemical functionality or linked modifying agents of interest, for instance via conjugations with carboxylic acid groups of an agent of interest (see FIG. 3). The PEG component can be varied by changing the length of PEG used or by using a heterobifunctional PEG with an amine group on one terminal only. A variety of additional functionalities can be incorporated for use in other types of chemical conjugation reactions based on the chemical group on the end of the PEG chains.

Initially, hydrogels were prepared using PNIPAM and PEG to investigate the range of PEG contents which can make gels at 37° C. Increasing PEG content from 9 wt %-30 wt % can shift the stiffness of the resulting polymer by orders of magnitude lower as well as shift the LCST by more than 10° C.

Butyl methacrylate groups were incorporated onto the backbone to lower the LCST and investigate the effect on polymer stiffness. Initial tests utilized 3,400 MW diaminoPEG and the starting poly(N-acryloxysuccinimide)-butylmethacrylate (PNASI-BuMeA) polymer made in 100% toluene (assume 6 kg/mol molecular weight based on polyethylene oxide (PEO) GPC standards). The resulting thermosensitive polymers made gels at 37° C. that re-liquefied upon cooling. However, in some cases the hydrogels were too soft for cell culture; when cells were plated within these gels, the vibration forces from moving the plate would force all the cells to the middle of the gels and did not support healthy cells. Also, the viscosity was too low for these materials at cold temperatures, such that upon pipetting onto cell culture plates, the material flowed to the edges of the well instead of staying intact as a gel.

Figure 4:
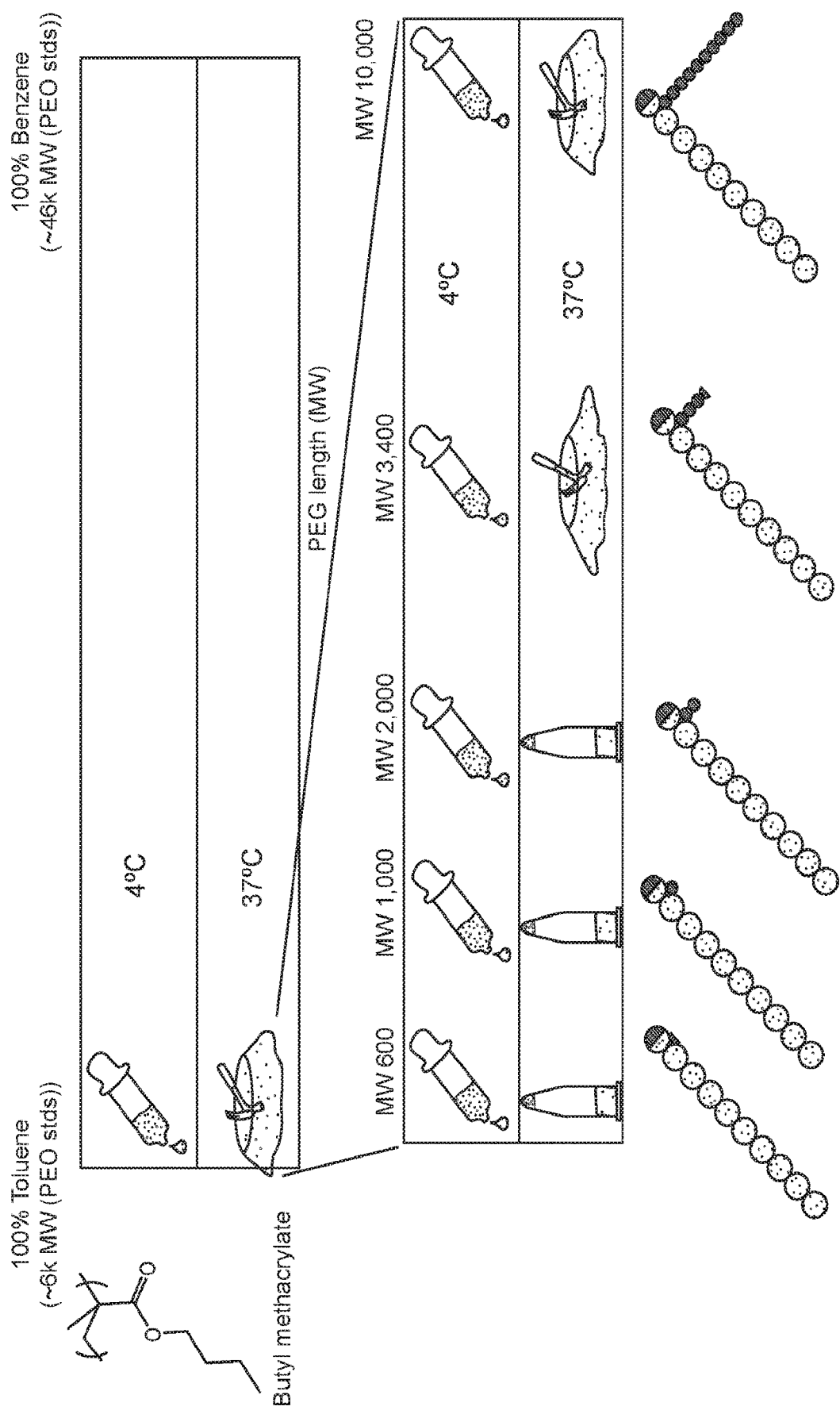
FIG. 4 illustrates that small molecular weight PNIPAM-PEG-Butyl methacrylates do not produce stiff gels using a variety of PEGs of various lengths or concentration.
Figure 20:
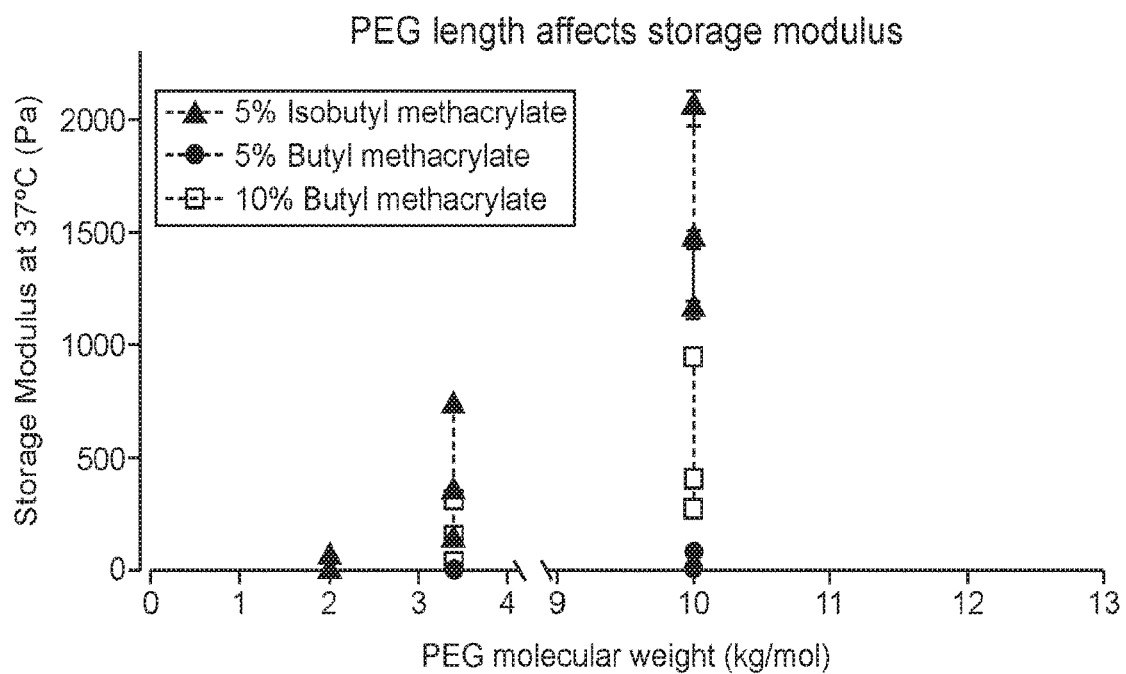
FIG. 20 summarizes rheology data illustrating the increased storage modulus with larger PEG molecular weight for copolymers containing isobutyl methacrylate and butyl methacrylate.
Figure 21:
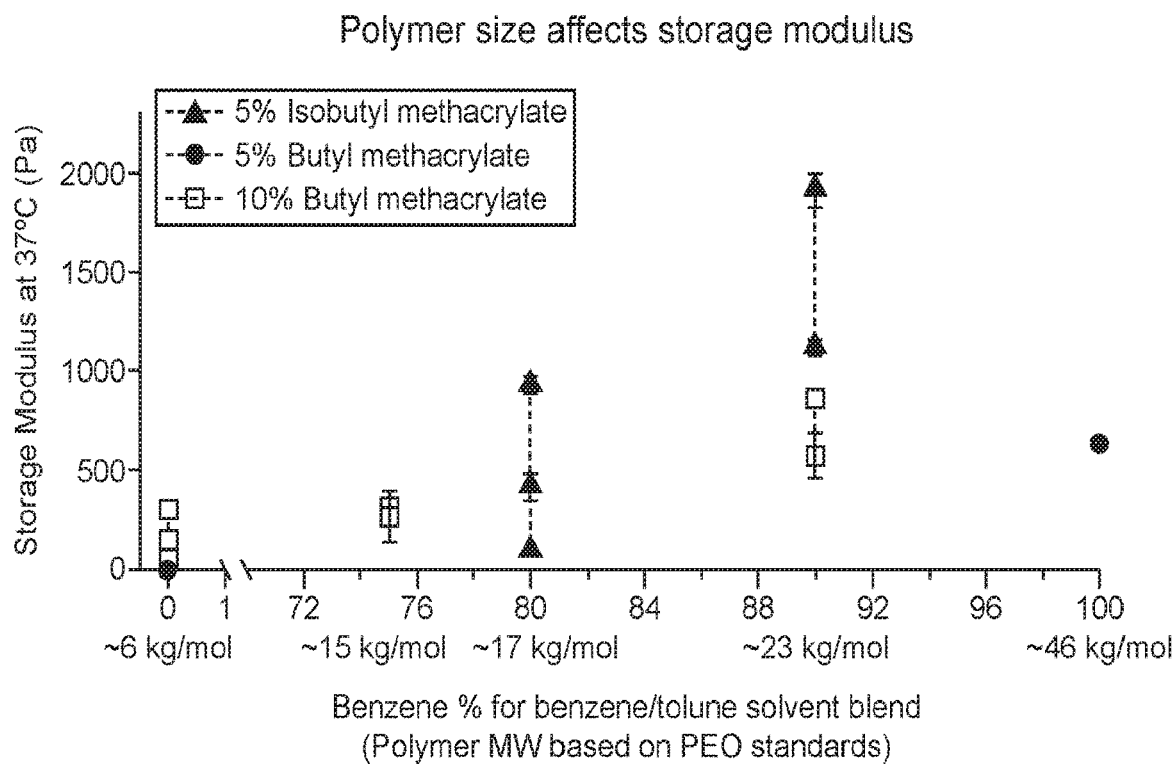
FIG. 21 depicts an increase in storage modulus with increasing PNIPAM-PEG-BuMeA or PNIPAM-PEG-IsoBuMeA polymer size (based on ratio of solvents during synthesis).

To address this problem, the same size PNASI-BuMeA or IsoBuMeA polymer and BuMeA or IsoBuMeA content was maintained, but the length of the diaminoPEG was changed. For both types of methacrylate copolymers, a trend appeared showing an increase in storage modulus with longer diaminoPEG polymers (see FIG. 20) Using 10,000 MW diaminoPEG created stable hydrogels at 37° C. although the polymers were softer than those made with 3,400 MW PEG. Upon using shorter PEG chains of, e.g., 600, 1000 and 2000 MW, gels would not form no matter the amount of PEG that was attached (see FIG. 4).

Figure 5:
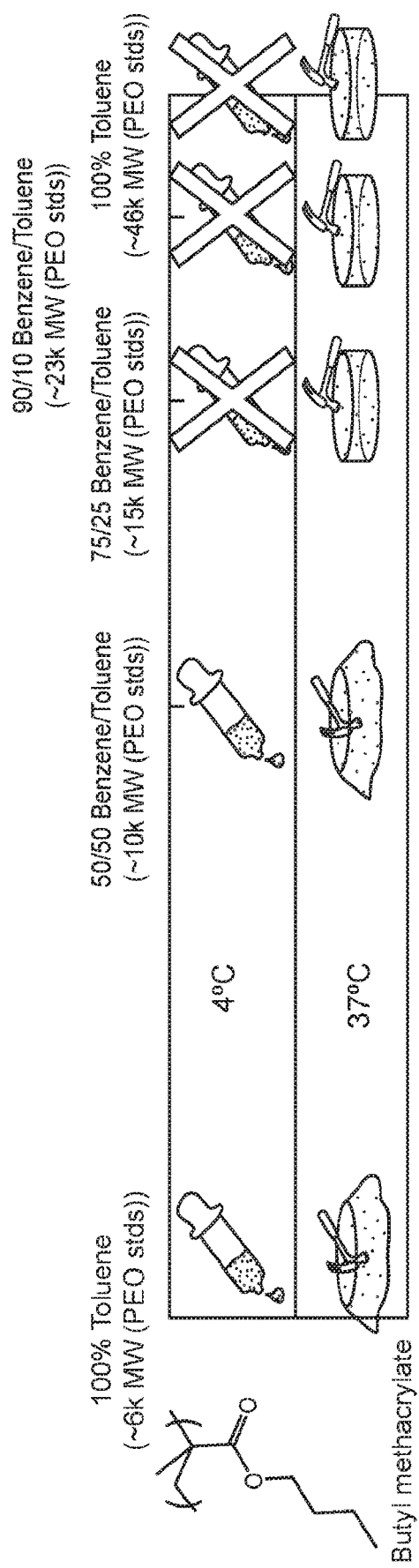
FIG. 5 illustrates that higher molecular weight PNIPAM-PEG-BuMeA copolymers can make gels that are stiff but which do not re-liquefy after being held at a temperature of 37° C. for more than a few hours.
Figure 6:
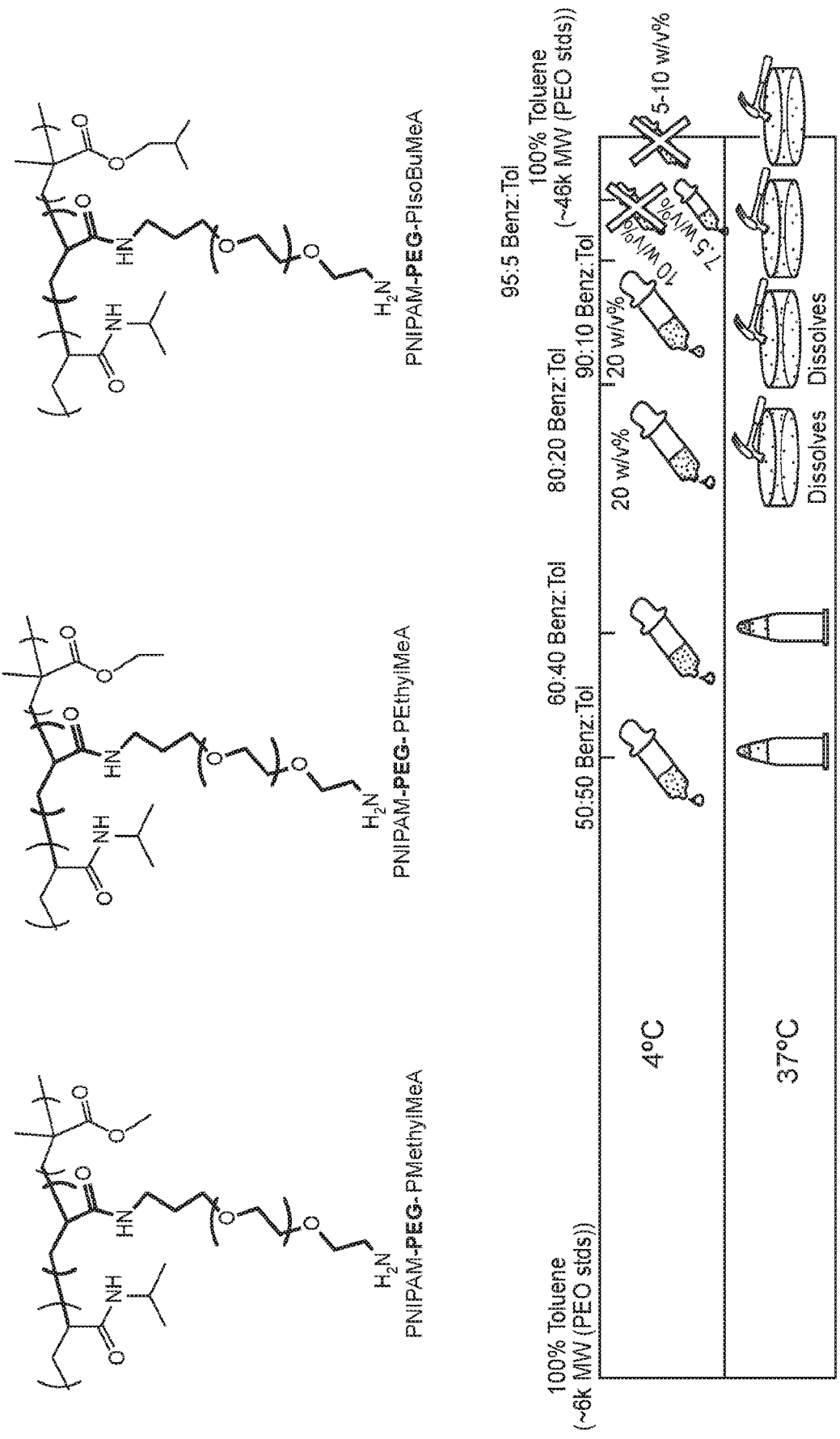
FIG. 6 illustrates the results of using methyl, ethyl or isobutyl methacrylate during synthesis to prepare stiff gels with higher molecular weights.
Figure 7A:
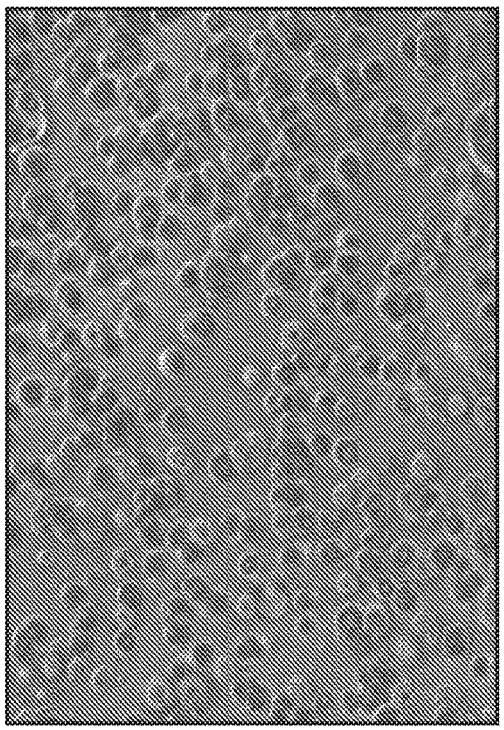
FIG. 7A-7D shows images of cell aggregates growing in an exemplary PNIPAM-PEG-Isobutyl methacrylate hydrogel.
Figure 7B:
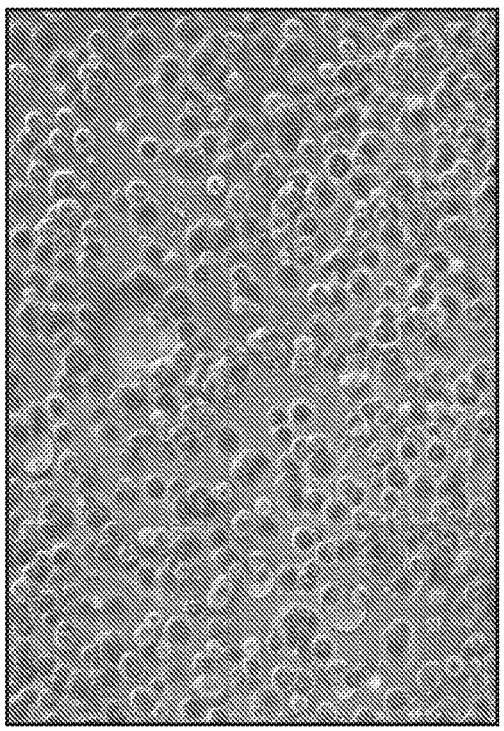
Figure 7C:
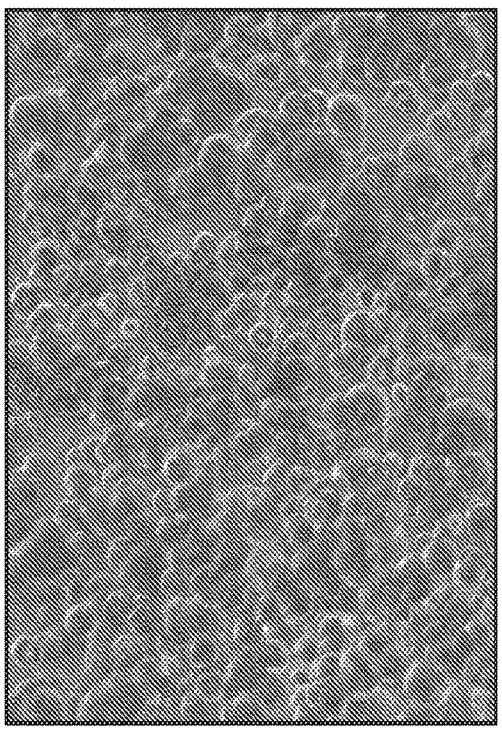
Figure 7D:
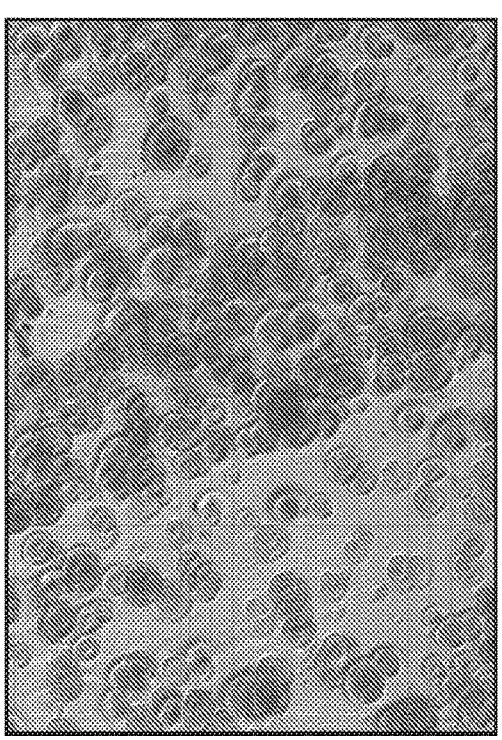

Gels were prepared that are stiff enough at 37° C. for use in cell cultures, by starting with PNASI-BuMeA-based polymers made in 100% benzene (assume MW ~46 kg/mol). These polymers required less material to make a gel (10 wt/vol % vs. 20 wt/vol %) and made transparent, stiff gels (~1 kPa G') at 37° C. However, after being held at 37° C. for more than 1 hour, these gels did not re-liquify at cold temperatures. Changing the concentration in solution to 7.5 or 5 w/v % produced softer gels that did not re-liquefy. Variations of the polymers prepared using a solvent mixture with 50% benzene and 50% toluene (assume MW ~10 kg/mol) re-liquefy at cold temperatures but were still soft gels. Further synthesis variations using 75/25 and 90/10 solvent mixture ratios (assume MW ~17 and 23 kg/mol) had the same properties as those made with 100% benzene and were the largest polymers (see FIG. 5). Blending the smallest and largest size PNIPAM-PEG-BuMeA polymers produced gels that were stiff and would re-liquefy, but in some cases, these blended compositions suffered from water separation/excretion from the gel.

Figure 22:
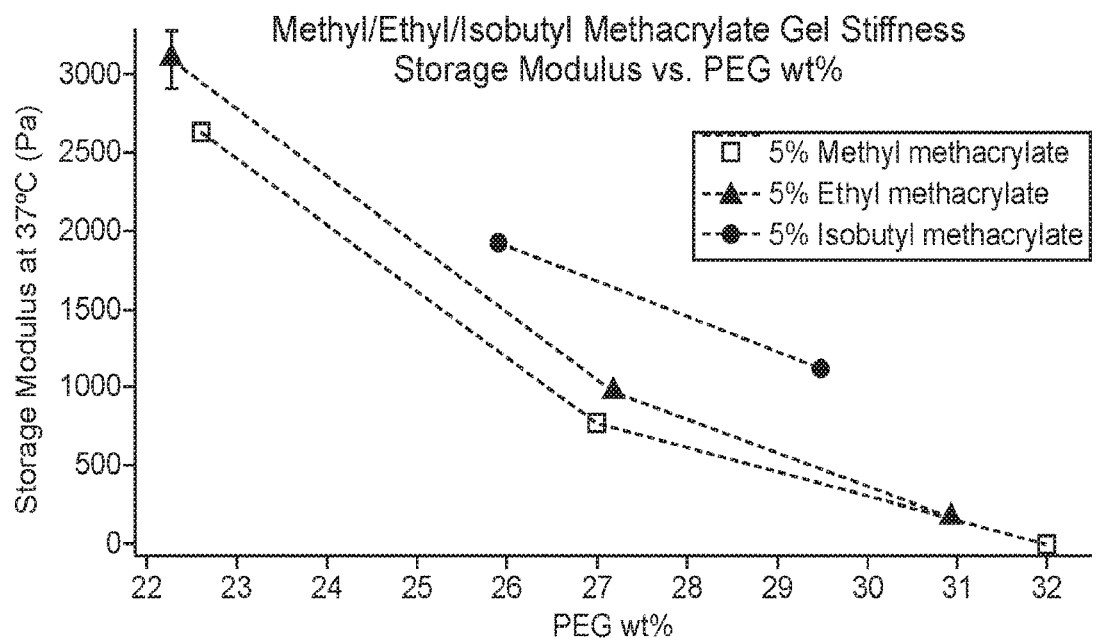
FIG. 22 illustrates the increase in storage modulus as alkyl chain of methacrylate increases (between methyl, ethyl, and isobutyl methacrylates).
Figure 23A:
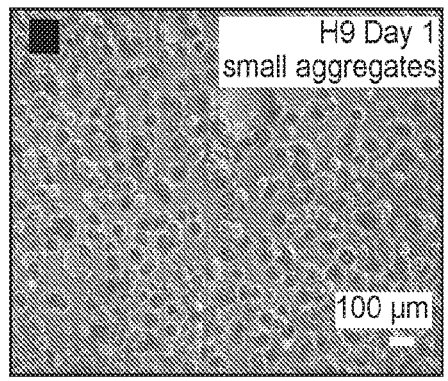
FIG. 23A-23D shows images of single cells and cell aggregates growing in an exemplary PNIPAM-PEG-Isobutyl methacrylate hydrogel: H9 hESC cell growth from day 1 as small aggregates (FIG. 23A) to larger aggregates after 4 days (FIG. 23B). TCTF iPSCs pictures after 1 day as single cells (FIG. 23C) and after 4 days (FIG. 23D). Scale bars are all 100 µm.
Figure 23B:
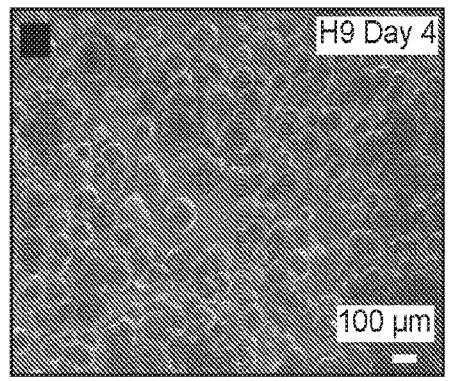
Figure 23C:
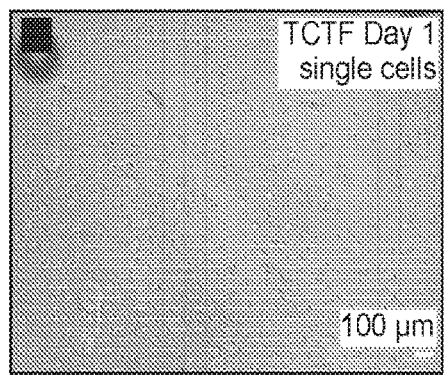
Figure 23D:
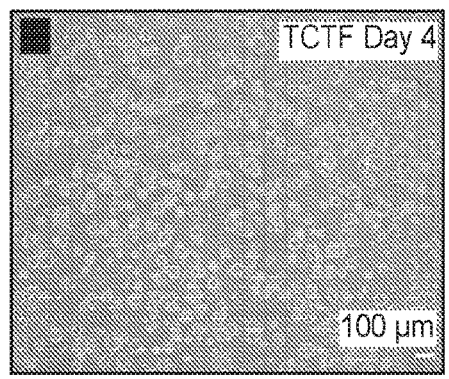
Figure 24A:
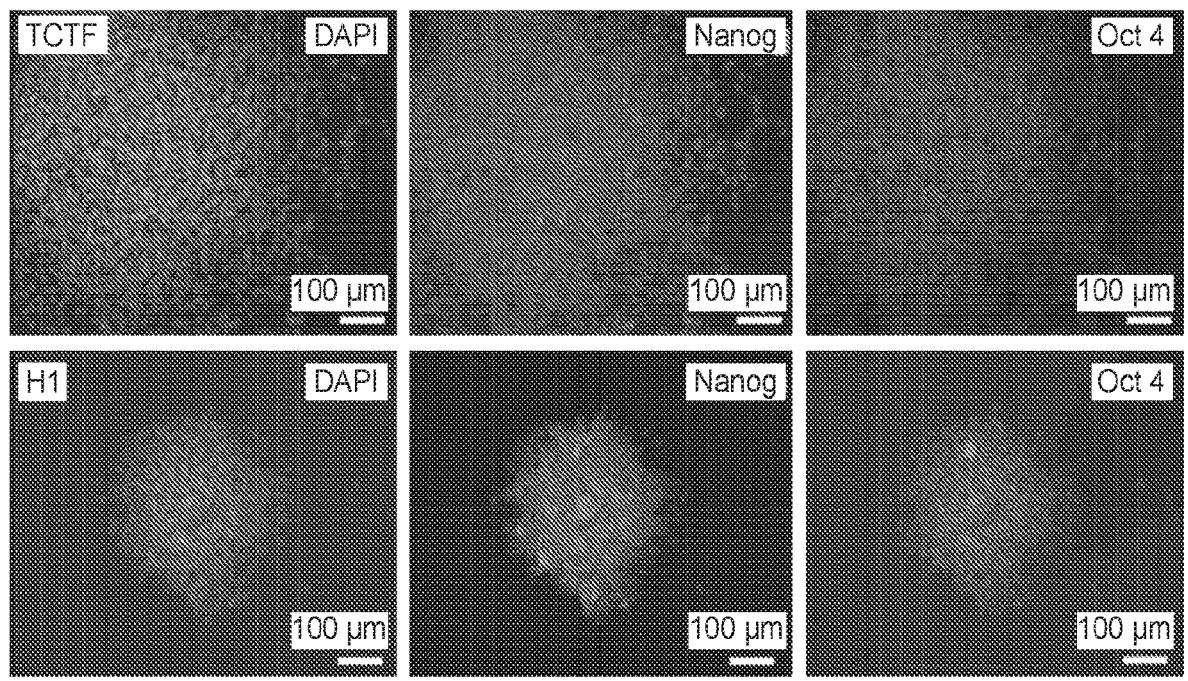
FIG. 24A-24B shows hPSC pluripotency marker expression after cells were grown for multiple passages within PNIPAM-PEG-Isobutyl methacrylate hydrogels.
Figure 24B:
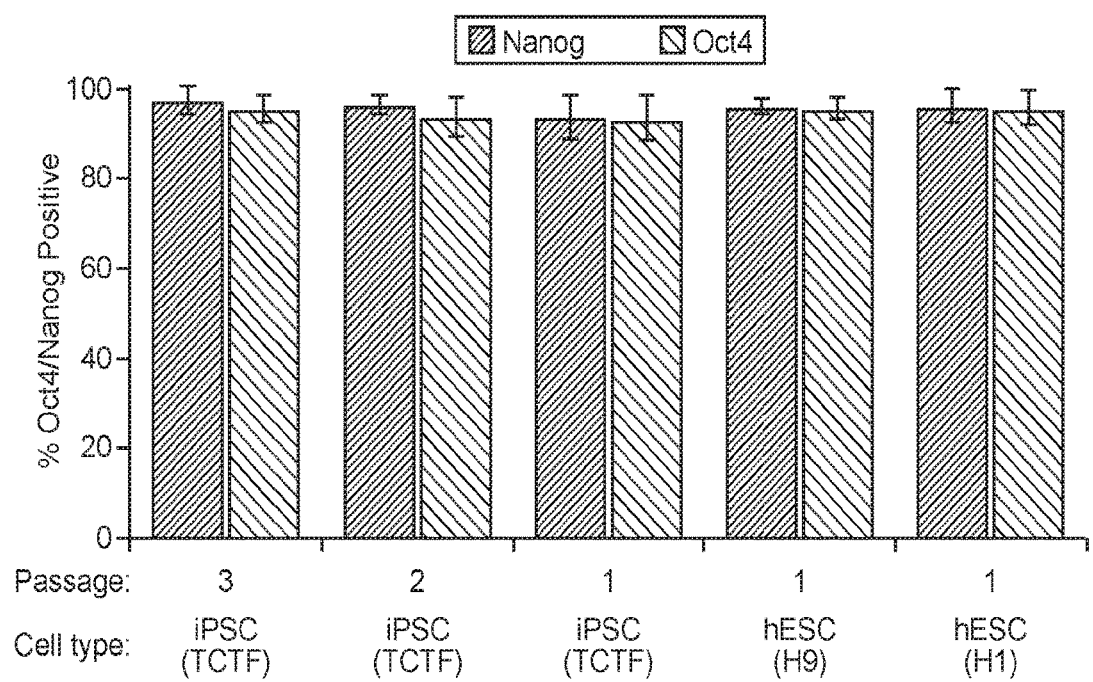
Figure 25A:
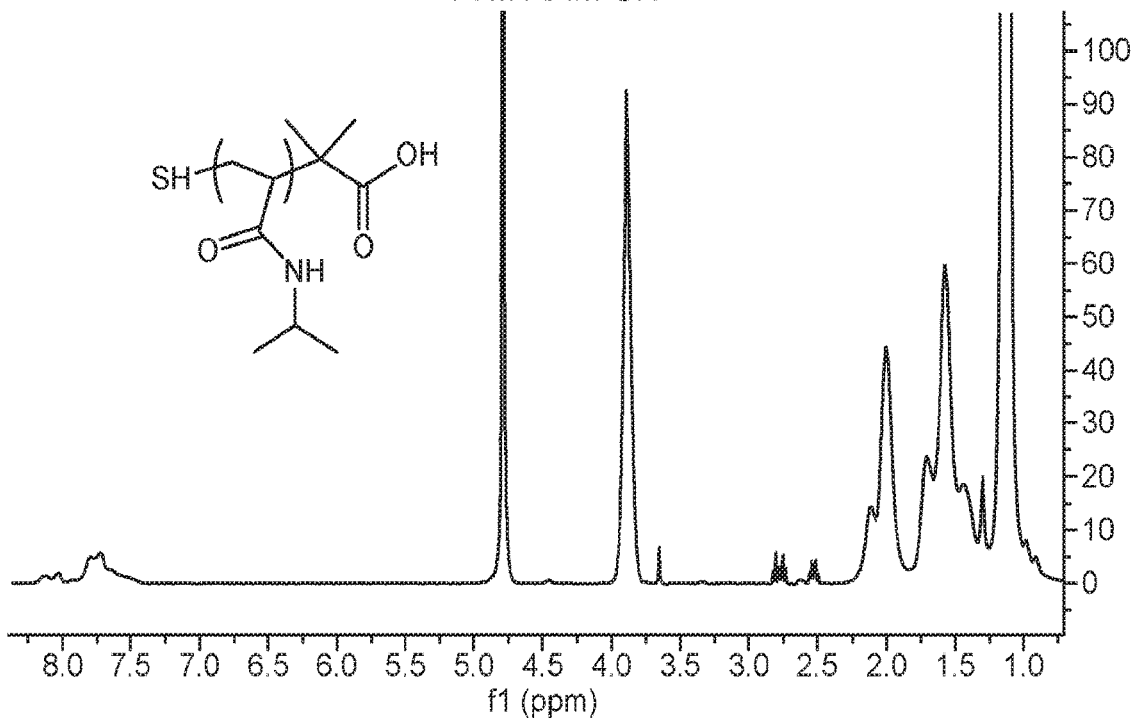
FIG. 25A-25C shows $^1$H NMR spectra of PNIPAM-SH (FIG. 25A), Hyaluronic acid-vinyl sulfone (FIG. 25B), and Hyaluronic acid-PNIPAM (FIG. 25C).
Figure 25B:
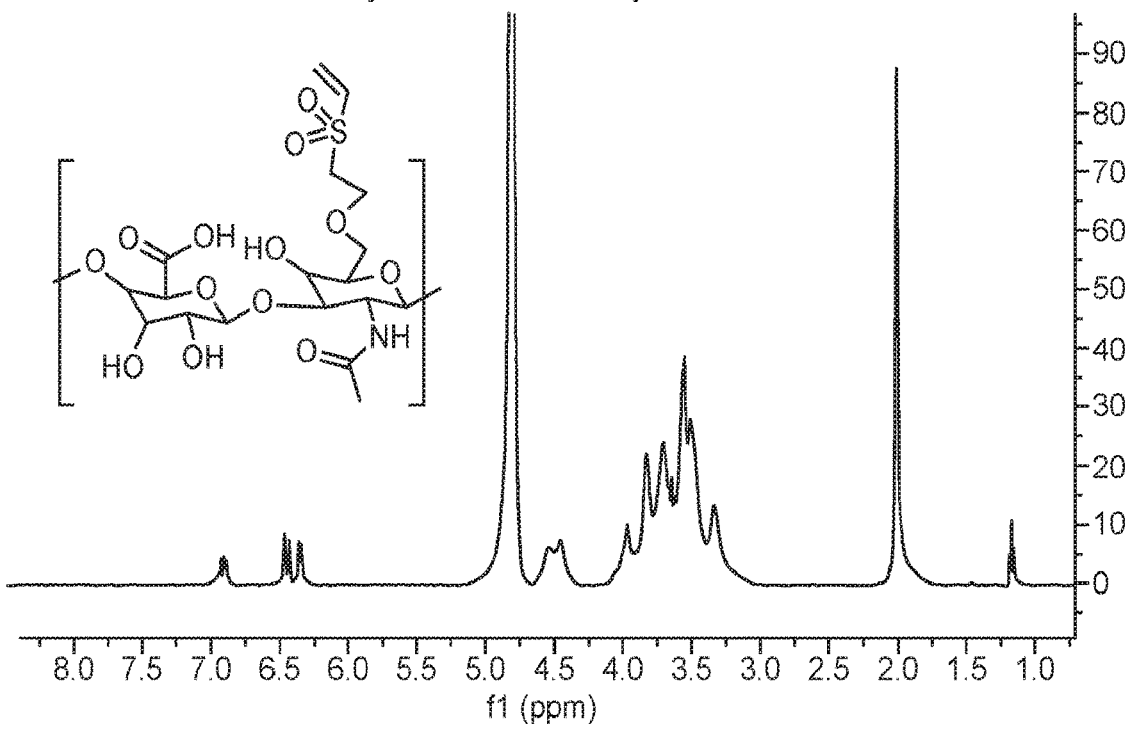
Figure 25C:
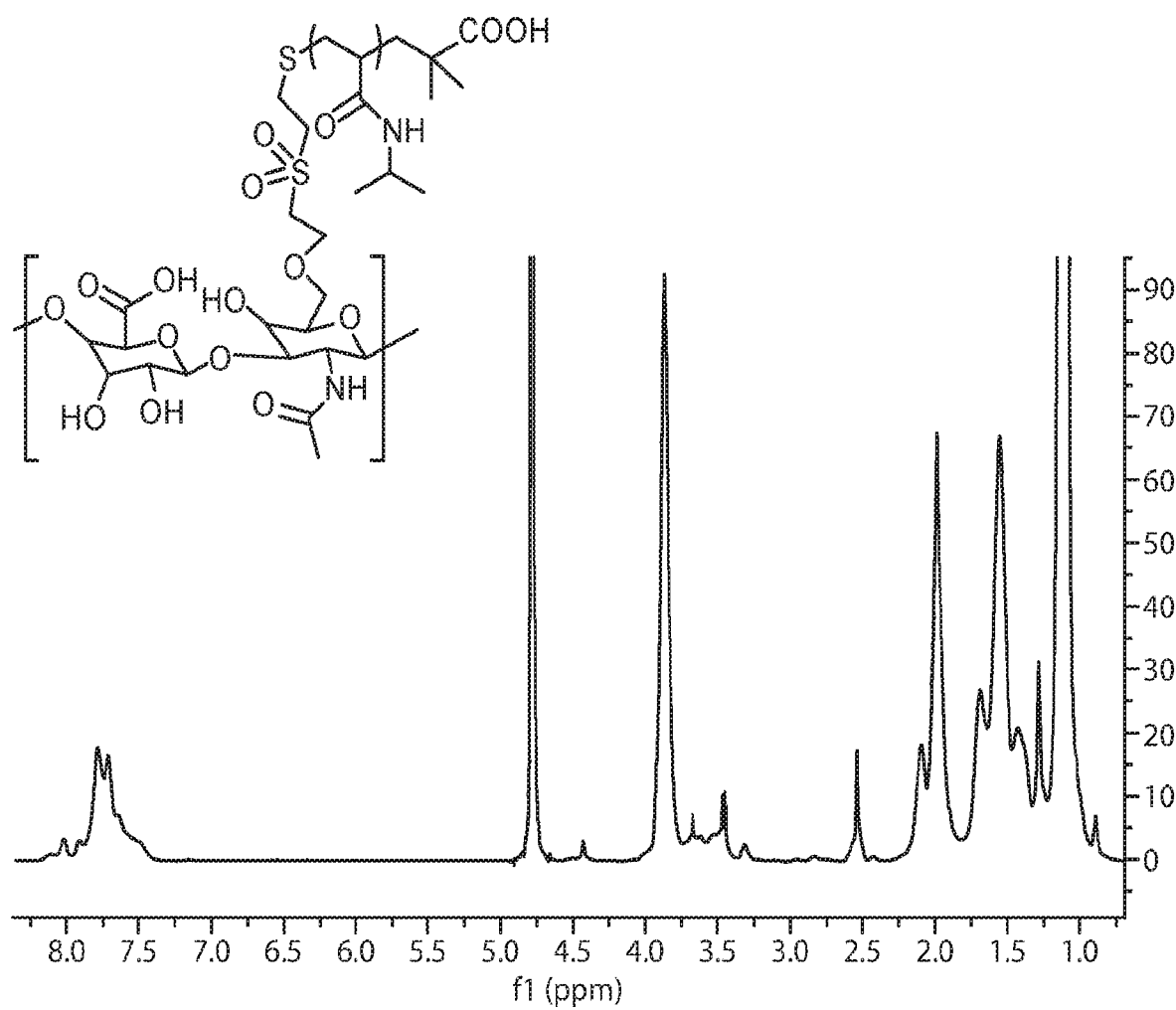

After initial preparations of PNASI-BuMeA polymers, variations were prepared by changing the hydrophobic sidechain group. A variety of methyl/ethyl/isobutyl methacrylates were utilized. PNASI-methyl/ethyl/isobutyl methacrylate polymers made using a solvent blend of 50/50 or 60/40 benzene/toluene did not produce gels at 37° C. but instead produced solids crashing out of water. Polymers made with 80/20 or 90/10 benzene/toluene solvent ratios made stiff, semi-transparent gels that would re-liquefy at cold temperatures, however these polymers would dissolve when additional warm media was added when the PEG chain was 3,400 MW (see FIG. 8). Using a PEG chain of 10,000 MW makes gels that are stiff at 37° C., re-liquify. PNASI-methyl/ethyl/isobutyl methacrylate polymers were made using 100% benzene solvent (~46 kg/mol) and produced clear, stiff gels at 37° C. that would not re-liquefy at 10 wt/vol %. Increasing alkyl chain length also increased the storage modulus (see FIG. 22). Isobutyl methacrylate gels optimized with the appropriate solvent ratio and polymer concentration successfully maintained their hydrogel state for at least 5 days in cell culture, providing sufficient time for cell propagation. Using lower concentrations of 7.5 and 5 w/v % provides for culturing of cells and cell recovery at cold temperatures (see FIG. 7A-7D and FIG. 23A-23D). Human embryonic stem cells (hESCs) and/or induced pluripotent stem cells (iPSCs) were cultured within these gels and remained pluripotent after multiple passages (see FIG. 24A-24B). The PEG length and content can be moditied as desired to alter the LCST and stiffness of these materials depending on the cells and desired cell culture.

Example 3: Addition of Modifying Agents

Figure 9:
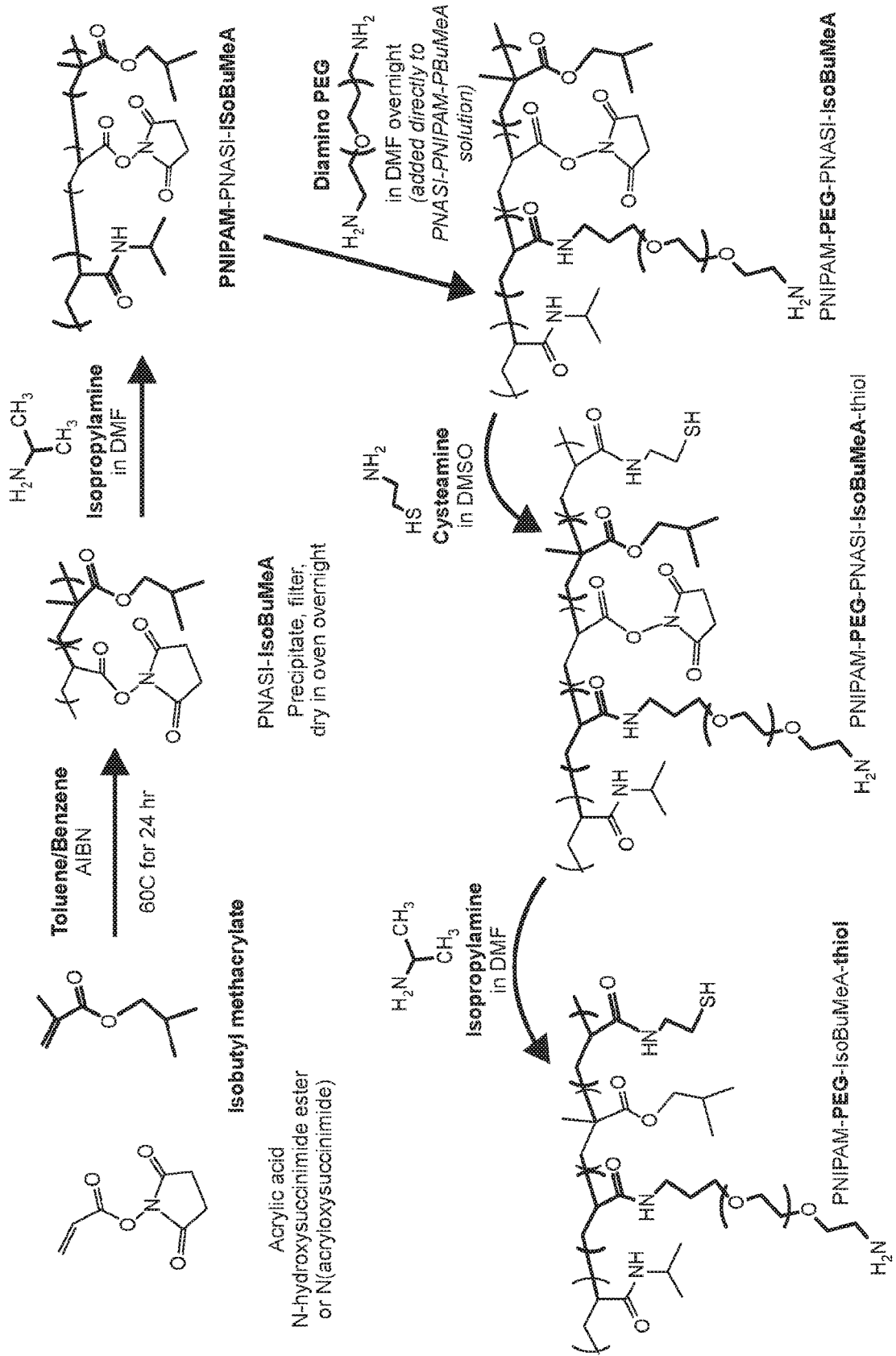
FIG. 9 depicts a scheme for the preparation of a PNIPAM-PEG-Isobutyl methacrylate-thiol thermoreversible polymer.
Figure 10:
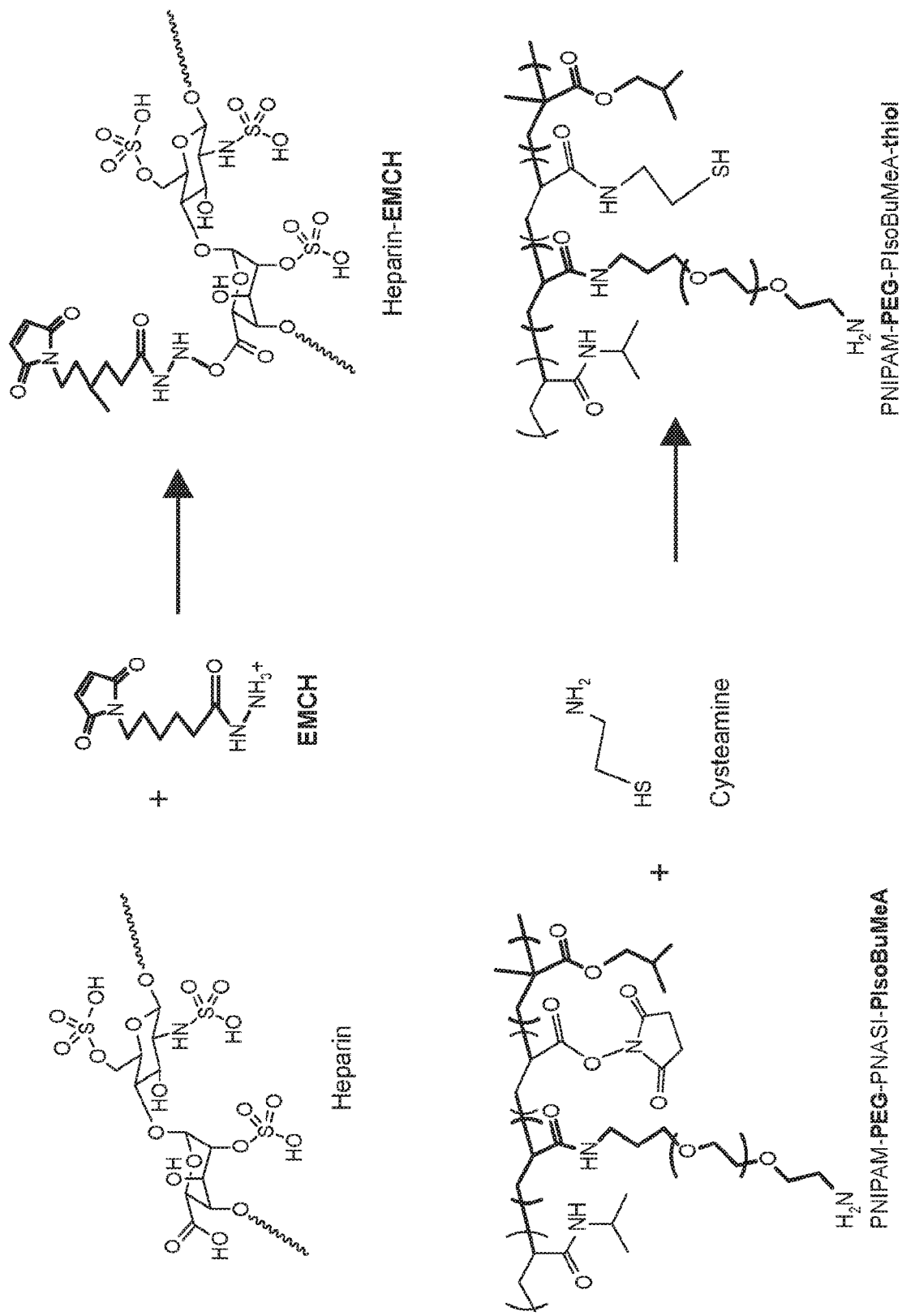
FIG. 10 illustrates heparin functionalization and attachment to an exemplary PNIPAM-PEG-IsoBuMeA-thiol polymer.
Figure 11:
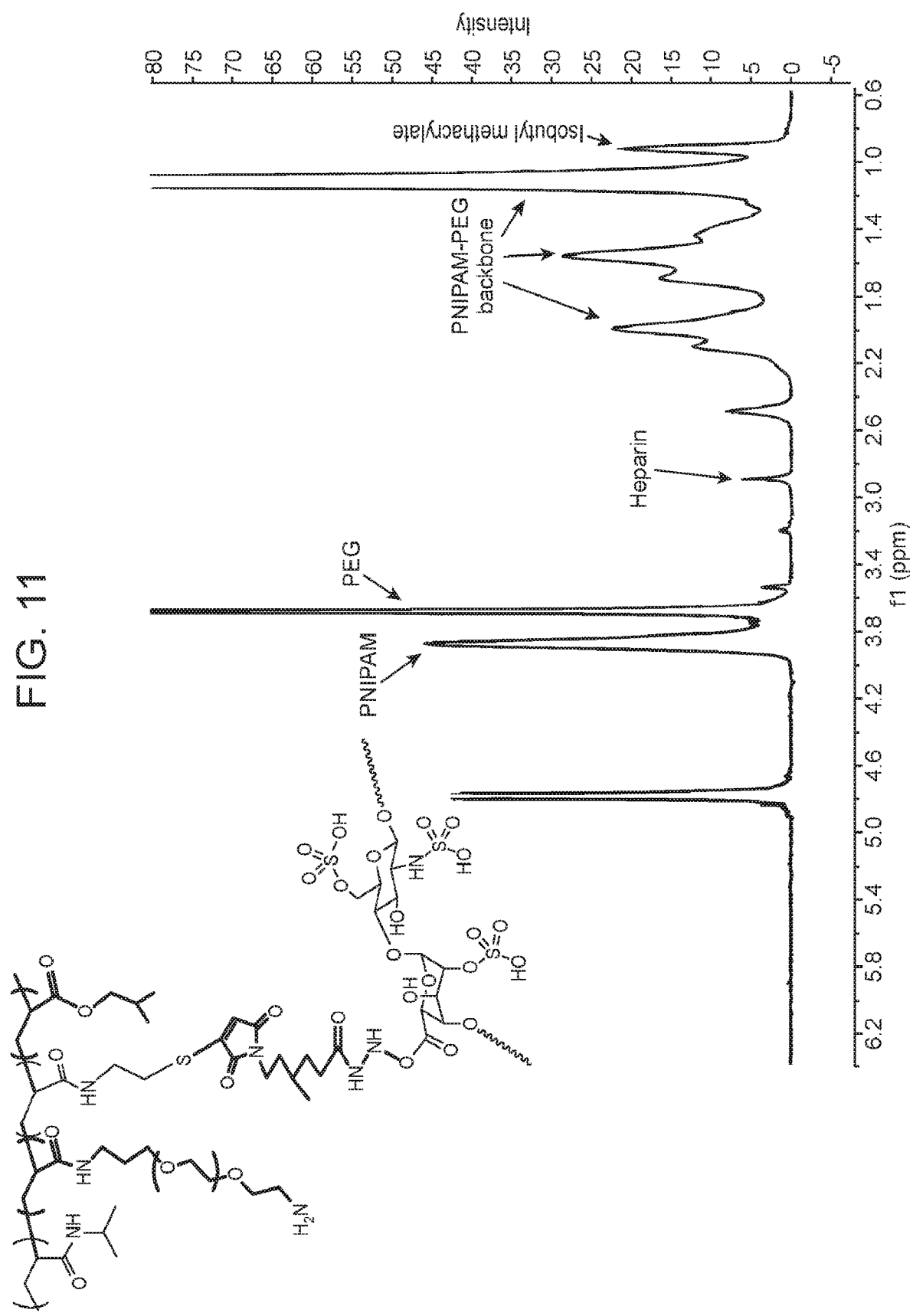
FIG. 11 depicts a $^1$H NMR spectrum showing heparin conjugated to an exemplary PNIPAM-PEG-Isobutyl methacrylate polymer.
Figure 12:
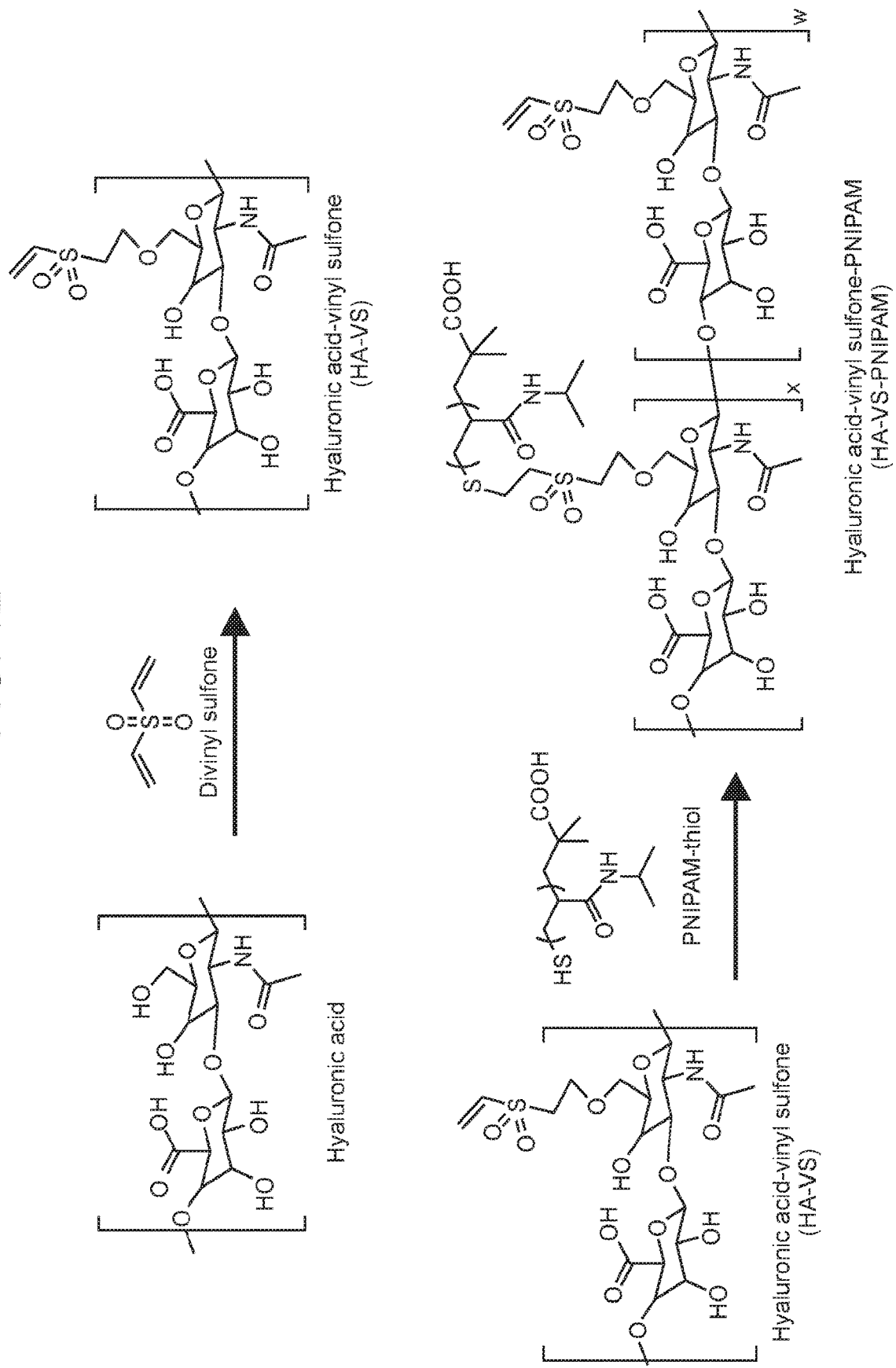
FIG. 12 depicts an exemplary conjugation scheme including hyaluronic acid divinyl sulfone chemistry with a PNIPAM-thiol polymer.

The synthetic scheme for preparation of the PNIPAM-PEG-based thermoreversible polymers provides for addition of functional components that have free amines for reaction with the NHS ester on the PNASI groups. DiaminoPEG is used to incorporate PEG into the system and isopropylamine is used to incorporate PNIPAM. To make simply PNIPAM-PEG-BuMea/IsoBuMeA the reaction is finished with excess isopropylamine, but instead it is possible to add in additional functionality before converting any remaining NHS ester sidechain groups into PNIPAM sidechain groups. One way to do this is by using cysteamine to create thiols along the chains (FIG. 9). The resulting sidechain thiols can then be subsequently reacted with other components or modifying agents or biochemical cues after the entire polymer has been purified and dried. Heparin incorporation is easily accomplished by functionalizing the heparin with N-maleimidocaproic acid hydrazide (EMCH) so that the maleimide groups of EMCH can undergo Michael-addition type reaction with the free thiols on the PNIPAM-PEG-methacrylate polymer (see FIG. 10 and FIG. 11). Many other chemical functionalities can be used to functionalize the polymer before or after purification. Any convenient amine-containing bifunctional linker or biochemical cue can be attached to provide additional benefit or to chemically attach other components to the polymer after purification. Additionally, a free amine on the PEG group terminal can be used for chemical conjugation to an agent of interest.

Example 4: Hyaluronic Acid-PNIPAM Conjugation

Figure 13:
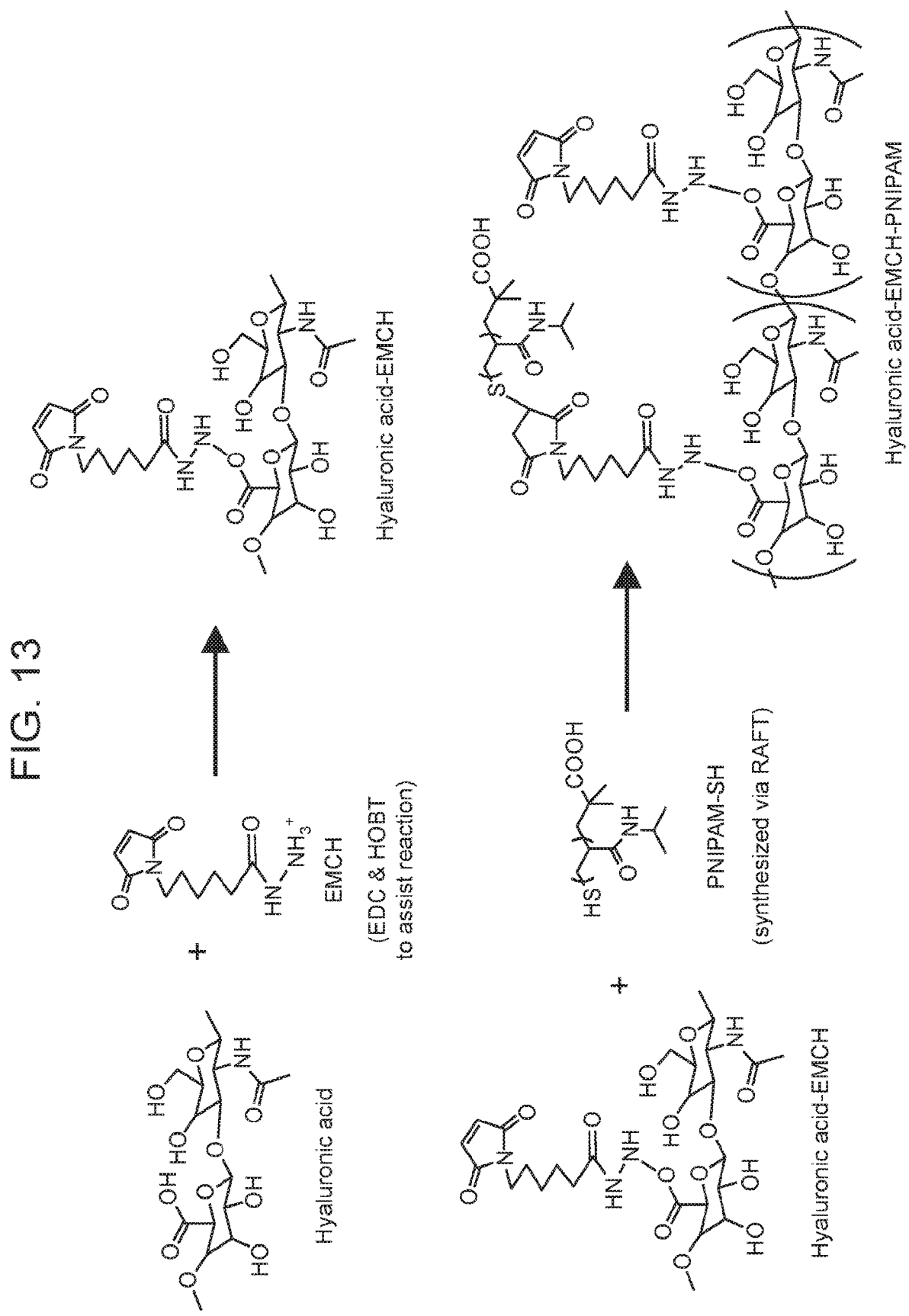
FIG. 13 depicts an exemplary scheme for functionalizing hyaluronic acid with a linked maleimide group for subsequent thiol conjugation chemistry.
Figure 14:
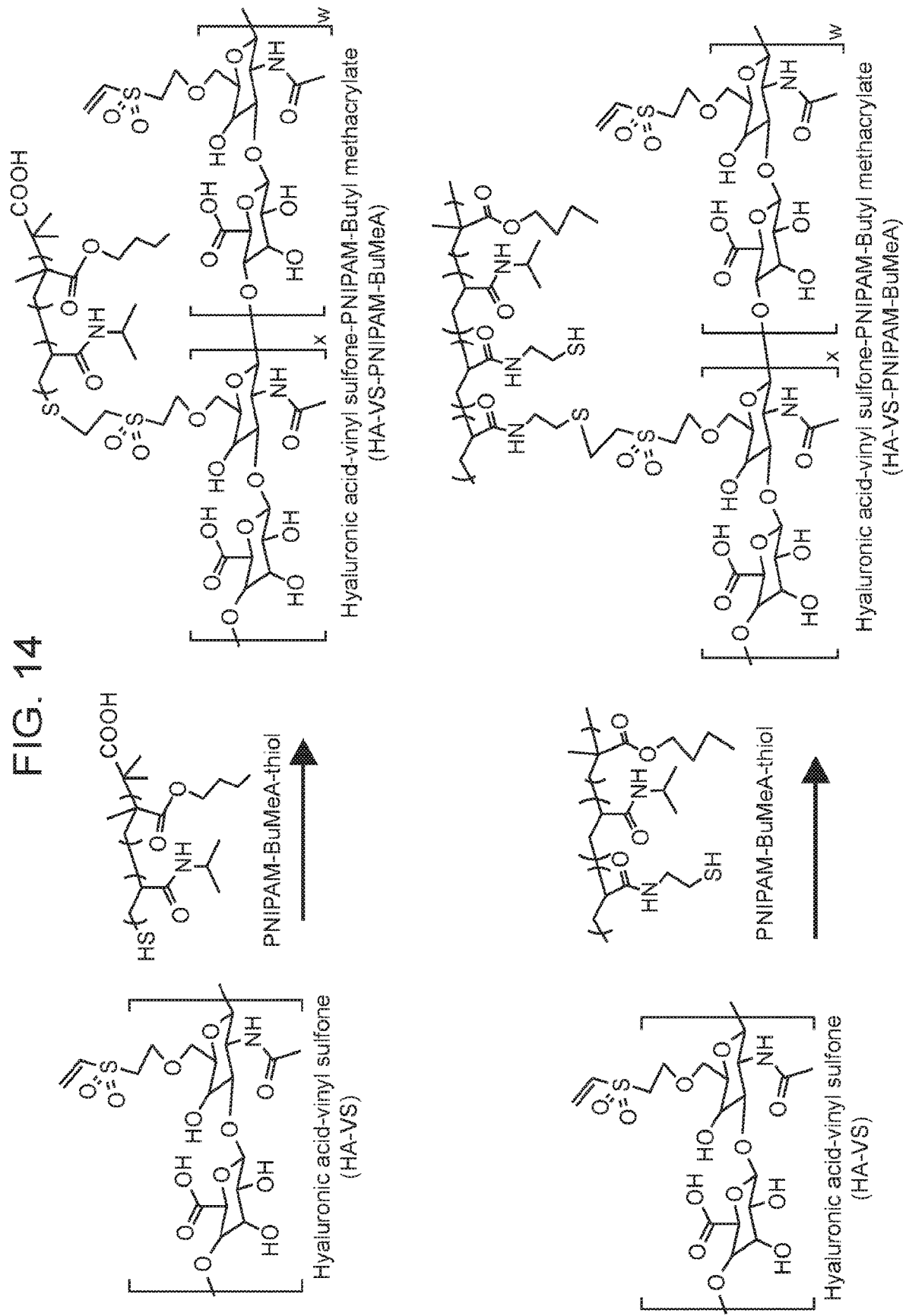
FIG. 14 depicts an exemplary scheme for preparation of hyaluronic acid (HA) conjugates with an exemplary PNIPAM-BuMeA thiol polymer using a vinyl sulfone/thiol linkage.
Figure 15:
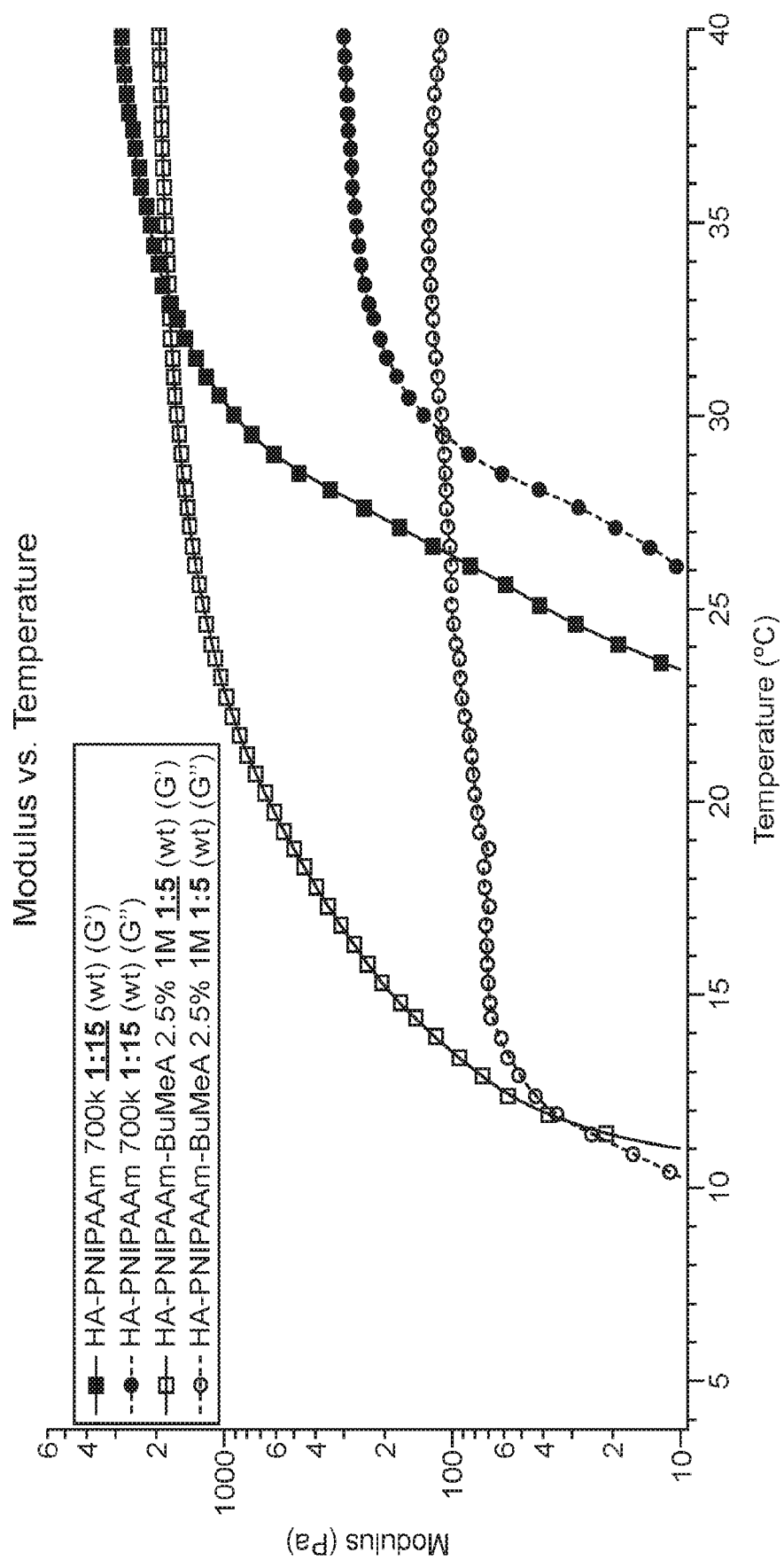
FIG. 15 provides a rheology plot of an exemplary hyaluronic acid-vinyl sulfone-PNIPAM thermoreversible polymer with and without a butyl methacrylate co-monomer showing that incorporation of butyl methacrylate can lower LCST while maintaining stiffness around 1 kPa.
Figure 16:
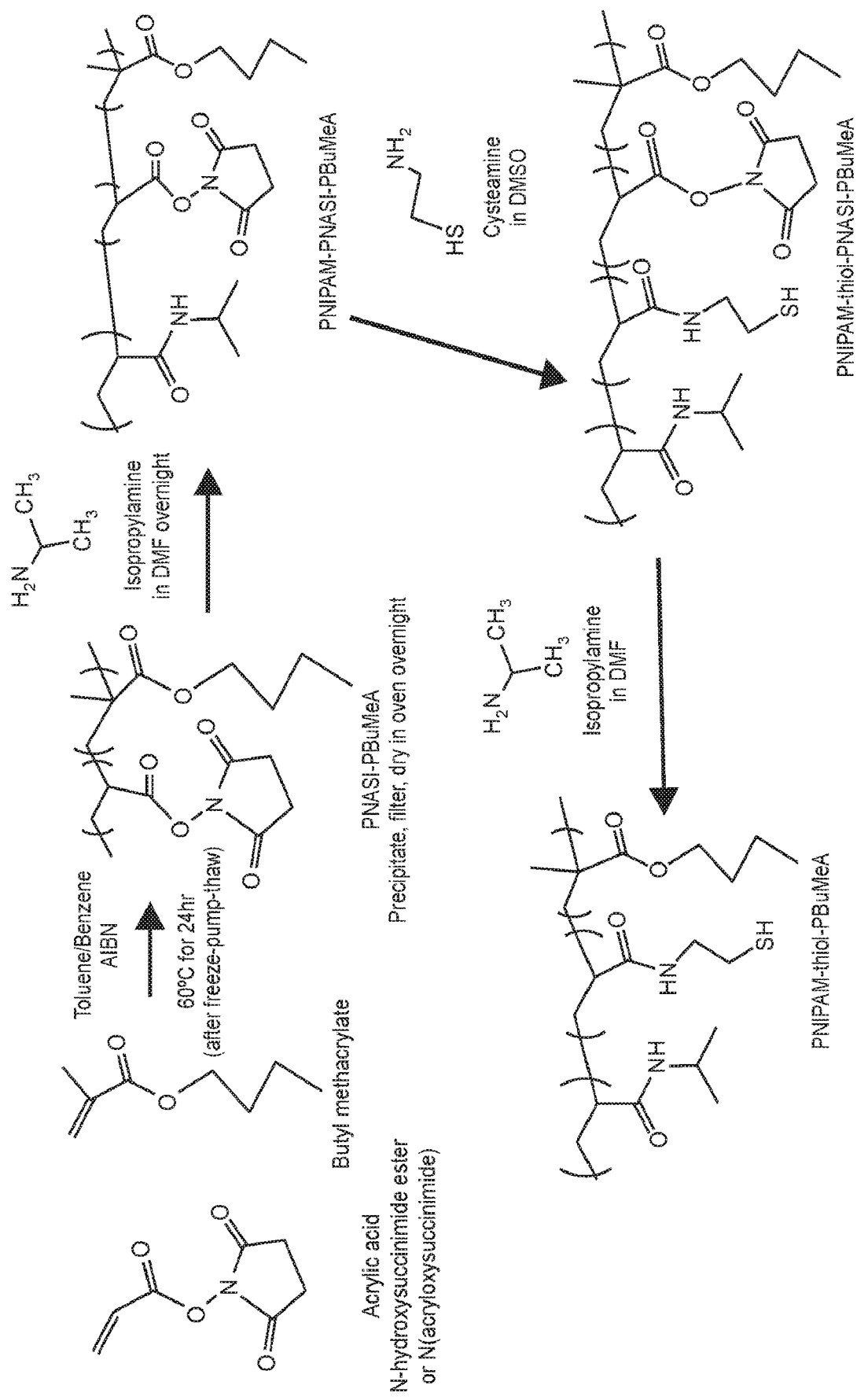
FIG. 16 depicts an exemplary scheme for synthesis of an exemplary PNIPAM-BuMeA-thiol polymer including thiol groups present on sidechain linkers throughout the polymer chain.

In the hyaluronic acid system, hydroxyl groups on the disaccharides are modified to attach vinyl sulfone groups. These chemoselective groups can react with thiol-containing polymers or biochemical cues to functionalize the hyaluronic acid (see FIG. 12). Additionally, EMCH can be used to functionalize the hylauronic acid with maleimide groups via the carboxylic acids (FIG. 13). PNIPAM polymer is synthesized via reversible addition-fragmentation chain transfer (RAFT) using a chain transfer agent containing a thiolcarbonylthio group, which can be cleaved to reveal a thiol on each chain end. Butyl methacrylate or other hydrophobic methacrylate groups can be included as a co-monomer during the synthesis reaction to create polymers with lower LCSTs than PNIPAM alone (FIG. 14 and FIG. 15). PNIPAM-BuMeA-thiols can also be prepared using similar methods to those used at the start of the PNIPAM-PEG system with PNASI-BuMeA. Addition of isopropylamine to make NIPAM groups and cysteamine to make thiols makes polymer chains that may have multiple thiols per chain (FIG. 16).

Figure 26A:
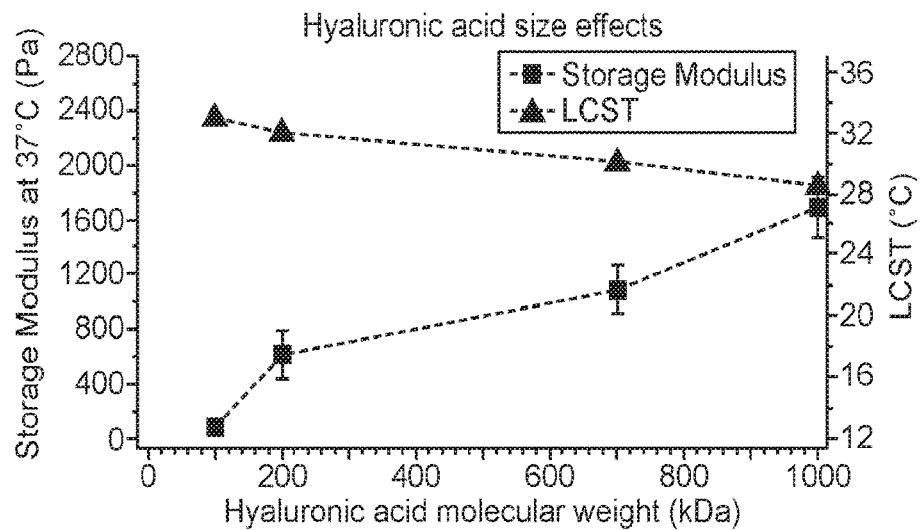
FIG. 26A-26C illustrates rheological effects of hydrogels based on HA size, component ratios, polymer concentration, and BuMeA content.
Figure 26B:
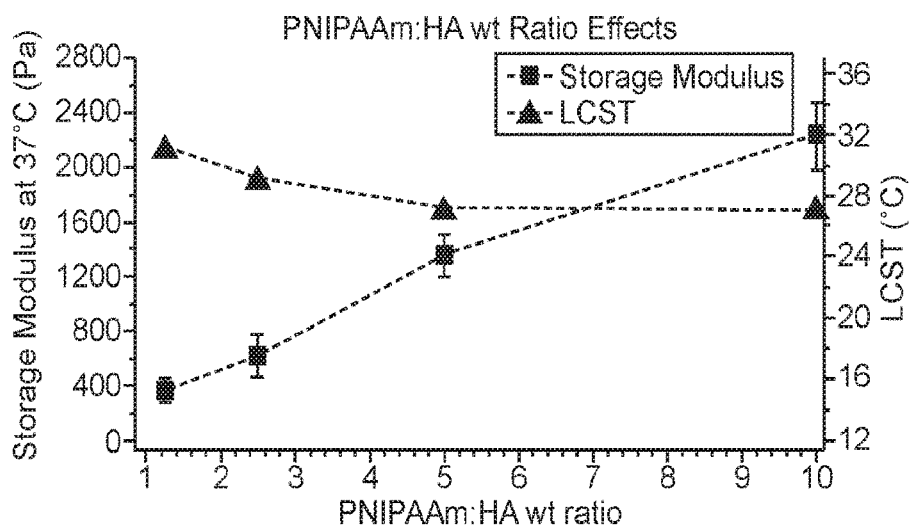
Figure 26C:
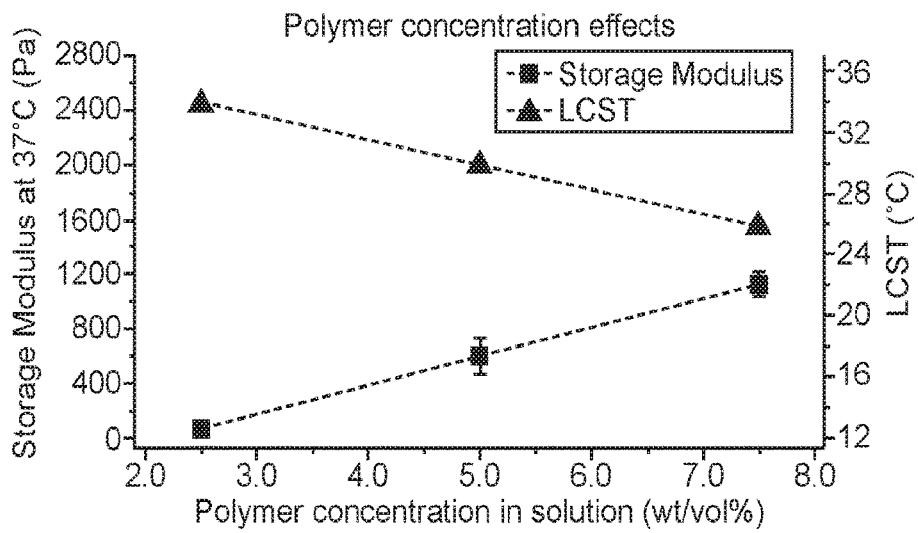
Figure 27A:
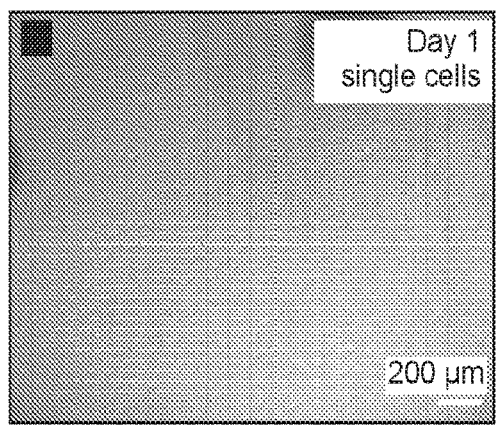
FIG. 27A-27D shows images of cell growth for different cell lines growing in HA-PNIPAM hydrogels.
Figure 27B:
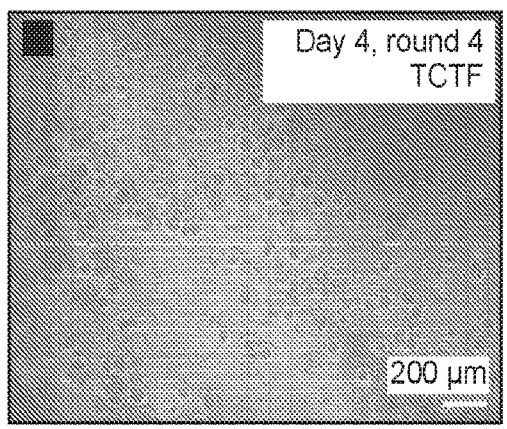
Figure 27C:
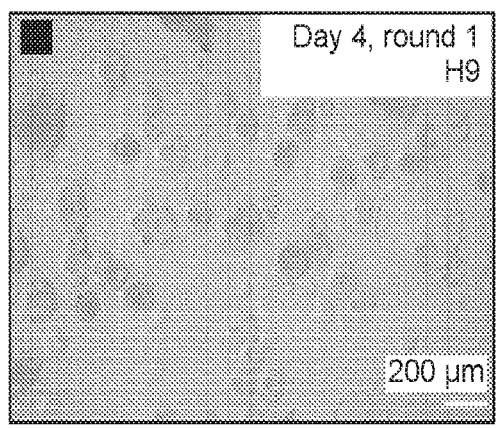
Figure 27D:
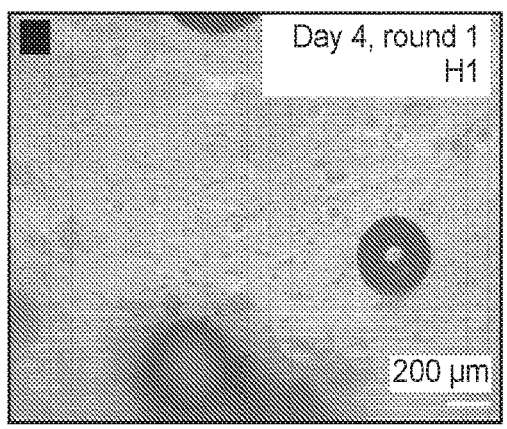
Figure 28:
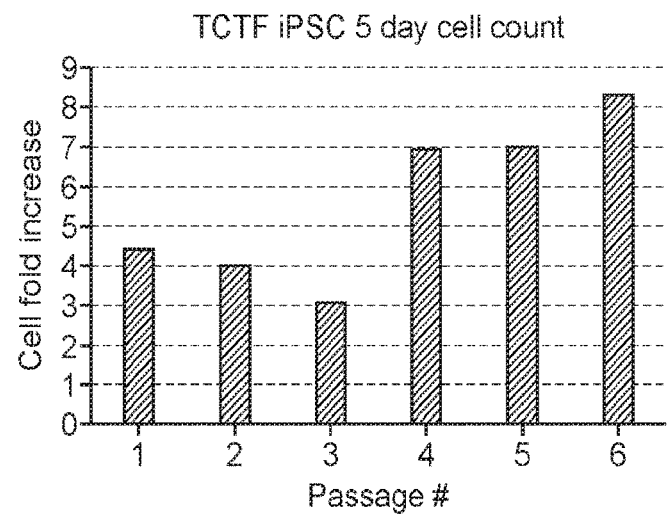
FIG. 28 shows the TCTF iPSC growth capability within the HA-PNIPAM hydrogels through multiple passages.
Figure 29A:
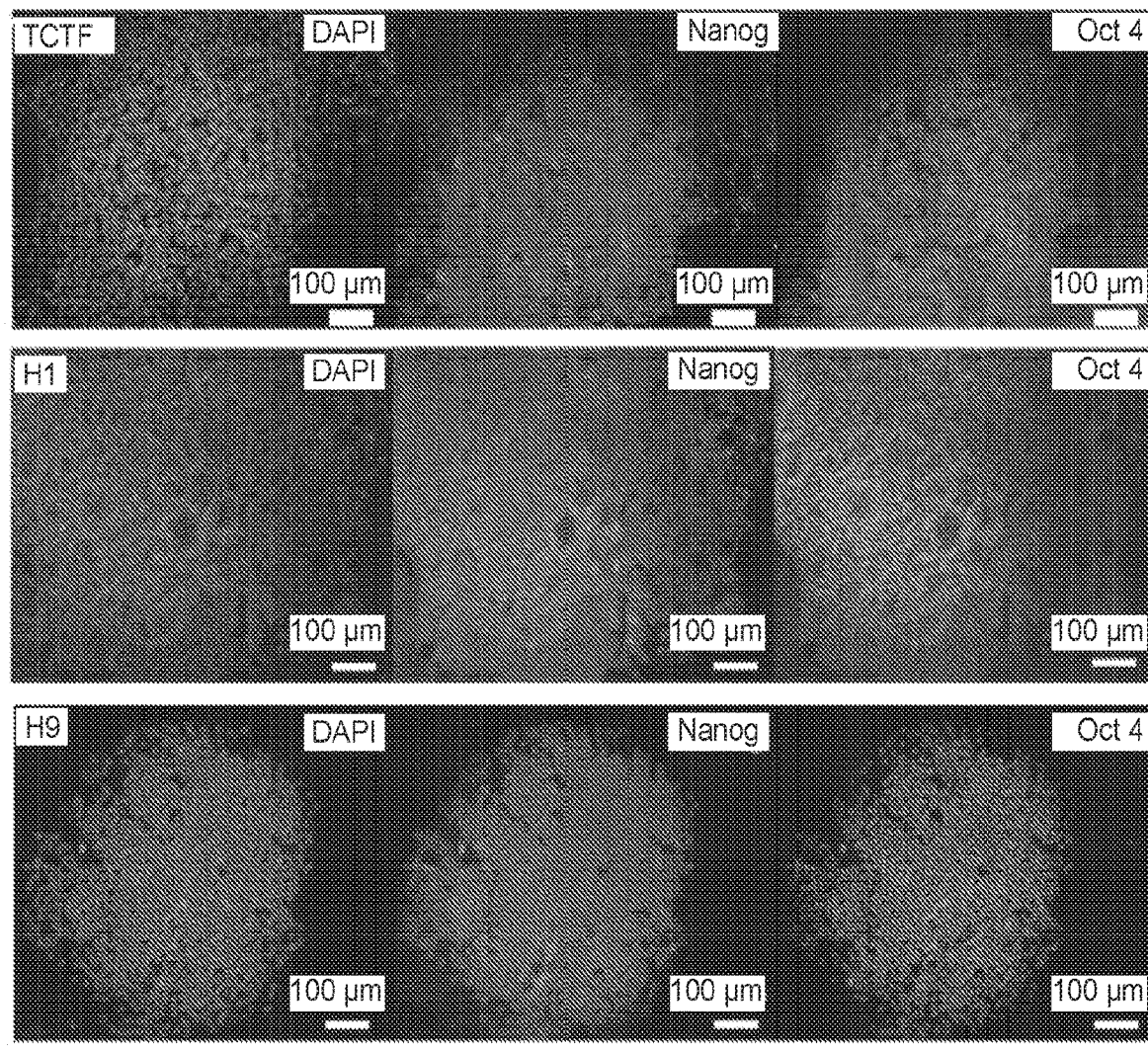
Figure 29B:
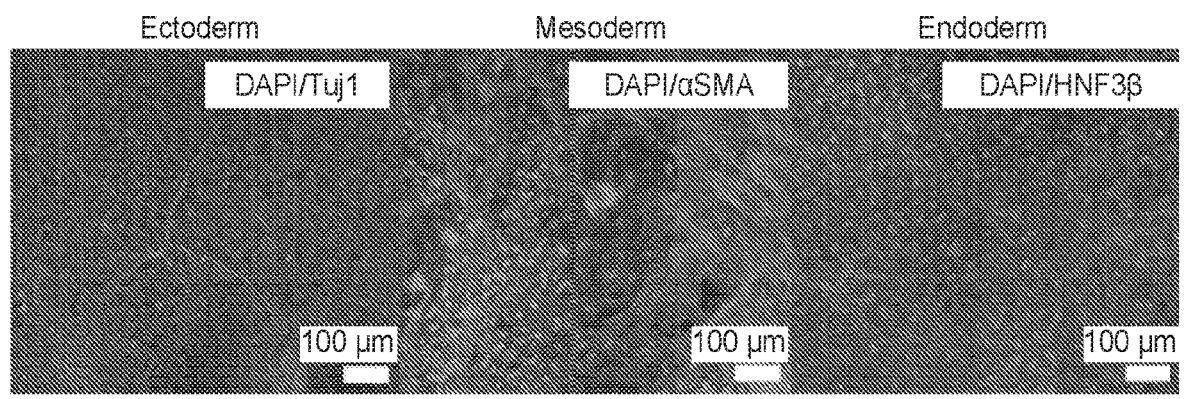

Many factors affect both the storage modulus and the LCST of the final hydrogels. Increasing the molecular weight of hyaluronic acid increases the storage modulus (see FIG. 26A). Similarly, increasing the weight ratio of PNIPAM to hyaluronic acid also increases the storage modulus (see FIG. 26B). Increasing polymer concentration follows a similar trend up to 7.5% w/v % (FIG. 26C). Addition of butyl methacrylate co-monomer to the polymeric material can decrease the LCST from ~30° C. to below room temperature (FIG. 15), however the mol percent of butyl methacrylate within the co-monomer must be below 3.5% to maintain gel-like properties. This property of the material is useful for cell culture since if using gels on plates, the time outside the incubator for media changes or imaging could allow the material to re-liquefy. Incorporating a component to decrease the LCST helps to tailor the material for a desired application. Keeping LCST close to body temperature could be useful for injections, but a lower LCST is useful for cell culture or other uses outside the body.

Optimized HA-PNIPAM gels were successfully used to culture multiple types of human pluripotent stem cells (hPSCs) including H1 and H9 hESCs and TCTF iPSCs (see FIG. 27A-27D). The gels maintain a favorable environment for the cells to replicate and remain pluripotent over the course of multiple passages (see FIG. 28 and FIG. 29A-29C). In addition, neural stem cells (NSCs) can grow within these gels and remain multipotent after multiple passages (see FIG. 30A-30D)

Figure 17:
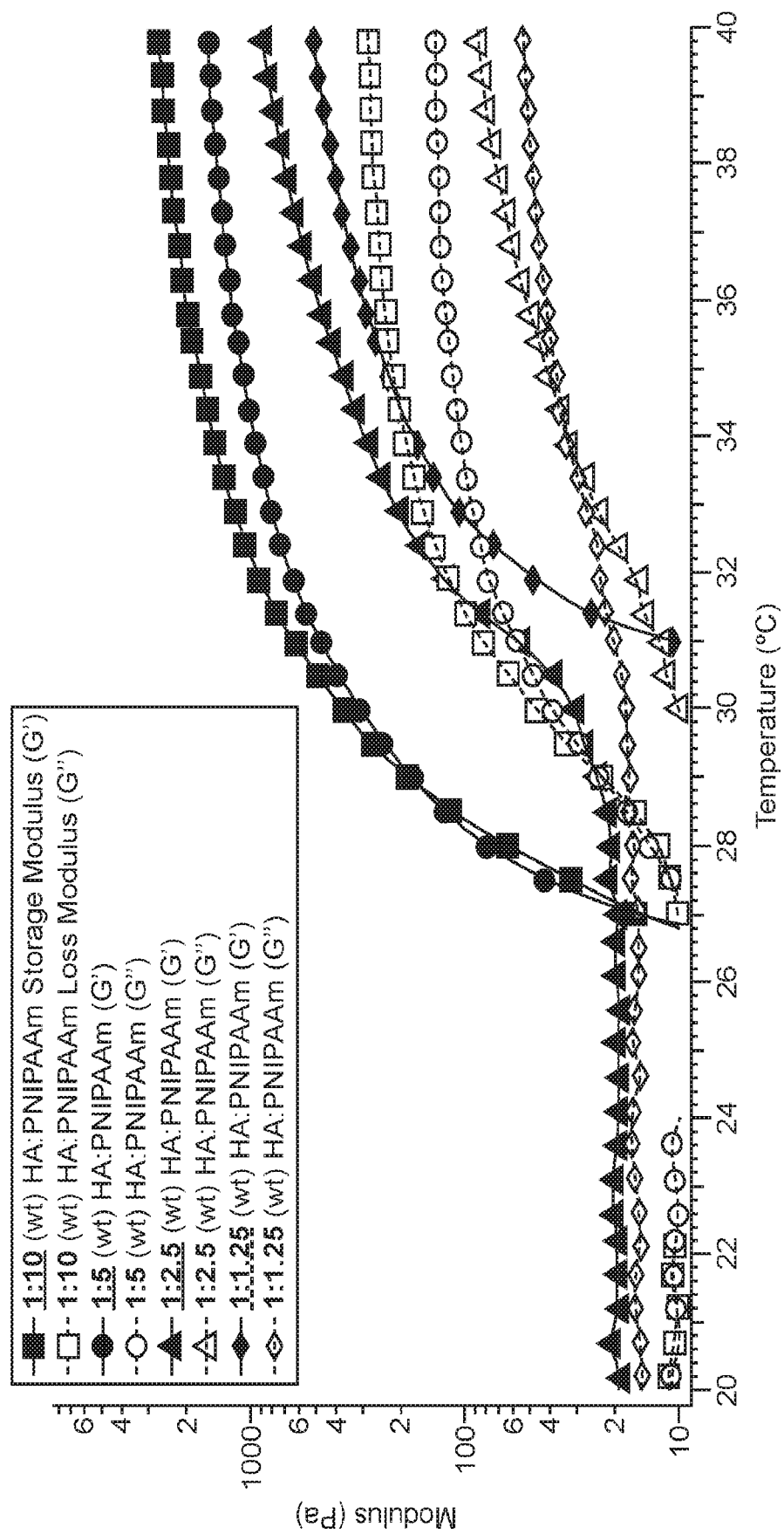
FIG. 17 provides a rheology plot of modulus vs. temperature for exemplary HA-PNIPAM polymers prepared using various ratios of PNIPAM:HA by weight. As less PNIPAM is added, the gels become softer and have a higher lower critical solution temperature (LCST).
Figure 18:
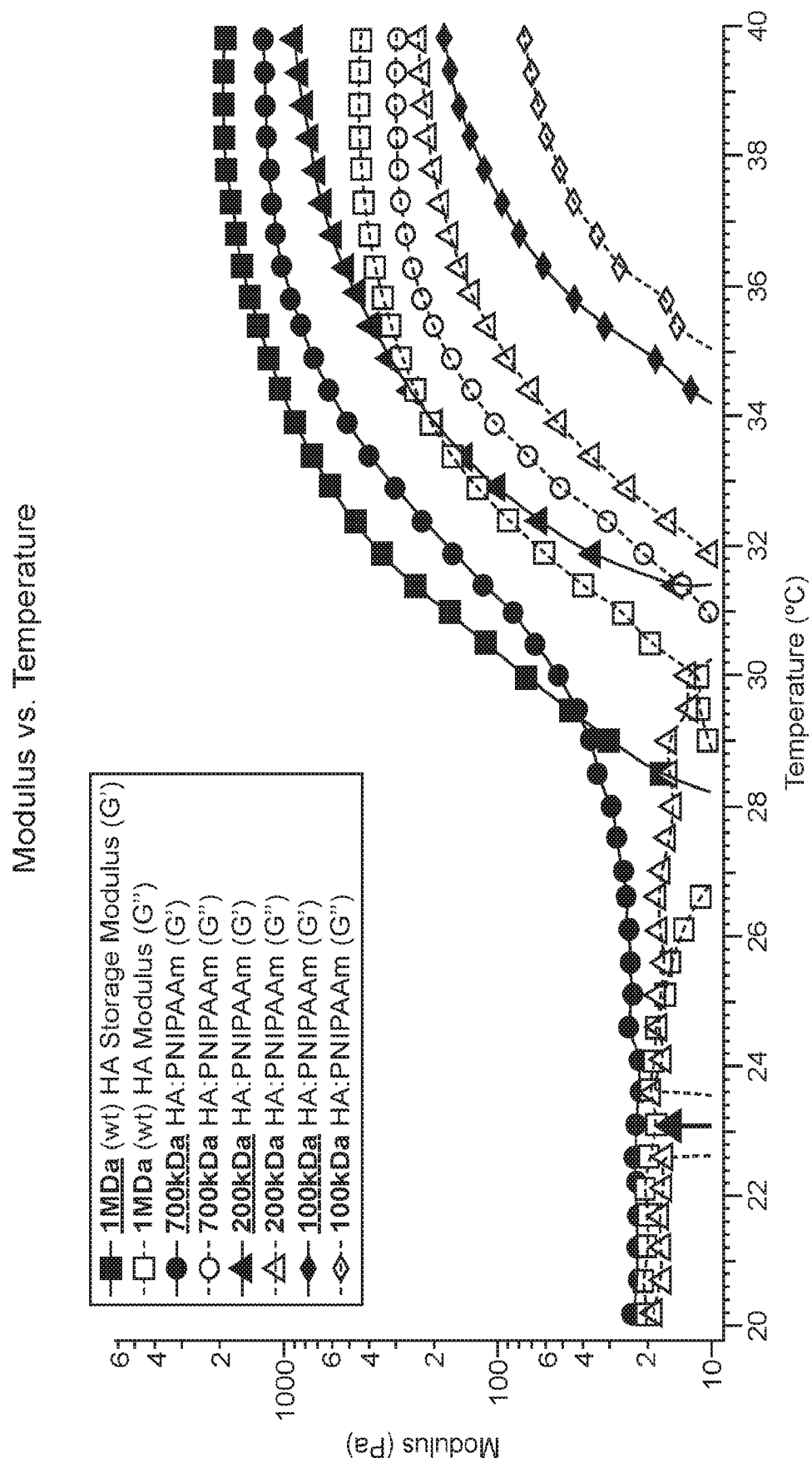
FIG. 18 provides a rheology plot of modulus vs. temperature showing that a smaller MW Hyaluronic acid can produce softer and higher LCST gels.

Changing the ratio of PNIPAM to hyaluronic acid can modulate not only the LCST but also the stiffness (FIG. 17). Addition of butyl methacrylate co-monomer to the polymeric material can decrease the LCST from ~30° C. to below room temperature (FIG. 15). This property of the material is useful for cell culture since if using gels on plates, the time outside the incubator for media changes or imaging could allow the material to re-liquefy. Incorporating a component to decrease the LCST helps to tailor the material for a desired application. Keeping LCST close to body temperature could be useful for injections, but a lower LCST is useful for cell culture or other uses outside the body. Increasing the size of the hyaluronic acid from 200 kDa to 1 MDa can drastically increase viscosity at cold temperatures as well as stiffness at 37° C. (FIG. 18).

Since this system has vinyl sulfone groups available for thiol chemistry, any biomolecules or biochemical functionalized with thiols can attach and provide additional biocompatibility. Heparin can be functionalized using cysteamine and EDC/HOBT chemistry to introduce chemoselective thiol groups. This modified heparin agent can subsequently be added to the Hyaluronic acid-vinyl sulfone-PNIPAM system, for example, by attaching the linker of the modified heparin, "HS" thiol, to the vinyl sulfone group (FIG. 19).

Chemical Functionality:

The polymers incorporate chemical functionality in order to attach heparin for subsequent protein attachment or other biochemical cues such as peptides. This helps to increase local concentration and potency of the proteins and limit endocytosis by the cells. Modifying the proteins and other attached cues can better reflect the native tissue environment and aid cells in replicating or differentiating to a specific lineage.

Physical Property Modifications:

The polymeric materials can be altered by their relative component ratios and/or chemical makeup in order to select a desired physical property. Stiffness at warm temperatures and viscosity at cold temperatures can be modulated to encapsulate the cells and to better mimic a variety of native tissue environments.

Thermoreversibility:

The polymers include thermoreversible components in order to easily recover and passage cells for large production. Thermoreversibility eliminates the need to use harsh steps to recover cells and instead can minimize external stress cells experience during passaging. The temperature at which the materials gel can be selected for ease of handling.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

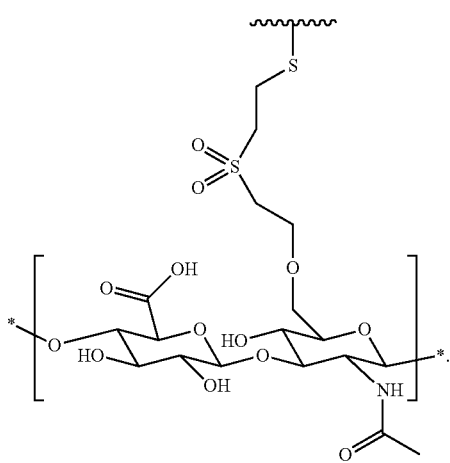

What is claimed is:

1. A thermoreversible polymer comprising:
   a N-isopropylacrylamide co-monomer;
   an alkyl [meth]acryl[ate/amide] co-monomer, wherein the alkyl is a lower alkyl group;
   a PEG acrylamide co-monomer; and
   a modifying acryl[ate/amide] co-monomer comprising a linked functional group or a linked modifying agent,
   wherein the thermoreversible polymer is described by formula (II):

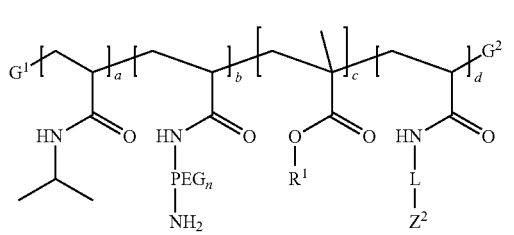

(II)

wherein:
a, b, c and d are molar fractions of the co-monomers, wherein a >0.8, 0.1>b >0, and 0.2>c>0;
$PEG_n$ is a polyethylglycol polymer;
$Z^2$ is a functional group or a linked modifying agent;
L is a linker;
$R^1$ is a lower alkyl;
$G^1$ and $G^2$ are each independently selected from a polymer segment, a terminal group, a linker and a linked modifying agent.

2. The thermoreversible polymer of claim 1, wherein the alkyl [meth]acryl[ate/amide] co-monomer is an isobutyl methacrylate co-monomer.

3. The thermoreversible polymer of claim 1, wherein $R^1$ is selected from the group consisting of methyl, ethyl, propyl, butyl, pentyl, isopropyl, isobutyl, isopentyl, tert-butyl, cyclopropyl, and cyclobutyl.

4. The thermoreversible polymer of claim 1, wherein $Z^2$ is a chemoselective functional group.

5. The thermoreversible polymer of claim 1, wherein $Z^2$ is a linked modifying agent, wherein the modifying agent is selected from a heparin, a hyaluronic acid, a specific binding member, a peptide, a nucleic acid, gelatin, fibronectin, collagen, laminin, bFGF, EGF, insulin, progesterone, glucose, SDF thymosin beta-4, SHH, Noggin, Activin, TGFb3, FGF8, BDNF, GDNF, NT3, PDGF-AA and IGF-1.

6. The thermoreversible polymer of claim 1, described by the formula (IV):

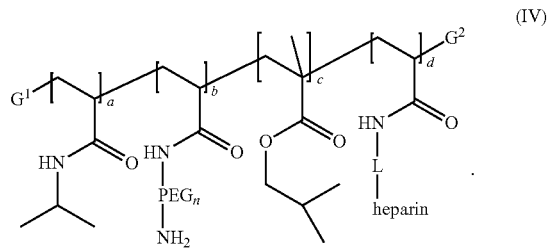

(IV)

7. The thermoreversible polymer of claim 1, wherein $G^1$ and $G^2$ are each independently selected from a terminal group, a linker and a linked modifying agent.

8. The thermoreversible polymer of claim 1, wherein $G^1$, $G^2$ or $Z^2$ comprise a linked hyaluronic acid that is linked via conjugation to the carboxylic acid group of a hyaluronic acid monomer.

9. The thermoreversible polymer of claim 1, wherein $G^1$, $G^2$ or $Z^2$ comprise the following structure:

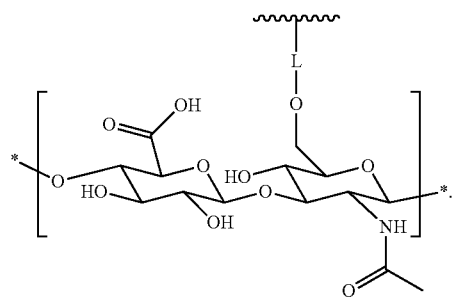

10. The thermoreversible polymer of claim 9, wherein $Z^2$ comprises the following structure:

11. The thermoreversible polymer of claim 1, wherein $G^1$ and/or $G^2$ comprises the following structure:

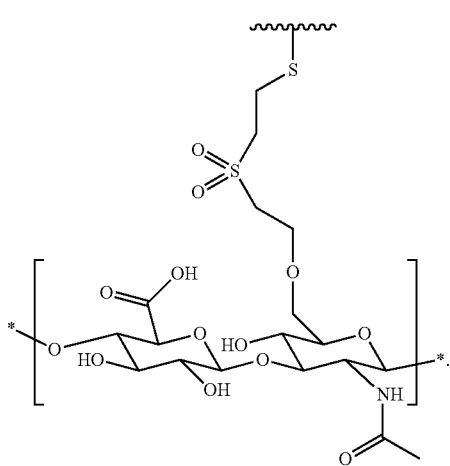

12. The thermoreversible polymer of claim 1, wherein the polymer has a molecular weight (MW) of 5 to 500 kDa.

13. The thermoreversible polymer of claim 1, wherein the PEG or $PEG_n$ has a molecular weight (MW) of 2 to 100 kDa.

14. A hydrogel composition, comprising:
a thermoreversible polymer of claim 1; and
a buffered aqueous solution.

15. The hydrogel composition of claim 14, further comprising cells.

16. The hydrogel composition of claim 15, wherein the cells are stem cells selected from the group consisting of (a) adult stem cell derived from bone marrow, umbilical tissues, or placenta; (b) neural stem cell; (c) a progenitor cell derived from an embryonic stem cell; and (d) embryonic stem cell.

17. The hydrogel of claim 14, wherein the thermoreversible polymer is a solid at 20° C. or more.

18. The hydrogel of claim 17, wherein the thermoreversible polymer is a solid at 37° C.

19. The hydrogel of claim 14, wherein the thermoreversible polymer is a liquid at 30° C. or less.

20. The hydrogel of claim 19, wherein the thermoreversible polymer is a liquid at 4° C.

21. A method of growing mammalian cells, the method comprising:
introducing mammalian cells into the hydrogel composition of claim 14 to produce a culturing mixture comprising a cell construct; and
incubating the culturing mixture under conditions suitable for growth of the mammalian cells.

22. A method of preparing a thermoreversible polymer of claim 1, the method comprising:
co-polymerizing:
an alkyl methacrylate in which the alkyl is one of methyl, ethyl, propyl, butyl, pentyl, isopropyl, isobutyl, isopentyl, tert-butyl, cyclopropyl, and cyclobutyl; and
acrylic acid N-hydroxysuccinimide ester to make a copolymer comprising an acrylic backbone;
contacting the copolymer with isopropylamine to convert a first portion of the N-hydroxysuccinimide ester groups to N-isopropylamine groups;
contacting the copolymer with a diamino-PEG to convert a second portion of the N-hydroxysuccinimide ester groups to N-PEG-$NH_2$ groups; and
contacting the copolymer with an amino linker to convert a third portion of the N-hydroxysuccinimide ester groups to N-linker-$Z^2$ groups, where $Z^2$ is a chemoselective functional group.

* * * * *